(12) United States Patent
Clerc et al.

(10) Patent No.: US 7,041,668 B2
(45) Date of Patent: May 9, 2006

(54) SUBSTITUTED BENZIMIDAZOLE COMPOUNDS AND THEIR USE FOR THE TREATMENT OF CANCER

(75) Inventors: Francois Clerc, Antony (FR); Francois Hamy, Illzach (FR); Isabelle Depaty, Paris (FR); Odile Angouillant-Boniface, Paris (FR); Stéphanie Deprets, Paris (FR); Chantal Carrez, Thais (FR); Manfred Roesner, Eppstein/Bremthal (FR)

(73) Assignee: Aventis Pharma S.A., Antony (FR)

( * ) Notice: Subject to any disclaimer, the term of this patent is extended or adjusted under 35 U.S.C. 154(b) by 138 days.

(21) Appl. No.: 10/808,889

(22) Filed: Mar. 25, 2004

(65) Prior Publication Data

US 2005/0014811 A1    Jan. 20, 2005

Related U.S. Application Data

(63) Continuation of application No. PCT/EP02/11353, filed on Sep. 26, 2002.

(30) Foreign Application Priority Data

Sep. 26, 2001    (EP)    .................................. 01402460

(51) Int. Cl.
| | |
|---|---|
| *C07D 235/04* | (2006.01) |
| *C07D 265/30* | (2006.01) |
| *C07D 231/10* | (2006.01) |
| *A61K 31/4168* | (2006.01) |
| *A61K 31/4184* | (2006.01) |

(52) U.S. Cl. .............................. 514/235.2; 514/254.09; 514/323; 514/388; 544/98; 544/373; 546/201; 546/277.4; 548/304.7; 548/209.1; 548/950; 549/505

(58) Field of Classification Search ............. 548/309.1, 548/304.7; 514/388
See application file for complete search history.

(56) References Cited

U.S. PATENT DOCUMENTS

| | | | | |
|---|---|---|---|---|
| 3,996,368 A | * | 12/1976 | Loewe et al. | ................ 514/388 |
| 4,639,463 A | * | 1/1987 | Rosner et al. | .............. 514/395 |
| 6,693,125 B1 | * | 2/2004 | Borisy et al. | ................ 514/388 |

FOREIGN PATENT DOCUMENTS

| | | |
|---|---|---|
| CA | 1069909 | 1/1980 |
| DE | DT 25 41 752 A1 | 3/1977 |
| EP | 0 115 039 A1 | 8/1984 |
| WO | 00/41669 | 7/2000 |

OTHER PUBLICATIONS

Davies T. G. et al, Inhibitor Binding to Active and Inactive CDK2: The Crystal Structure of CDK2-Cyclin A/Indirubin-5-Sulphonate, Structure, vol. 9, May, 2001, pp. 389-397.
Toogood Peter L, Cyclin-Dependent Kinase Inhibitors for Treating Cancer, Medicinal Research Reviews, vol. 21, No. 6, 2001, pp. 487-498.

* cited by examiner

*Primary Examiner*—Kamal A. Saeed
*Assistant Examiner*—Susannah E. Lee
(74) *Attorney, Agent, or Firm*—Balaram Gupta

(57) ABSTRACT

The present invention discloses and claims benzimidazole compounds of formula (I):

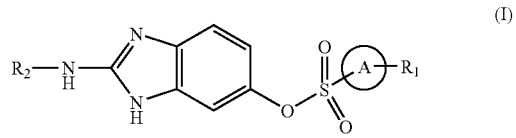

in which A is aryl or heteroaryl; $R_1$ is selected from optionally substituted alkyl, alkoxy, aryl or heteroaryl, NH-lower alkyl or NH-cycloalkyl, or halogen, $NH_2$; 1-imidazolyl or $SO_2Me$; $R_2$ is selected from optionally substituted —CO-alkyl, —CO-cycloalkyl, —CO-aralkyl, —CO-aryl, —CO-alkoxy, aryl or aralkyl, or —CO-amino, CO—$NHR_3$ or CO—$R_3R_4$ wherein $R_3$ and $R_4$ are selededed independently from hydrogen, alkyl, hydroxyalkyl, alkoxyalkyl, fluoroalkyl, alkynyl, heteroalkyl, alkylheteroalkyl, aryl, aralkyl or together form an alkylene chain optionally containing one to 4 heteroatoms; a pharmaceutically acceptable salt or a prodrug thereof; the use of compounds of formula (I) for the treatment of cancer, and pharmaceutical compositions comprising a compound of formula (I) and one or more pharmaceutically acceptable adjuvants or diluents.

16 Claims, No Drawings

SUBSTITUTED BENZIMIDAZOLE COMPOUNDS AND THEIR USE FOR THE TREATMENT OF CANCER

This application is a continuation of International Application No. PCT/EP02/11353 filed Sep. 26, 2002, which claims the benefit of priority of European Application No. 01 402 460.8, filed Sep. 26, 2001.

BACKGROUND OF THE INVENTION

1. Field of the Invention

The present invention relates to compounds useful for treating pathological states, which arise from or are exacerbated by cell proliferation, to pharmaceutical compositions comprising these compounds, and to methods of inhibiting cell proliferation in a mammal.

2. Description of the Art

Neoplastic diseases, characterized by the proliferation of cells, which are not subject to normal cell proliferating controls, are a major cause of death in humans and other mammals. Cancer chemotherapy has provided new and more effective drugs to treat these diseases and has also demonstrated that drugs, which are inhibitors of cyclin-dependent kinases are effective in inhibiting the proliferation of neoplastic cells.

Regulators at cell cycle checkpoints determine the decision for a cell to proceed through the cell cycle. Progression of the cell cycle is driven by cyclin-dependent kinases (CDKs) which are activated by oscillating members of the cycin family, resulting in substrate phosphorylation and ultimately cell division. In addition, endogenous inhibitors of CDKs (INK4 family and KIP/CIP family) negatively regulate the activity of CDKs. Normal cell growth is due to a balance between activators of CDKs (cyclins) and endogenous inhibitors of CDKs. In several types of cancer, aberrant expression or activity of several components of the cell cycle has been described.

Cdk4 functions in G1 phase of the cell cycle and is activated by D-type cyclins, which results in substrate phosphorylation and progression to S phase. The only known substrate for cdk4 is the retinoblastonia gene product (pRb), a major tumor suppressor gene product, which functions as a major checkpoint control in regulation of the G1/S phase transition. Hyperphosphorylation of pRb by CDKs causes the release of E2F (a family of transcription factors) bound to pRb which then activate genes necessary for cell cycle progression, e.g. thymidine kinase, thymdylate synthase, cyclin E and cyclin A. Cycin DI is amplified or overexpressed in many types of cancer (breast, ovarian, bladder, esophageal, lung, lymphoma), while the gene for p16, the endogenous inhibitor of cdk4, is deleted, mutated, or aberrantly methylated in many tumor types. A point of mutation in cdk4 was reported in a melanoma tumor that rendered the enzyme unable to bind p16 resulting in a constitutively active enzyme. All of the conditions described above lead to activation of cdk4 and cell cycle progression and tumor cell growth.

Arguments to designate CDK2 as an anticancer agent can be found in the literature <<Cyclin E activates Cdk2 which acts to phosphorylate pRb resulting in an irreversible commitment to cell division and transition into S-phase>> (P. L. Toogood, Medicinal Research Reviews (2001), 21(6); 487–498. and <<CDK2 (and possibly CDK3) is required for G1 progression and entry into S phase. In complex with cyclin E, it sustains pRb hyperphosphrylation to support progression through G1 and into S phase. In addition many other cellular targets of CDK2-CyclinE have been identified . . . . In complex with cyclinA, CDK2 plays a role in inactivating E2F and is required for completion of S phase.>> T. D. Davies et al. (2001) Structure 9, 389–397.

An added level of regulation of CDK activity exists. Cyclin-dependent kinase activating kinase (CAK) is a positive regulator of CDKs. CAK phosphorylates the catalytic CDKs on a conserved threonine residue to render the target enzyme completely active.

Because the defects in cell cycle molecules lead to CDK activation and subsequently cell cycle progression, it is logical that inhibition of CDK enzyme activity should block cell cycle progression and tumor cell growth.

The first CDK inhibitor to enter clinical trials is the compound known as flavopiridol. This compound is currently in Phase II clinical trials and is the only molecule in its class in the clinic at the present time. The aim of this invention is to produce molecules more active than flavopiridol.

It is known following publication of WO00/41669 that benzimidazole carbamate derivatives are vascular damaging agents that can be used for treating cancer, the sulfonic acid ester derivatives claimed in this patent application are not at all exemplified and their anticancerous way of action is not described. Our invention relates specifically to carbamates of those sulfonic acid ester derivatives.

SUMMARY OF THE INVENTION

In one embodiment of the present invention are disclosed compounds of formula (I)

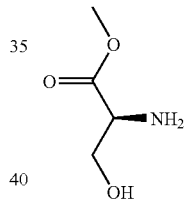

wherein A is an aryl or heteroaryl entity
wherein R₁ is selected from the group consisting of
  alkyl, eventually substituted by an alkoxy, heteroalkyl, aryl, acyl, acyl derivatives, halogen
  alkoxy eventually substituted by an alkyl, heteroalkyl, aryl, heteroaryl, alkoxyalkyl, hydroxyalkyl amide or a perfluoroalkoxy group or an alkylthio eventually substituted by an amide or a perfluoroalkylthio
  aryl or heteroaryl eventually substituted by one or more alkyl group, alkoxy group, nitro group, cyano group, acyl derivative, perfluoroalkoxy group, perfluoroalkyl group, heteroaryl group, aryloxy group
  halogen
  4 NH₂
  4 NH alkyl or cycloalkyl eventually substituted with an an acyl, an acyl derivative, an hydroxy, an amino, alkoxy, heterocyclyl or aryl group
  4 N imidazolyl
  3 SO₂Me when A is phenyl
wherein R2 is selected from the group consisting of
  CO-alkyl eventually substituted by amino, acid, acid derivative, alkoxy, aryl or OH groups
  CO-aralkyl eventually substituted by alkoxy, halogeno, amino, acid or acid derivatives
  CO-aryl eventually substituted CO-alkoxy eventually substituted by aryl CO-amino, CO—NHR$_3$, CO—NR$_3$R$_4$ wherein R$_3$ and R$_4$ are selected independently from hydrogen, alkyl, hydroxyalkyl, alkoxyalkyl, fluoroalkyl, alkynyl, heteroalkyl, alkylheteroalkyl, aryl, aralkyl or together form an alkylen chain including eventually one to 4 more heteroatoms aryl or aralkyl eventually substituted by heterocycloalkyl, alkyl, aryl, alkoxy, amino, fluoroalkyl, acyl derivatives, halogen or a pharmaceutically acceptable salt.

Among the preferred compounds of formula (I) are those where A represents a phenyl, thiophene, isoxazole, oxazole, pyrazole, furan, or pyridine, and more preferably those where A is a phenyl group.

Among the preferred compounds of formula (I) are those wherein the aryl, aralkyl, heteroaryl or heteroarylalkyl are optionally substituted with one or more similar or different groups selected from halogen, alkoxy, alkyl, hydroxyalkyl, alkylthio, amino, mono or dialkylamino, heterocyclylamino, arylamino, heteroarylamino, heteroaryl, nitro, heterocycloalkyl, perfluoroalkyl, perfluroroalkoxy, perfluoroalkylthio, acyl derivatives.

Among the preferred compounds of formula (I) are those wherein R$_2$ is an aminocarbonyl group substituted by a substituent selected from monoalkylamino or a monoarylamino sutstituent. In the preferred compounds of formula (I) are those containing for R$_2$ an amino substituent and preferably a monoalkylamino or a monoarylamino substituent and still more preferably those containing a monoalkylamino substituent with an acyl derivative.

Among the alkyl or alkylene substituents which are substituted are included those substituted with one or more amino, aminoalkyl, aminoalkylamino, hydroxy, alkoxy, hydroxyalkoxy, acyl, acyl derivatives, alkyl, heteroalkyl, arylalkyl, arylamino, aryloxy, or aryl groups.

Among the alkoxy or alkythio substituents are included the alkoxy or alkylthio groups substituted with one or more amino, acyl, acyl derivatives, alkyl, arylalkyl or aryl groups.

Among the acyl groups or acyl derivatives groups are included the carboxylic acids and the sulfonic acids, the derivatives of which being mainly ester or carbamoyl esters.

The alkyl chain of the present invention includes linear, branched or cyclic chain containing 1 to 10 carbon atoms. The alkoxy chain of the present invention includes linear, branched or cyclic chains containing 1 to 4 carbon atoms. The aryl groups include phenyl or naphthyl groups, heteroaryl groups containing one to four heteroatoms selected from S, N or O such as furanyl, thiophenyl, isoxazolyl, oxazolyl, pyrazolyl and pyridinyl. The heterocyclyl group contains one to four heteroatoms chosen from N, O, S and 2 to 6 carbon atoms.

Among the preferred compounds are those containing an alkyl chain 1 to 10 carbon atoms and those containing a cycloalkyl chain 3 to 5 carbon atoms. When the alkyl chain is substituted by an alkoxy group this last group has preferably one carbon atom.

Among the compounds of formula (I) the following compounds are much more preferred:

Methyl-5-(4-[2-hydroxyethyl]aminophenylsulfonyloxy)benzimidazole-2-carbamate

Methyl-5-(4-[4-hydroxbutyl]aminophenylsulfonyloxy)benzimidazole-2-carbamate

Methyl-5-(4-[2-methoxyethyl]aminophenylsulfonyloxy)benzimidazole-2-carbamate

Methyl-5-(4-[1-imidazolyl]-phenylsulfonyloxy)benzimidazole-2-carbamate

Methyl-5-(4-[2-pyridylmethyl]aminophenylsulfonyloxy)benzimidazole-2-carbamate

Methyl-5-(4-ethylaminophenylsulfonyloxy)benzimidazole-2-carbamate

Methyl-5-(4-[N-glycinyl]-phenylsulfonyloxy)benzimidazole-2-carbamate

Methyl-5-(4-[1-methyl,2-hydroxyethyl]aminophenylsulfonyloxy)benzimidazole-2-carbamate Methyl-5-(4-[2-methyl,2-hydroxyethyl]aminophenylsulfonyloxy)benzimidazole-2-carbamate Methyl-5-(4-isopropylaminophenylsulfonyloxy)benzimidazole-2-carbamate Methyl-5-(4-[1-ethyl 2-hydroxyethyl]aminophenylsulfonyloxy)benzimidazole-2-carbamate Methyl-5-(4-butylaminophenylsulfonyloxy)benzimidazole-2-carbamate Methyl-5-(4-[3-methoxypropyl]aminophenylsulfonyloxy)benzimidazole-2-carbamate Methyl-5-(4-methylaminophenylsulfonyloxy)benzimidazole-2-carbamate Methyl-5-(4-[2-sulfonylethyl]aminophenylsulfonyloxy)benzimidazole-2-carbamate Methyl-5-(4-aminophenylsulfonyloxy)benzimidazole-2-carbamate Methyl-5-(4-[2-diethylaminoethyl]aminophenylsulfonyloxy)benzimidazole-2-carbamate Methyl-5-(4-[1-tetrathydrofurylmethyl]aminophenylsulfonyloxy)benzimidazole-2-carbamate Methyl-5-(4-cyclopentylaminophenylsulfonyloxy)benzimidazole-2-carbamate Methyl-5-(4-[2-phenylethyl]aminophenylsulfonyloxy)benzimidazole-2-carbamate N-[5-(4-[imidazolyl]-phenylsulfonyloxy)-1H-benzimidazole-2-yl]-methylurea N-[5-(4-cyclopentylaminophenylsulfonyloxy)-1H-benzimidazole-2-yl]-methylurea N-[5-(4-cyclopentylaminophenylsulfonyloxy)-1H-benzimidazole-2-yl]-dimethylurea 4-Imidazol-1-yl-benzenesulfonic acid 2-benzoylamino-1H-benzoimidazol-5-yl ester 4-Imidazol-1-yl-benzenesulfonic acid 2-phenylacetylamino-1H-benzoimidazol-5-yl ester 4-Imidazol-1-yl-benzenesulfonic acid 2-(2-tert-butoxycarbonylamino-acetylamino)-1H-benzoimidazol-5-yl ester N-[5-(4-Imidazol-1-yl-benzenesulfonyloxy)-1H-benzoimidazol-2-yl]-succinamic acid methyl ester 4-[5-(4-Imidazol-1-yl-benzenesulfonyloxy)-1H-benzoimidazol-2-ylcarbamoyl]-butyric acid methyl ester 4-[5-(4-Imidazol-1-yl-benzenesulfonyloxy)-1H-benzoimidazol-2-ylcarbamoyl]-butyric acid methyl ester 4-Imidazol-1-yl-benzenesulfonic acid 2-(cyclohexanecarbonyl-amino)-1H-benzoimidazol-5-yl ester 4-Imidazol-1-yl-benzenesulfonic acid 2-[(pyridine-2-carbonyl)-amino]-1H-benzoimidazol-5-yl ester 4-Imidazol-1-yl-benzenesulfonic acid 2-[(pyridine-3-carbonyl)-amino]-1H-benzoimidazol-5-yl ester 4-Imidazol-1-yl-benzenesulfonic acid 2-[(pyridine-4-carbonyl)-amino]-1H-benzoimidazol-5-yl ester 4-Imidazol-1-yl-benzenesulfonic acid 2-pentanoylamino-1H-benzoimidazol-5-yl ester 4-Imidazol-1-yl-benzenesulfonic acid 2-hexanoylamino-1H-benzoimidazol-5-yl ester 4-Imidazol-1-yl-benzenesulfonic acid 2-(2-cyclopropylacetylamino)-1H-benzoimidazol-5-yl ester 4-Imidazol-1-yl-benzenesulfonic acid 2-(2-cyclohexyl-acetylamino)-1H-benzoimidazol-5-yl ester
4-Imidazol-1-yl-benzenesulfonic acid 2-(2-methoxy-acetylamino)-1H-benzoimidazol-5-yl ester
4-Imidazol-1-yl-benzenesulfonic acid 2-(2-dimethylamino-acetylamino)-1H-benzoimidazol-5-yl ester
4-Cyclopentylamino-benzenesulfonic acid 2-benzoylamino-1H-benzoimidazol-5-yl ester
4-Cyclopentylamino-benzenesulfonic acid 2-phenylacetylamino-1H-benzoimidazol-5-yl ester
4-Cyclopentylamino-benzenesulfonic acid 2-(2-tert-butoxycarbonylamino-acetylamino)-1H-benzoimidazol-5-yl ester
N-[5-(4-Cyclopentylamino-benzenesulfonyloxy)-1H-benzoimidazol-2-yl]-succinamic acid methyl ester
4-[5-(4-Cyclopentylamino-benzenesulfonyloxy)-1H-benzoimidazol-2-ylcarbamoyl]-butyric acid methyl ester
4-Cyclopentylamino-benzenesulfonic acid 2-(cyclopropanecarbonyl-amino)-1H-benzoimidazol-5-yl ester
4-Cyclopentylamino-benzenesulfonic acid 2-(cyclohexanecarbonyl-amino)-1H-benzoimidazol-5-yl ester
4-Cyclopentylamino-benzenesulfonic acid 2-[(pyridine-2-carbonyl)-amino]-1H-benzoimidazol-5-yl ester
4-Cyclopentylamino-benzenesulfonic acid 2-[(pyridine-4-carbonyl)-amino]-1H-benzoimidazol-5-yl ester
4-Cyclopentylamino-benzenesulfonic acid 2-[(pyridine-4-carbonyl)-amino]-1H-benzoimidazol-5-yl ester
4-Cyclopentylamino-benzenesulfonic acid 2-pentanoylamino-1H-benzoimidazol-5-yl ester
4-Cyclopentylamino-benzenesulfonic acid 2-hexanoylamino-1H-benzoimidazol-5-yl ester
4-Cyclopentylamino-benzenesulfonic acid 2-(2-cyclopropyl-acetylamino)-1H-benzoimidazol-5-yl ester
4-Cyclopentylamino-benzenesulfonic acid 2-(2-cyclohexyl-acetylamino)-1H-benzoimidazol-5-yl ester
4-Cyclopentylamino-benzenesulfonic acid 2-(2-methoxy-acetylamino)-1H-benzoimidazol-5-yl ester
4-Cyclopentylamino-benzenesulfonic acid 2-(2-dimethylamino-acetylamino)-1H-benzoimidazol-5-yl ester
4-Imidazol-1-yl-benzenesulfonic acid 2-(3-cyclopropyl-ureido)-1H-benzoimidazol-5-yl ester
4-Cyclopentylamino-benzenesulfonic acid 2-(3-cyclopropyl-ureido)-1H-benzoimidazol-5-yl ester
4-Imidazol-1-yl-benzenesulfonic acid 2-(3-isopropyl-ureido)-1H-benzoimidazol-5-yl ester
4-Cyclopentylamino-benzenesulfonic acid 2-(3-isopropyl-ureido)-1H-benzoimidazol-5-yl ester
4-Imidazol-1-yl-benzenesulfonic acid 2-(3-butyl-ureido)-1H-benzoimidazol-5-yl ester
4-Cyclopentylamino-benzenesulfonic acid 2-(3-butyl-ureido)-1H-benzoimidazol-5-yl ester
4-Imidazol-1-yl-benzenesulfonic acid 2-[3-(2-fluoro-phenyl)-ureido]-1H-benzoimidazol-5-yl ester
4-Cyclopentylamino-benzenesulfonic acid 2-[3-(2-fluoro-phenyl)-ureido]-1H-benzoimidazol-5-yl ester
4-Imidazol-1-yl-benzenesulfonic acid 2-[3-(2-methoxy-phenyl)-ureido]-1H-benzoimidazol-5-yl ester
4-Cyclopentylamino-benzenesulfonic acid 2-[3-(2-methoxy-phenyl)-ureido]-1H-benzoimidazol-5-yl ester
4-Imidazol-1-yl-benzenesulfonic acid 2-[3-(3-methoxy-phenyl)-ureido]-1H-benzoimidazol-5-yl ester
4-Cyclopentylamino-benzenesulfonic acid 2-[3-(3-methoxy-phenyl)-ureido]-1H-benzoimidazol-5-yl ester
4-Imidazol-1-yl-benzenesulfonic acid 2-[3-(4-methoxy-phenyl)-ureido]-1H-benzoimidazol-5-yl ester
4-Cyclopentylamino-benzenesulfonic acid 2-[3-(4-methoxy-phenyl)-ureido]-1H-benzoimidazol-5-yl ester
4-Imidazol-1-yl-benzenesulfonic acid 2-[3-(2-chloro-phenyl)-ureido]-1H-benzoimidazol-5-yl ester
4-Cyclopentylamino-benzenesulfonic acid 2-[3-(2-chloro-phenyl)-ureido]-1H-benzoimidazol-5-yl ester
4-Imidazol-1-yl-benzenesulfonic acid 2-[3-(4-chloro-phenyl)-ureido]-1H-benzoimidazol-5-yl ester
4-Cyclopentylamino-benzenesulfonic acid 2-[3-(4-chloro-phenyl)-ureido]-1H-benzoimidazol-5-yl ester
4-Imidazol-1-yl-benzenesulfonic acid 2-[3-(2-methoxy-benzyl)-ureido]-1H-benzoimidazol-5-yl ester
4-Cyclopentylamino-benzenesulfonic acid 2-[3-(2-methoxy-benzyl)-ureido]-1H-benzoimidazol-5-yl ester
4-Cyclopentylamino-benzenesulfonic acid 2-[3-(3-fluoro-benzyl)-ureido]-1H-benzoimidazol-5-yl ester
4-Imidazol-1-yl-benzenesulfonic acid 2-[3-(3-chloro-phenyl)-ureido]-1H-benzoimidazol-5-yl ester
4-Cyclopentylamino-benzenesulfonic acid 2-[3-(3-chloro-phenyl)-ureido]-1H-benzoimidazol-5-yl ester
4-Imidazol-1-yl-benzenesulfonic acid 2-(3-isobutyl-ureido)-1H-benzoimidazol-5-yl ester
4-Cyclopentylamino-benzenesulfonic acid 2-(3-isobutyl-ureido)-1H-benzoimidazol-5-yl ester
4-Imidazol-1-yl-benzenesulfonic acid 2-[3-(2-dimethylamino-ethyl)-ureido]-1H-benzoimidazol-5-yl ester
4-Cyclopentylamino-benzenesulfonic acid 2-[3-(2-dimethylamino-ethyl)-ureido]-1H-benzoimidazol-5-yl ester
4-Imidazol-1-yl-benzenesulfonic acid 2-(3-ethyl-ureido)-1H-benzoimidazol-5-yl ester
4-Cyclopentylamino-benzenesulfonic acid 2-(3-ethyl-ureido)-1H-benzoimidazol-5-yl ester
{3-[5-(4-Cyclopentylamino-benzenesulfonyloxy)-1H-benzoimidazol-2-yl]-ureido}-acetic acid
4-Imidazol-1-yl-benzenesulfonic acid 2-[3-(2-sulfo-ethyl)-ureido]-1H-benzoimidazol-5-yl ester
4-Imidazol-1-yl-benzenesulfonic acid 2-[3-(2-methoxy-ethyl)-ureido]-1H-benzoimidazol-5-yl ester
4-Cyclopentylamino-benzenesulfonic acid 2-[3-(2-methoxy-ethyl)-ureido]-1H-benzoimidazol-5-yl ester
4-Imidazol-1-yl-benzenesulfonic acid 2-[3-(4-dimethylamino-phenyl)-ureido]-1H-benzoimidazol-5-yl ester
4-Cyclopentylamino-benzenesulfonic acid 2-[3-(4-dimethylamino-phenyl)-ureido]-1H-benzoimidazol-5-yl ester
4-Imidazol-1-yl-benzenesulfonic acid 2-(3-pyridin-2-ylmethyl-ureido)-1H-benzoimidazol-5-yl ester
4-Cyclopentylamino-benzenesulfonic acid 2-(3-pyridin-2-ylmethyl-ureido)-1H-benzoimidazol-5-yl ester
4-Imidazol-1-yl-benzenesulfonic acid 2-(3-cyclobutyl-ureido)-1H-benzoimidazol-5-yl ester
4-Cyclopentylamino-benzenesulfonic acid 2-(3-cyclobutyl-ureido)-1H-benzoimidazol-5-yl ester
4-Imidazol-1-yl-benzenesulfonic acid 2-(3-pyridin-4-ylmethyl-ureido)-1H-benzoimidazol-5-yl ester
4-Cyclopentylamino-benzenesulfonic acid 2-(3-pyridin-4-ylmethyl-ureido)-1H-benzoimidazol-5-yl ester
4-Imidazol-1-yl-benzenesulfonic acid 2-(3-tert-butyl-ureido)-1H-benzoimidazol-5-yl ester
4-Cyclopentylamino-benzenesulfonic acid 2-(3-tert-butyl-ureido)-1H-benzoimidazol-5-yl ester
4-Imidazol-1-yl-benzenesulfonic acid 2-(3-phenyl-ureido)-1H-benzoimidazol-5-yl ester
4-Cyclopentylamino-benzenesulfonic acid 2-(3-phenyl-ureido)-1H-benzoimidazol-5-yl ester
4-Imidazol-1-yl-benzenesulfonic acid 2-(3-cyclohexyl-ureido)-1H-benzoimidazol-5-yl ester
4-Cyclopentylamino-benzenesulfonic acid 2-(3-cyclohexyl-ureido)-1H-benzoimidazol-5-yl ester;

4-Imidazol-1-yl-benzenesulfonic acid 2-(3-cyclopentyl-ureido)-1H-benzoimidazol-5-yl ester
4-Imidazol-1-yl-benzenesulfonic acid 2-[3-(3-fluoro-phenyl)-ureido]-1H-benzoimidazol-5-yl ester
4-Cyclopentylamino-benzenesulfonic acid 2-[3-(3-fluoro-phenyl)-ureido]-1H-benzoimidazol-5-yl ester
4-Cyclopentylamino-benzenesulfonic acid 2-[3-(2-hydroxy-ethyl)-ureido]-1H-benzoimidazol-5-yl ester
4-Imidazol-1-yl-benzenesulfonic acid 2-[3-(2-hydroxy-ethyl)-ureido]-1H-benzoimidazol-5-yl ester
4-Imidazol-1-yl-benzenesulfonic acid 2-[3-(4-fluoro-phenyl)-ureido]-1H-benzoimidazol-5-yl ester
4-Cyclopentylamino-benzenesulfonic acid 2-[3-(4-fluoro-phenyl)-ureido]-1H-benzoimidazol-5-yl ester
4-Imidazol-1-yl-benzenesulfonic acid 2-[3-(2-chloro-benzyl)-ureido]-1H-benzoimidazol-5-yl ester
4-Cyclopentylamino-benzenesulfonic acid 2-[3-(2-chloro-benzyl)-ureido]-1H-benzoimidazol-5-yl ester
4-Imidazol-1-yl-benzenesulfonic acid 2-[3-(2-fluoro-benzyl)-ureido]-1H-benzoimidazol-5-yl ester
4-Cyclopentylamino-benzenesulfonic acid 2-[3-(2-fluoro-benzyl)-ureido]-1H-benzoimidazol-5-yl ester
4-Imidazol-1-yl-benzenesulfonic acid 2-[(azetidine-1-carbonyl)-amino]-1H-benzoimidazol-5-yl ester
4-Cyclopentylamino-benzenesulfonic acid 2-[(azetidine-1-carbonyl)-amino]-1H-benzoimidazol-5-yl ester
4-Imidazol-1-yl-benzenesulfonic acid 2-(3-pyridin-3-ylmethyl-ureido)-1H-benzoimidazol-5-yl ester
4-Cyclopentylamino-benzenesulfonic acid 2-(3-pyridin-3-ylmethyl-ureido)-1H-benzoimidazol-5-yl ester
4-Imidazol-1-yl-benzenesulfonic acid 2-{3-[3-(4-methyl-piperazin-1-yl)-propyl]-ureido}-1H-benzoimidazol-5-yl ester
4-Cyclopentylamino-benzenesulfonic acid 2-{3-[3-(4-methyl-piperazin-1-yl)-propyl]-ureido}-1H-benzoimidazol-5-yl ester
4-Imidazol-1-yl-benzenesulfonic acid 2-(3-benzyl-ureido)-1H-benzoimidazol-5-yl ester
4-Cyclopentylamino-benzenesulfonic acid 2-(3-benzyl-ureido)-1H-benzoimidazol-5-yl ester
4-{3-[5-(4-Cyclopentylamino-benzenesulfonyloxy)-1H-benzoimidazol-2-yl]-ureido}-butyric acid methyl ester;
4-{3-[5-(4-Cyclopentylamino-benzenesulfonyloxy)-1H-benzoimidazol-2-yl]-ureido}-butyric acid ethyl ester
4-{3-[5-(4-Cyclopentylamino-benzenesulfonyloxy)-1H-benzoimidazol-2-yl]-ureido}-acetic acid methyl ester
4-Cyclopentylamino-benzenesulfonic acid 2-[3-(3-imidazol-1-yl-propyl)-ureido]-1H-benzoimidazol-5-yl ester
1-[5-(4-Cyclopentylamino-benzenesulfonyloxy)-1H-benzoimidazol-2S-ylcarbamoyl]-pyrrolidine-2-carboxylic acid
1-[5-(4-Cyclopentylamino-benzenesulfonyloxy)-1H-benzoimidazol-2S-ylcarbamoyl]-pyrrolidine-2-carboxylic acid methyl ester
4-Cyclopentylamino-benzenesulfonic acid 2-(3-carbamoylmethyl-ureido)-1H-benzoimidazol-5-yl ester
1-[5-(4-Cyclopentylamino-benzenesulfonyloxy)-1H-benzoimidazol-2-ylcarbamoyl]-piperidine-4-carboxylic acid ethyl ester
4-Cyclopentylamino-benzenesulfonic acid 2-(3-piperidin-4-ylmethyl-ureido)-1H-benzoimidazol-5-yl ester
4-Cyclopentylamino-benzenesulfonic acid 2-[3-(2-morpholin-4-yl-ethyl)-ureido]-1H-benzoimidazol-5-yl ester
4-Cyclopentylamino-benzenesulfonic acid 2-[3-(2-amino-2-methyl-propyl)-ureido]-1H-benzoimidazol-5-yl ester;
4-Cyclopentylamino-benzenesulfonic acid 2-[3-(4-hydroxy-cyclohexyl)-ureido]-1H-benzoimidazol-5-yl ester
4-Cyclopentylamino-benzenesulfonic acid 2-[3-(3-hydroxy-propyl)-ureido]-1H-benzoimidazol-5-yl ester
4-Cyclopentylamino-benzenesulfonic acid 2-[3-(1,1-dimethyl-propyl)-ureido]-1H-benzoimidazol-5-yl ester
4-Cyclopentylamino-benzenesulfonic acid 2-{3-[2-(2-hydroxy-ethylamino)-ethyl]-ureido}-1H-benzoimidazol-5-yl ester
4-Cyclopentylamino-benzenesulfonic acid 2-[3-(4-hydroxy-butyl)-ureido]-1H-benzoimidazol-5-yl ester
4-Cyclopentylamino-benzenesulfonic acid 2-{3-[3-(2-oxo-pyrrolidin-1-yl)-propyl]-ureido}-1H-benzoimidazol-5-yl ester
4-Cyclopentylamino-benzenesulfonic acid 2-[3-(2-carbamoyl-ethyl)-ureido]-1H-benzoimidazol-5-yl ester
4-Cyclopentylamino-benzenesulfonic acid 2-[(2S-carbamoyl-pyrrolidine-1-carbonyl)-amino]-1H-benzoimidazol-5-yl ester
4-Cyclopentylamino-benzenesulfonic acid 2-{3-[2-(2-hydroxy-ethoxy)-ethyl]-ureido}-1H-benzoimidazol-5-yl ester
4-Cyclopentylamino-benzenesulfonic acid 2-[3-(3-pyrrolidin-1-yl-propyl)-ureido]-1H-benzoimidazol-5-yl ester
4-Cyclopentylamino-benzenesulfonic acid 2-[3-(1-ethyl-pyrrolidin-2-ylmethyl)-ureido]-1H-benzoimidazol-5-yl ester
4-Cyclopentylamino-benzenesulfonic acid 2-[3-(2-pyrrolidin-1-yl-ethyl)-ureido]-1H-benzoimidazol-5-yl ester
4-Cyclopentylamino-benzenesulfonic acid 2-[3-(2-piperidin-1-yl-ethyl)-ureido]-1H-benzoimidazol-5-yl ester
4-Cyclopentylamino-benzenesulfonic acid 2-[3-(2-hydroxy-1-methyl-ethyl)-ureido]-1H-benzoimidazol-5-yl ester
4-Cyclopentylamino-benzenesulfonic acid 2-[3-(2-isopropylamino-ethyl)-ureido]-1H-benzoimidazol-5-yl ester
4-Cyclopentylamino-benzenesulfonic acid 2-[3-(2-diethylamino-ethyl)-ureido]-1H-benzoimidazol-5-yl ester
2-{3-[5-(4-Cyclopentylamino-benzenesulfonyloxy)-1H-benzoimidazol-2-yl]-ureido}-3S-hydroxy-propionic acid methyl ester
4-{3-[5-(4-Imidazol-1-yl-benzenesulfonyloxy)-1H-benzoimidazol-2-yl]-ureido}-butyric acid methyl ester
4-{3-[5-(4-Imidazol-1-yl-benzenesulfonyloxy)-1H-benzoimidazol-2-yl]-ureido}-butyric acid ethyl ester
{3-[5-(4-Imidazol-1-yl-benzenesulfonyloxy)-1H-benzoimidazol-2-yl]-ureido}-acetic acid methyl ester
4-Imidazol-1-yl-benzenesulfonic acid 2-[3-(3-imidazol-1-yl-propyl)-ureido]-1H-benzoimidazol-5-yl ester
1-[5-(4-Imidazol-1-yl-benzenesulfonyloxy)-1H-benzoimidazol-2-ylcarbamoyl]-pyrrolidine-2-carboxylic acid
1-[5-(4-Imidazol-1-yl-benzenesulfonyloxy)-1H-benzoimidazol-2-ylcarbamoyl]-pyrrolidine-2-carboxylic acid methyl ester
4-Imidazol-1-yl-benzenesulfonic acid 2-(3-carbamoylmethyl-ureido)-1H-benzoimidazol-5-yl ester
1-[5-(4-Imidazol-1-yl-benzenesulfonyloxy)-1H-benzoimidazol-2-ylcarbamoyl]-piperidine-4-carboxylic acid ethyl ester
4-Imidazol-1-yl-benzenesulfonic acid 2-(3-piperidin-4-ylmethyl-ureido)-1H-benzoimidazol-5-yl ester
4-Imidazol-1-yl-benzenesulfonic acid 2-[3-(2-morpholin-4-yl-ethyl)-ureido]-1H-benzoimidazol-5-yl ester
4-Imidazol-1-yl-benzenesulfonic acid 2-[3-(2-amino-2-methyl-propyl)-ureido]-1H-benzoimidazol-5-yl ester
4-Imidazol-1-yl-benzenesulfonic acid 2-[3-(4-hydroxy-cyclohexyl)-ureido]-1H-benzoimidazol-5-yl ester
4-Imidazol-1-yl-benzenesulfonic acid 2-[3-(3-hydroxy-propyl)-ureido]-1H-benzoimidazol-5-yl ester 4-Imidazol-1-yl-benzenesulfonic acid 2-[3-(1,1-dimethyl-propyl)-ureido]-1H-benzoimidazol-5-yl ester 4-Imidazol-1-yl-benzenesulfonic acid 2-{3-[2-(2-hydroxy-ethylamino)-ethyl]-ureido}-1H-benzoimidazol-5-yl ester 4-Imidazol-1-yl-benzenesulfonic acid 2-[3-(4-hydroxy-butyl)-ureido]-1H-benzoimidazol-5-yl ester 4-Imidazol-1-yl-benzenesulfonic acid 2-{3-[3-(2-oxo-pyrrolidin-1-yl)-propyl]-ureido}-1H-benzoimidazol-5-yl ester 4-Imidazol-1-yl-benzenesulfonic acid 2-[3-(2-carbamoyl-ethyl)-ureido]-1H-benzoimidazol-5-yl ester 4-Imidazol-1-yl-benzenesulfonic acid 2-[3-(1,1-dimethyl-propyl)-ureido]-1H-benzoimidazol-5-yl ester 4-Imidazol-1-yl-benzenesulfonic acid 2-[(2-carbamoyl-pyrrolidine-1-carbonyl)-amino]-1H-benzoimidazol-5-yl ester 4-Imidazol-1-yl-benzenesulfonic acid 2-{3-[2-(2-hydroxyethoxy)-ethyl]-ureido}-1H-benzoimidazol-5-yl ester 4-Imidazol-1-yl-benzenesulfonic acid 2-[3-(3-pyrrolidin-1-yl-propyl)-ureido]-1H-benzoimidazol-5-yl ester 4-Imidazol-1-yl-benzenesulfonic acid 2-[3-(1-ethyl-pyrrolidin-2-ylmethyl)-ureido]-1H-benzoimidazol-5-yl ester 4-Imidazol-1-yl-benzenesulfonic acid 2-[3-(2-pyrrolidin-1-yl-ethyl)-ureido]-1H-benzoimidazol-5-yl ester 4-Imidazol-1-yl-benzenesulfonic acid 2-[3-(2-piperidin-1-yl-ethyl)-ureido]-1H-benzoimidazol-5-yl ester 4-Imidazol-1-yl-benzenesulfonic acid 2-[3-(2-hydroxy-1-methyl-ethyl)-ureido]-1H-benzoimidazol-5-yl ester 4-Imidazol-1-yl-benzenesulfonic acid 2-[3-(2-isopropylamino-ethyl)-ureido]-1H-benzoimidazol-5-yl ester 4-Imidazol-1-yl-benzenesulfonic acid 2-[3-(2-diethylamino-ethyl)-ureido]-1H-benzoimidazol-5-yl ester 2-{3-[5-(4-Imidazol-1-yl-benzenesulfonyloxy)-1H-benzoimidazol-2-yl]-ureido}-3-hydroxy-propionic acid methyl ester 4-[(Tetrahydro-furan-2-ylmethyl)-amino]-benzenesulfonic acid 2-(3-carbamoylmethyl-ureido)-1H-benzoimidazol-5-yl ester 4-[(Tetrahydro-furan-2-ylmethyl)-amino]-benzenesulfonic acid 2-[3-(2-hydroxy-ethyl)-ureido]-1H-benzoimidazol-5-yl ester 4-[(Tetrahydro-furan-2-ylmethyl)-amino]-benzenesulfonic acid 2-[3-(3-hydroxy-propyl)-ureido]-1H-benzoimidazol-5-yl ester 4-[(Tetrahydro-furan-2-ylmethyl)-amino]-benzenesulfonic acid 2-[3-(4-hydroxy-butyl)-ureido]-1H-benzoimidazol-5-yl ester 4-[(Tetrahydro-furan-2-ylmethyl)-amino]-benzenesulfonic acid 2-[3-(2-methoxy-1-methyl-ethyl)-ureido]-1H-benzoimidazol-5-yl ester 4-[(Tetrahydro-furan-2-ylmethyl)-amino]-benzenesulfonic acid 2-[3-(1-ethyl-pyrrolidin-2-ylmethyl)-ureido]-1H-benzoimidazol-5-yl ester 4-[(Tetrahydro-furan-2-ylmethyl)-amino]-benzenesulfonic acid 2-[3-(2-pyrrolidin-1-yl-ethyl)-ureido]-1H-benzoimidazol-5-yl ester 4-[(Tetrahydro-furan-2-ylmethyl)-amino]-benzenesulfonic acid 2-[3-(3-pyrrolidin-1-yl-propyl)-ureido]-1H-benzoimidazol-5-yl ester 4-[(Tetrahydro-furan-2-ylmethyl)-amino]-benzenesulfonic acid 2-[3-(2-morpholin-4-yl-ethyl)-ureido]-1H-benzoimidazol-5-yl ester 4-[(Tetrahydro-furan-2-ylmethyl)-amino]-benzenesulfonic acid 2-(3-ethyl-ureido)-1H-benzoimidazol-5-yl ester 4-[(Tetrahydro-furan-2-ylmethyl)-amino]-benzenesulfonic acid 2-(3-methyl-ureido)-1H-benzoimidazol-5-yl ester 4-[(Tetrahydro-furan-2-ylmethyl)-amino]-benzenesulfonic acid 2-(3-pyridin-2-ylmethyl-ureido)-1H-benzoimidazol-5-yl ester 4-[(Tetrahydro-furan-2-ylmethyl)-amino]-benzenesulfonic acid 2-(3-pyridin-3-ylmethyl-ureido)-1H-benzoimidazol-5-yl ester 4-[(Tetrahydro-furan-2-ylmethyl)-amino]-benzenesulfonic acid 2-{3-[3-(4-methyl-piperazin-1-yl)-propyl]-ureido}-1H-benzoimidazol-5-yl ester 4-[(Tetrahydro-furan-2-ylmethyl)-amino]-benzenesulfonic acid 2-[3-(2-sulfo-ethyl)-ureido]-1H-benzoimidazol-5-yl ester 4-[(Tetrahydro-furan-2-ylmethyl)-amino]-benzenesulfonic acid 2-(3-cyclobutyl-ureido)-1H-benzoimidazol-5-yl ester 4-[(Tetrahydro-furan-2-ylmethyl)-amino]-benzenesulfonic acid 2-{3-[3-(2-oxo-pyrrolidin-1-yl)-propyl]-ureido}-1H-benzoimidazol-5-yl ester 4-[(Tetrahydro-furan-2-ylmethyl)-amino]-benzenesulfonic acid 2-{3-[2-(2-hydroxy-ethylamino)-ethyl]-ureido}-1H-benzoimidazol-5-yl ester 4-[(Tetrahydro-furan-2-ylmethyl)-amino]-benzenesulfonic acid 2-[3-(2-piperidin-1-yl-ethyl)-ureido]-1H-benzoimidazol-5-yl ester 4-Benzylamino-benzenesulfonic acid 2-(cyclopropanecarbonyl-amino)-1H-benzoimidazol-5-yl ester 4-Methylamino-benzenesulfonic acid 2-(cyclopropanecarbonyl-amino)-1H-benzoimidazol-5-yl ester 4-(2-Hydroxy-ethylamino)-benzenesulfonic acid 2-(cyclopropanecarbonyl-amino)-1H-benzoimidazol-5-yl ester 4-(3-Hydroxy-propylamino)-benzenesulfonic acid 2-(cyclopropanecarbonyl-amino)-1H-benzoimidazol-5-yl ester 4-(4-Hydroxy-butylamino)-benzenesulfonic acid 2-(cyclopropanecarbonyl-amino)-1H-benzoimidazol-5-yl ester 4-(2-Methoxy-1-methyl-ethylamino)-benzenesulfonic acid 2-(cyclopropanecarbonyl-amino)-1H-benzoimidazol-5-yl ester 4-(2-Pyrrolidin-1-yl-ethylamino)-benzenesulfonic acid 2-(cyclopropanecarbonyl-amino)-1H-benzoimidazol-5-yl ester 4-(1-Hydroxymethyl-propylamino)-benzenesulfonic acid 2-(cyclopropanecarbonyl-amino)-1H-benzoimidazol-5-yl ester 4-(2-Hydroxy-1-methyl-ethylamino)-benzenesulfonic acid 2-(cyclopropanecarbonyl-amino)-1H-benzoimidazol-5-yl ester 4-(2-Piperidin-1-yl-ethylamino)-benzenesulfonic acid 2-(cyclopropanecarbonyl-amino)-1H-benzoimidazol-5-yl ester 4-(3-Pyrrolidin-1-yl-propylamino)-benzenesulfonic acid 2-(cyclopropanecarbonyl-amino)-1H-benzoimidazol-5-yl ester 4-(3-Hydroxy-2,2-dimethyl-propylamino)-benzenesulfonic acid 2-(cyclopropane-carbonyl-amino)-1H-benzoimidazol-5-yl ester 4-[(Pyridin-3-ylmethyl)-amino]-benzenesulfonic acid 2-(cyclopropanecarbonyl-amino)-1H-benzoimidazol-5-yl ester 4-[3-(4-Methyl-piperazin-1-yl)-propylamino]-benzenesulfonic acid 2-(cyclopropane-carbonyl-amino)-1H-benzoimidazol-5-yl ester 4-(2-Methoxy-benzylamino)benzenesulfonic acid 2-(cyclopropanecarbonyl-amino)-1H-benzoimidazol-5-yl ester 4-(4-Hydroxy-cyclohexylamino)-benzenesulfonic acid 2-(cyclopropanecarbonyl-amino)-1H-benzoimidazol-5-yl ester 4-(2-Diethylamino-ethylamino)-benzenesulfonic acid 2-(cyclopropanecarbonyl-amino)-1H-benzoimidazol-5-yl ester 4-(1S-Hydroxymethyl-propylamino)-benzenesulfonic acid 2-(cyclopropanecarbonyl-amino)-1H-benzoimidazol-5-yl ester 4-(2-Ethylamino-ethylamino)-benzenesulfonic acid 2-(cyclopropanecarbonyl-amino)-1H-benzoimidazol-5-yl ester 4-(2-Diisopropylamino-ethylamino)-benzenesulfonic acid 2-(cyclopropanecarbonyl-amino)-1H-benzoimidazol-5-yl ester 4-(2-Morpholin-4-yl-ethylamino)-benzenesulfonic acid 2-(cyclopropanecarbonyl-amino)-1H-benzoimidazol-5-yl ester 4-(1-Aza-bicyclo[2.2.2]oct-3-ylamino)-benzenesulfonic acid 2-(cyclopropane-carbonyl-amino)-1H-benzoimidazol-5-yl ester 4-(2-Phenylamino-ethylamino)-benzenesulfonic acid 2-(cyclopropanecarbonyl-amino)-1H-benzoimidazol-5-yl ester 4-(1-Benzyl-pyrrolidin-3-ylamino)-benzenesulfonic acid 2-(cyclopropanecarbonyl-amino)-1H-benzoimidazol-5-yl ester 4-(2R-Carbamoyl-pyrrolidin-1-yl)-benzenesulfonic acid 2-(cyclopropanecarbonyl-amino)-1H-benzoimidazol-5-yl ester 4-(3-Dimethylamino-propylamino)-benzenesulfonic acid 2-(cyclopropanecarbonyl-amino)-1H-benzoimidazol-5-yl ester 4-(2-piperazin-1-yl-ethylamino)-benzenesulfonic acid 2-(cyclopropanecarbonyl-amino)-1H-benzoimidazol-5-yl ester 4-(2-Carbamoyl-cyclohexylamino)-benzenesulfonic acid 2-(cyclopropanecarbonyl-amino)-1H-benzoimidazol-5-yl ester 4-(2-Acetylamino-ethylamino)-benzenesulfonic acid 2-(cyclopropanecarbonyl-amino)-1H-benzoimidazol-5-yl ester 4-[2-(2-Amino-ethylamino)-ethylamino]-benzenesulfonic acid 2-(cyclopropane-carbonyl-amino)-1H-benzoimidazol-5-yl ester 4-[3-(2-Oxo-pyrrolidin-1-yl)-propylamino]-benzenesulfonic acid 2-(cyclopropane-carbonyl-amino)-1H-benzoimidazol-5-yl ester 4-[2-(1H-Imidazol-4-yl)-ethylamino]-benzenesulfonic acid 2-(cyclopropanecarbonyl-amino)-1H-benzoimidazol-5-yl ester 4-[(Pyridin-2-ylmethyl)-amino]-benzenesulfonic acid 2-(cyclopropanecarbonyl-amino)-1H-benzoimidazol-5-yl ester 4-Cyclobutylamino-benzenesulfonic acid 2-(cyclopropanecarbonyl-amino)-1H-benzoimidazol-5-yl ester 4-[2-(2-Hydroxy-ethoxy)-ethylamino]-benzenesulfonic acid 2-(cyclopropane-carbonyl-amino)-1H-benzoimidazol-5-yl ester 4-(2,3-Dihydroxy-propylamino)-benzenesulfonic acid 2-(cyclopropanecarbonyl-amino)-1H-benzoimidazol-5-yl ester 4-(2-Imidazol-1-yl-ethylamino)-benzenesulfonic acid 2-(cyclopropanecarbonyl-amino)-1H-benzoimidazol-5-yl ester 4-[2-(2-Hydroxy-ethylamino)-ethylamino]-benzenesulfonic acid 2-(cyclopropane-carbonyl-amino)-1H-benzoimidazol-5-yl ester 4-(2-Methoxy-ethylamino)-benzenesulfonic acid 2-(cyclopropanecarbonyl-amino)-1H-benzoimidazol-5-yl ester 4-(2-Dimethylamino-1-methyl-ethylamino)-benzenesulfonic acid 2-(cyclopropane-carbonyl-amino)-1H-benzoimidazol-5-yl ester 4-(Pyrrolidin-3-ylamino)-benzenesulfonic acid 2-(cyclopropanecarbonyl-amino)-1H-benzoimidazol-5-yl ester 4-[2-(1H-Indol-3-yl)-ethylamino]-benzenesulfonic acid 2-(cyclopropanecarbonyl-amino)-1H-benzoimidazol-5-yl ester 4-(2-Dimethylamino-ethylamino)-benzenesulfonic acid 2-(cyclopropanecarbonyl-amino)-1H-benzoimidazol-5-yl ester 4-(2-Phenoxy-ethylamino)-benzenesulfonic acid 2-(cyclopropanecarbonyl-amino)-1H-benzoimidazol-5-yl ester 4-(Bicyclo[2.2.1]hept-2-ylamino)-benzenesulfonic acid 2-(cyclopropanecarbonyl-amino)-1H-benzoimidazol-5-yl ester 4-(2-Methylamino-ethylamino)-benzenesulfonic acid 2-(cyclopropanecarbonyl-amino)-1H-benzoimidazol-5-yl ester 4-(2-Propylamino-ethylamino)-benzenesulfonic acid 2-(cyclopropanecarbonyl-amino)-1H-benzoimidazol-5-yl ester 4-(1-Methyl-2-phenoxy-ethylamino)-benzenesulfonic acid 2-(cyclopropanecarbonyl-amino)-1H-benzoimidazol-5-yl ester 4-[(Piperidin-4-ylmethyl)-amino]-benzenesulfonic acid 2-(cyclopropanecarbonyl-amino)-1H-benzoimidazol-5-yl ester 4-(4-Methoxy-benzylamino)-benzenesulfonic acid 2-(cyclopropanecarbonyl-amino)-1H-benzoimidazol-5-yl ester 4-(1H-Benzoimidazol-5-ylamino)-benzenesulfonic acid 2-(cyclopropanecarbonyl-amino)-1H-benzoimidazol-5-yl ester 4-(3-Methoxy-propylamino)-benzenesulfonic acid 2-(cyclopropanecarbonyl-amino)-1H-benzoimidazol-5-yl ester 4-(2,2-Dimethoxy-ethylamino)-benzenesulfonic acid 2-(cyclopropanecarbonyl-amino)-1H-benzoimidazol-5-yl ester 4-(4-Dimethylamino-phenylamino)-benzenesulfonic acid 2-(cyclopropanecarbonyl-amino)-1H-benzoimidazol-5-yl ester 4-(3-Methoxy-benzylamino)-benzenesulfonic acid 2-(cyclopropanecarbonyl-amino)-1H-benzoimidazol-5-yl ester 4-(4-Pyrrolidin-1-yl-butylamino)-benzenesulfonic acid 2-(cyclopropanecarbonyl-amino)-1H-benzoimidazol-5-yl ester 4-(2,3-Dimethoxy-benzylamino)-benzenesulfonic acid 2-(cyclopropanecarbonyl-amino)-1H-benzoimidazol-5-yl ester 4-Prop-2-ynylamino-benzenesulfonic acid 2-(cyclopropanecarbonyl-amino)-1H-benzoimidazol-5-yl ester 4-[4-(2-Hydroxy-ethyl)-piperazin-1-yl]-benzenesulfonic acid 2-(cyclopropane-carbonyl-amino)-1H-benzoimidazol-5-yl ester 4-[(Pyridin-4-ylmethyl)-amino]-benzenesulfonic acid 2-(cyclopropanecarbonyl-amino)-1H-benzoimidazol-5-yl ester 4-[2-(Ethyl-m-tolyl-amino)-ethylamino]-benzenesulfonic acid 2-(cyclopropane-carbonyl-amino)-1H-benzoimida-zol-5-yl ester 4-(2-Hydroxy-cyclohexylamino)-benzenesulfonic acid 2-(cyclopropanecarbonyl-amino)-1H-benzoimidazol-5-yl ester 4-(3-Dimethylamino-2,2-dimethyl-propylamino)-benzenesulfonic acid 2-(cyclopropanecarbonyl-amino)-1H-benzoimidazol-5-yl ester 4-[3-(2-Hydroxy-ethylamino)-propylamino]-benzenesulfonic acid 2-(cyclopropane-carbonyl-amino)-1H-benzoimidazol-5-yl ester 4-[(Tetrahydro-furan-2-ylmethyl)-amino]-benzenesulfonic acid 2-(cyclopropane-carbonyl-amino)-1H-benzoimidazol-5-yl ester 4-[(Tetrahydro-furan-2R-ylmethyl)-amino]-benzenesulfonic acid 2-(cyclopropane-carbonyl-amino)-1H-benzoimidazol-5-yl ester 4-[(Tetrahydro-furan-2S-ylmethyl)-amino]-benzenesulfonic acid 2-(cyclopropane-carbonyl-amino)-1H-benzoimidazol-5-yl ester 4-(2-Butylamino-ethylamino)-benzenesulfonic acid 2-(cyclopropanecarbonyl-amino)-1H-benzoimidazol-5-yl ester
4-(3-Methylamino-propylamino)-benzenesulfonic acid 2-(cyclopropanecarbonyl-amino)-1H-benzoimidazol-5-yl ester
4-(1S,2-Dicarbamoyl-ethylamino)-benzenesulfonic acid 2-(cyclopropanecarbonyl-amino)-1H-benzoimidazol-5-yl ester
2-{4-[2-(Cyclopropanecarbonyl-amino)-1H-benzoimidazol-5-yloxysulfonyl]-phenylamino}-3R-hydroxy-propionic acid methyl ester
4-(2-Carbamoyl-ethylamino)-benzenesulfonic acid 2-(cyclopropanecarbonyl-amino)-1H-benzoimidazol-5-yl ester
4-(3-Methoxy-propylamino)-benzenesulfonic acid 2-(cyclopropanecarbonyl-amino)-1H-benzoimidazol-5-yl ester
4-(3,4,5-Trimethoxy-benzylamino)-benzenesulfonic acid 2-(cyclopropanecarbonyl-amino)-1H-benzoimidazol-5-yl ester
4-(Carbamoylmethyl-amino)-benzenesulfonic acid 2-(cyclopropanecarbonyl-amino)-1H-benzoimidazol-5-yl ester
1-{4-[2-(Cyclopropanecarbonyl-amino)-1H-benzoimidazol-5-yloxysulfonyl]-phenyl}-piperidine-4-carboxylic acid ethyl ester
4-(2-Amino-2-methyl-propylamino)-benzenesulfonic acid 2-(cyclopropanecarbonyl-amino)-1H-benzoimidazol-5-yl ester
3-{4-[2-(Cyclopropanecarbonyl-amino)-1H-benzoimidazol-5-yloxysulfonyl]-phenylamino}-propionic acid methyl ester
4-(3-Morpholin-4-yl-propylamino)-benzenesulfonic acid 2-(cyclopropanecarbonyl-amino)-1H-benzoimidazol-5-yl ester
4-(5-Hydroxy-pentylamino)-benzenesulfonic acid 2-(cyclopropanecarbonyl-amino)-1H-benzoimidazol-5-yl ester
4-[(5S-Amino-2,2,4S-trimethyl-cyclopentylmethyl)-amino]-benzenesulfonic acid 2-(cyclopropanecarbonyl-amino)-1H-benzoimidazol-5-yl ester
4-(2-Hydroxymethyl-phenylamino)-benzenesulfonic acid 2-(cyclopropanecarbonyl-amino)-1H-benzoimidazol-5-yl ester
4-(4-Ethoxy-phenylamino)-benzenesulfonic acid 2-(cyclopropanecarbonyl-amino)-1H-benzoimidazol-5-yl ester
4-Ethylamino-benzenesulfonic acid 2-(cyclopropanecarbonyl-amino)-1H-benzoimidazol-5-yl ester
4-(2-Sulfo-ethylamino)-benzenesulfonic acid 2-(cyclopropanecarbonyl-amino)-1H-benzoimidazol-5-yl ester
4-{4-[2-(Cyclopropanecarbonyl-amino)-1H-benzoimidazol-5-yloxysulfonyl]-phenylamino}-piperidine-1-carboxylic acid ethyl ester
4-({4-[2-(Cyclopropanecarbonyl-amino)-1H-benzoimidazol-5-yloxysulfonyl]-phenylamino}-methyl)-benzoic acid
4-[(1-Carbamimidoyl-piperidin-4-ylmethyl)-amino]-benzenesulfonic acid 2-(cyclopropanecarbonyl-amino)-1H-benzoimidazol-5-yl ester
4-{4-[2-(Cyclopropanecarbonyl-amino)-1H-benzoimidazol-5-yloxysulfonyl]-phenyl}-piperazine-1-carboxylic acid tert-butyl ester
3-{4-[2-(Cyclopropanecarbonyl-amino)-1H-benzoimidazol-5-yloxysulfonyl]-phenylamino}-3-phenyl-propionic acid
4-Piperidin-1-yl-benzenesulfonic acid 2-(cyclopropanecarbonyl-amino)-1H-benzoimidazol-5-yl ester
4-(1-Methyl-4-oxo-imidazolidin-2-ylideneamino)-benzenesulfonic acid 2-(cyclopropanecarbonyl-amino)-1H-benzoimidazol-5-yl ester
4-(4-Methyl-piperazin-1-yl)-benzenesulfonic acid 2-(cyclopropanecarbonyl-amino)-1H-benzoimidazol-5-yl ester
4-(3-Hydroxy-pyrrolidin-1-yl)-benzenesulfonic acid 2-(cyclopropanecarbonyl-amino)-1H-benzoimidazol-5-yl ester
4-(Cyclopropylmethyl-amino)-benzenesulfonic acid 2-(cyclopropanecarbonyl-amino)-1H-benzoimidazol-5-yl ester
4-[(2-Dimethylamino-ethyl)-methyl-amino]-benzenesulfonic acid 2-(cyclopropane-carbonyl-amino)-1H-benzoimidazol-5-yl ester
4-Isobutylamino-benzenesulfonic acid 2-(cyclopropanecarbonyl-amino)-1H-benzoimidazol-5-yl ester
4-[Ethyl-(2-hydroxy-ethyl)-amino]-benzenesulfonic acid 2-(cyclopropanecarbonyl-amino)-1H-benzoimidazol-5-yl ester
4-(2-Hydroxy-1-hydroxymethyl-ethylamino)-benzenesulfonic acid 2-(cyclopropane-carbonyl-amino)-1H-benzoimidazol-5-yl ester
4-Propylamino-benzenesulfonic acid 2-(cyclopropanecarbonyl-amino)-1H-benzoimidazol-5-yl ester
4-Cyclopropylamino-benzenesulfonic acid 2-(cyclopropanecarbonyl-amino)-1H-benzoimidazol-5-yl ester
4-Morpholin-4-yl-benzenesulfonic acid 2-(cyclopropanecarbonyl-amino)-1H-benzoimidazol-5-yl ester
4-[2-(1-Methyl-pyrrolidin-2-yl)-ethylamino]-benzenesulfonic acid 2-(cyclopropane-carbonyl-amino)-1H-benzoimidazol-5-yl ester
4-[(1,3-Dimethyl-1H-pyrazol-4-ylmethyl)-amino]-benzenesulfonic acid 2-(cyclopropanecarbonyl-amino)-1H-benzoimidazol-5-yl ester
4-(4-Acetylamino-benzylamino)-benzenesulfonic acid 2-(cyclopropanecarbonyl-amino)-1H-benzoimidazol-5-yl ester
4-(3-Cyclohexylamino-propylamino)-benzenesulfonic acid 2-(cyclopropanecarbonyl-amino)-1H-benzoimidazol-5-yl ester
4-(3-Ethoxy-propylamino)-benzenesulfonic acid 2-(cyclopropanecarbonyl-amino)-1H-benzoimidazol-5-yl ester
4-Pyrrolidin-1-yl-benzenesulfonic acid 2-(cyclopropanecarbonyl-amino)-1H-benzoimidazol-5-yl ester
4-(4-Methyl-benzylamino)-benzenesulfonic acid 2-(cyclopropanecarbonyl-amino)-1H-benzoimidazol-5-yl ester
4-[1,4']Bipiperidinyl-1'-yl-benzenesulfonic acid 2-(cyclopropanecarbonyl-amino)-1H-benzoimidazol-5-yl ester
4-(2-Pyridin-3-yl-pyrrolidin-1-yl)-benzenesulfonic acid 2-(cyclopropanecarbonyl-amino)-1H-benzoimidazol-5-yl ester
4-(4-Hydroxy-piperidin-1-yl)-benzenesulfonic acid 2-(cyclopropanecarbonyl-amino)-1H-benzoimidazol-5-yl ester
4-[(2-Hydroxy-ethyl)-methyl-amino]-benzenesulfonic acid 2-(cyclopropanecarbonyl-amino)-1H-benzoimidazol-5-yl ester
4-[(1-Ethyl-pyrrolidin-2-ylmethyl)-amino]-benzenesulfonic acid 2-(cyclopropane-carbonyl-amino)-1H-benzoimidazol-5-yl ester
4-(3-Hydroxy-pyridin-2-ylamino)-benzenesulfonic acid 2-(cyclopropanecarbonyl-amino)-1H-benzoimidazol-5-yl ester
4-[(1-Carbamoyl-piperidin-4-ylmethyl)-amino]-benzenesulfonic acid 2-(cyclopropanecarbonyl-amino)-1H-benzoimidazol-5-yl ester
4-(2-Pyrrol-1-yl-ethylamino)-benzenesulfonic acid 2-(cyclopropanecarbonyl-amino)-1H-benzoimidazol-5-yl ester
4-(4-Cyclopentyl-piperazin-1-yl)-benzenesulfonic acid 2-(cyclopropanecarbonyl-amino)-1H-benzoimidazol-5-yl ester
4-(2-Propoxy-ethylamino)-benzenesulfonic acid 2-(cyclopropanecarbonyl-amino)-1H-benzoimidazol-5-yl ester 4-(3-Cyclohexylamino-propylamino)-benzenesulfonic acid 2-(cyclopropanecarbonyl-amino)-1H-benzoimidazol-5-yl ester 4-(1H-Indol-5-ylamino)-benzenesulfonic acid 2-(cyclopropanecarbonyl-amino)-1H-benzoimidazol-5-yl ester 4-(4-Amino-benzylamino)-benzenesulfonic acid 2-(cyclopropanecarbonyl-amino)-1H-benzoimidazol-5-yl ester 4-(2S-Methoxymethyl-pyrrolidin-1-yl)-benzenesulfonic acid 2-(cyclopropane-carbonyl-amino)-1H-benzoimidazol-5-yl ester 4-[4-(2-Hydroxy-ethyl)-piperidin-1-yl]-benzenesulfonic acid 2-(cyclopropane-carbonyl-amino)-1H-benzoimidazol-5-yl ester 4-[2-(2-Hydroxy-ethyl)-piperidin-1-yl]-benzenesulfonic acid 2-(cyclopropane-carbonyl-amino)-1H-benzoimidazol-5-yl ester 4-(2-Isopropylamino-ethylamino)-benzenesulfonic acid 2-(cyclopropanecarbonyl-amino)-1H-benzoimidazol-5-yl ester 3-{4-[2-(Cyclopropanecarbonyl-amino)-1H-benzoimidazol-5-yloxysulfonyl]-phenylamino}-propionic acid 4-[Methyl-(2-methylamino-ethyl)-amino]-benzenesulfonic acid 2-(cyclopropane-carbonyl-amino)-1H-benzoimidazol-5-yl ester 4-(3-Acetylamino-pyrrolidin-1-yl)-benzenesulfonic acid 2-(cyclopropanecarbonyl-amino)-1H-benzoimidazol-5-yl ester 4-(Carbamoylmethyl-amino)-benzenesulfonic acid 2-(cyclopropanecarbonyl-amino)-1H-benzoimidazol-5-yl ester 4-(4-Hydroxy-piperidin-1-yl)-benzenesulfonic acid 2-(cyclopropanecarbonyl-amino)-1H-benzoimidazol-5-yl ester 4-(4-Dimethylamino-benzylamino)-benzenesulfonic acid 2-(cyclopropanecarbonyl-amino)-1H-benzoimidazol-5-yl ester 4-(3-Imidazol-1-yl-propylamino)-benzenesulfonic acid 2-(cyclopropanecarbonyl-amino)-1H-benzoimidazol-5-yl ester 4-(Quinoxalin-5-ylamino)-benzenesulfonic acid 2-(cyclopropanecarbonyl-amino)-1H-benzoimidazol-5-yl ester 4-[4-(2-Hydroxy-ethyl)-piperazin-1-yl]-benzenesulfonic acid 2-(cyclopropane-carbonyl-amino)-1H-benzoimidazol-5-yl ester 4-(2-Hydroxy-1,1-dimethyl-ethylamino)-benzenesulfonic acid 2-(cyclopropanecarbonyl-amino)-1H-benzoimidazol-5-yl ester 1-{4-[2-(Cyclopropanecarbonyl-amino)-1H-benzoimidazol-5-yloxysulfonyl]-phenyl}-piperidine-4-carboxylic acid 6-{4-[2-(Cyclopropanecarbonyl-amino)-1H-benzoimidazol-5-yloxysulfonyl]-phenylamino}-hexanoic acid methyl ester 4-[4-(4-Methoxy-phenyl)-piperazin-1-yl]-benzenesulfonic acid 2-(cyclopropane-carbonyl-amino)-1H-benzoimidazol-5-yl ester 4-[4-(2-Methoxy-ethyl)-piperazin-1-yl]-benzenesulfonic acid 2-(cyclopropane-carbonyl-amino)-1H-benzoimidazol-5-yl ester 4-[(2-Hydroxy-ethyl)-phenyl-amino]-benzenesulfonic acid 2-(cyclopropanecarbonyl-amino)-1H-benzoimidazol-5-yl ester 4-[(Furan-2-ylmethyl)-amino]-benzenesulfonic acid 2-(cyclopropanecarbonyl-amino)-1H-benzoimidazol-5-yl ester 1-{4-[2-(Cyclopropanecarbonyl-amino)-1H-benzoimidazol-5-yloxysulfonyl]-phenyl}-aziridine-2-carboxylic acid methyl ester 4-(4-Carbamoyl-piperidin-1-yl)-benzenesulfonic acid 2-(cyclopropanecarbonyl-amino)-1H-benzoimidazol-5-yl ester 4-(3-Methyl-piperazin-1-yl)-benzenesulfonic acid 2-(cyclopropanecarbonyl-amino)-1H-benzoimidazol-5-yl ester 4-(2,6-Dimethyl-morpholin-4-yl)-benzenesulfonic acid 2-(cyclopropanecarbonyl-amino)-1H-benzoimidazol-5-yl ester 4-(4-Phenyl-piperazin-1-yl)-benzenesulfonic acid 2-(cyclopropanecarbonyl-amino)-1H-benzoimidazol-5-yl ester 4-(4-Pyridin-2-yl-piperazin-1-yl)-benzenesulfonic acid 2-(cyclopropanecarbonyl-amino)-1H-benzoimidazol-5-yl ester 4-(4-Diethylamino-1-methyl-butylamino)-benzenesulfonic acid 2-(cyclopropane-carbonyl-amino)-1H-benzoimidazol-5-yl ester 4-{4-[2-(Cyclopropanecarbonyl-amino)-1H-benzoimidazol-5-yloxysulfonyl]-phenyl}-piperazine-1-carboxylic acid ethyl ester 4-(5-Hydroxy-naphthalen-1-ylamino)-benzenesulfonic acid 2-(cyclopropanecarbonyl-amino)-1H-benzoimidazol-5-yl ester 4-[2-(4-Hydroxy-3-methoxy-phenyl)-ethylamino]-benzenesulfonic acid 2-(cyclopropanecarbonyl-amino)-1H-benzoimidazol-5-yl ester 4-(9H-Purin-6-ylamino)-benzenesulfonic acid 2-(cyclopropanecarbonyl-amino)-1H-benzoimidazol-5-yl ester 1-{4-[2-(Cyclopropanecarbonyl-amino)-1H-benzoimidazol-5-yloxysulfonyl]-phenyl}-piperidine-3-carboxylic acid 4-(3,3-Dimethyl-piperidin-1-yl)-benzenesulfonic acid 2-(cyclopropanecarbonyl-amino)-1H-benzoimidazol-5-yl ester 4-(4-Methyl-piperidin-1-yl)-benzenesulfonic acid 2-(cyclopropanecarbonyl-amino)-1H-benzoimidazol-5-yl ester 4-(2-Pyridin-2-yl-ethylamino)-benzenesulfonic acid 2-(cyclopropanecarbonyl-amino)-1H-benzoimidazol-5-yl ester 4-(3-Hydroxymethyl-phenylamino)-benzenesulfonic acid 2-(cyclopropanecarbonyl-amino)-1H-benzoimidazol-5-yl ester 4-(2-Oxo-2,3-dihydro-1H-pyrimidin-4-ylideneamino)-benzenesulfonic acid 2-(cyclopropanecarbonyl-amino)-1H-benzoimidazol-5-yl ester 4-(3-Piperidin-1-yl-propylamino)-benzenesulfonic acid 2-(cyclopropanecarbonyl-amino)-1H-benzoimidazol-5-yl ester 4-[2-(1H-Indol-3-yl)-ethylamino]-benzenesulfonic acid 2-(cyclopropanecarbonyl-amino)-1H-benzoimidazol-5-yl ester 4-(5-Carbamoyl-1H-imidazol-4-ylamino)-benzenesulfonic acid 2-(cyclopropane-carbonyl-amino)-1H-benzoimidazol-5-yl ester 4-(1-Hydroxymethyl-butylamino)-benzenesulfonic acid 2-(cyclopropanecarbonyl-amino)-1H-benzoimidazol-5-yl ester 4-(1-Benzyl-piperidin-4-ylamino)-benzenesulfonic acid 2-(cyclopropanecarbonyl-amino)-1H-benzoimidazol-5-yl ester 4-{4-[2-(2-Hydroxy-ethoxy)-ethyl]-piperazin-1-yl}-benzenesulfonic acid 2-(cyclopropanecarbonyl-amino)-1H-benzoimidazol-5-yl ester 4-(4-Methyl-[1,4]diazepan-1-yl)-benzenesulfonic acid 2-(cyclopropanecarbonyl-amino)-1H-benzoimidazol-5-yl ester 4-(3-Azepan-1-yl-propylamino)-benzenesulfonic acid 2-(cyclopropanecarbonyl-amino)-1H-benzoimidazol-5-yl ester 4-(2,6-cis-Dimethyl-morpholin-4-yl)-benzenesulfonic acid 2-(cyclopropanecarbonyl-amino)-1H-benzoimidazol-5-yl ester 4-(2S-Hydroxymethyl-pyrrolidin-1-yl)-benzenesulfonic acid 2-(cyclopropane-carbonyl-amino)-1H-benzoimidazol-5-yl ester
4-[4-(3-Pyrrolidin-1-yl-propyl)-[1,4]diazepan-1-yl]-benzenesulfonic acid 2-(cyclopropanecarbonyl-amino)-1H-benzoimidazol-5-yl ester
4-trifluoromethoxy-benzenesulfonic acid 2-methoxycarbonylamino-1H-benzoimidazol-5-yl ester
3,5-Dimethyl-isoxazole-4-sulfonic acid 2-methoxycarbonylamino-1H-benzoimidazol-5-yl ester
Thiophene-2-sulfonic acid 2-methoxycarbonylamino-1H-benzoimidazol-5-yl ester
5-Isoxazol-3-yl-thiophene-2-sulfonic acid 2-methoxycarbonylamino-1H-benzoimidazol-5-yl ester
2-Fluoro-benzenesulfonic acid 2-methoxycarbonylamino-1H-benzoimidazol-5-yl ester
5-(1-Methyl-5-trifluoromethyl-1H-pyrazol-3-yl)-thiophene-2-sulfonic acid 2-methoxycarbonylamino-1H-benzoimidazol-5-yl ester
3-Trifluoromethoxy-benzenesulfonic acid 2-methoxycarbonylamino-1H-benzoimidazol-5-yl ester
2-Trifluoromethoxy-benzenesulfonic acid 2-methoxycarbonylamino-1H-benzo-imidazol-5-yl ester
2,6-Difluoro-benzenesulfonic acid 2-methoxycarbonylamino-1H-benzoimidazol-5-yl ester
3-Methoxy-benzenesulfonic acid 2-methoxycarbonylamino-1H-benzoimidazol-5-yl ester
3-(2-Methoxycarbonylamino-1H-benzoimidazol-5-yloxysulfonyl)-thiophene-2-carboxylic acid methyl ester
3,4-Dimethoxy-benzenesulfonic acid 2-methoxycarbonylamino-1H-benzoimidazol-5-yl ester
3-Nitro-benzenesulfonic acid 2-methoxycarbonylamino-1H-benzoimidazol-5-yl ester
3-Trifluoromethyl-benzenesulfonic acid 2-methoxycarbonylamino-1H-benzo-imidazol-5-yl ester
2-Cyano-benzenesulfonic acid 2-methoxycarbonylamino-1H-benzoimidazol-5-yl ester
2-Trifluoromethyl-benzenesulfonic acid 2-methoxycarbonylamino-1H-benzo-imidazol-5-yl ester
2,4-Difluoro-benzenesulfonic acid 2-methoxycarbonylamino-1H-benzoimidazol-5-yl ester
5-Fluoro-2-methyl-benzenesulfonic acid 2-methoxycarbonylamino-1H-benzo-imidazol-5-yl ester
3-Fluoro-benzenesulfonic acid 2-methoxycarbonylamino-1H-benzoimidazol-5-yl ester
4-Cyano-benzenesulfonic acid 2-methoxycarbonylamino-1H-benzoimidazol-5-yl ester
2-Methoxy-5-(2-methoxycarbonylamino-3H-benzoimidazol-5-yloxysulfonyl)-thiophene-3-carboxylic acid methyl ester
1,3,5-Trimethyl-1H-pyrazole-4-sulfonic acid 2-methoxycarbonylamino-3H-benzoimidazol-5-yl ester
6-Morpholin-4-yl-pyridine-3-sulfonic acid 2-methoxycarbonylamino-3H-benzoimidazol-5-yl ester
2,4,6-Trifluoro-benzenesulfonic acid 2-methoxycarbonylamino-1H-benzoimidazol-5-yl ester
4-benzyloxy-benzenesulfonic acid 2-methoxycarbonylamino-1H-benzoimidazol-5-yl ester
4-Ethoxy-benzenesulfonic acid 2-methoxycarbonylamino-3H-benzoimidazol-5-yl ester
4-(2-Morpholin-4-yl-ethoxy)-benzenesulfonic acid 2-methoxycarbonylamino-3H-benzoimidazol-5-yl ester
4-(2-Methoxy-ethoxy)-benzenesulfonic acid 2-methoxycarbonylamino-3H-benzoimidazol-5-yl ester
4-(2-piperidin-1-yl-ethoxy)-benzenesulfonic acid 2-methoxycarbonylamino-3H-benzoimidazol-5-yl ester
[4-(2-Methoxycarbonylamino-3H-benzoimidazol-5-yloxysulfonyl)-phenoxy]-acetic acid
4-(2-oxo-2-pyrrolidin-1-yl-ethoxy)-benzenesulfonic acid 2-methoxycarbonylamino-1H-benzoimidazol-5-yl-ester
4-[2-(4-Methyl-piperazin-1-yl)-2-oxo-ethoxy]-benzenesulfonic acid 2-methoxycarbonylamino-1H-benzoimidazol-5-yl ester
4-[(3-diethylamino-propylcarbamoyl)-methoxy]-benzenesulfonic acid 2-methoxycarbonylamino-1H-benzoimidazol-5-yl ester
4-{[(furan-2-ylmethyl)-carbamoyl]-methoxy}-benzenesulfonic acid 2-methoxycarbonylamino-1H-benzoimidazol-5-yl ester
4-(cyclopropylmethyl-amino)-benzenesulfonic acid 2-methoxycarbonylamino-1H-benzoimidazol-5-yl ester
4-(2-methoxy-ethylamino)-benzenesulfonic acid 2-methoxycarbonylamino-1H-benzoimidazol-5-yl ester
4-(2-hydroxy-1-methyl-ethylamino)-benzenesulfonic acid 2-methoxycarbonylamino-1H-benzoimidazol-5-yl ester
4-(benzylamino)-benzenesulfonic acid 2-methoxycarbonylamino-1H-benzoimidazol-5-yl ester
4-(2-Morpholin-4-yl-ethylamino)-benzenesulfonic acid 2-methoxycarbonylamino-1H-benzoimidazol-5-yl ester
4-(2-Piperidin-4-yl-ethylamino)-benzenesulfonic acid 2-[3-(2-piperidin-1-yl-ethyl)-ureido]-3H-benzoimidazol-5-yl ester
4-[(1-Ethyl-pyrrolidin-2-ylmethyl)-amino]-benzenesulfonic acid 2-[3-(2-piperidin-1-yl-ethyl)-ureido]-3H-benzoimidazol-5-yl ester
4-cyclopentylamino-benzenesulfonic acid 2-(3,4-dimethoxy-phenylamino)-1H-benzoimidazol-5-yl ester
4-Cyclopentylamino-benzenesulfonic acid 2-phenylamino-1H-benzoimidazol-5-yl ester
4-Cyclopentylamino-benzenesulfonic acid 2-(4-morpholin-4-yl-phenylamino)-1H-benzoimidazol-5-yl ester
4-Cyclopentylamino-benzenesulfonic acid 2-(3,5-dimethyl-phenylamino)-1H-benzoimidazol-5-yl ester
4-Cyclopentylamino-benzenesulfonic acid 2-(4-methoxy-phenylamino)-1H-benzoimidazol-5-yl ester
4-Cyclopentylamino-benzenesulfonic acid 2-(4-dimethylamino-phenylamino)-1H-benzoimidazol-5-yl ester
4-Cyclopentylamino-benzenesulfonic acid 2-(3-methoxy-5-trifluoromethyl-phenylamino)-1H-benzoimidazol-5-yl ester
3-[5-(4-Cyclopentylamino-benzenesulfonyloxy)-1H-benzoimidazol-2-ylamino]-benzoic acid ethyl ester
4-Cyclopentylamino-benzenesulfonic acid 2-[(4-(4-methyl-piperazin-1-yl)-phenylamino)-1H-benzoimidazol-5-yl ester
4-cyclopentylamino-benzenesulfonic acid 2-(3-phenyl-propionylamino)-1H-benzoimidazol-5-yl ester
4-cyclopentylamino-benzenesulfonic acid 2-[2-2-methoxy-ethoxy)-acetylamino]-1H-benzoimidazol-5-yl ester
4-fluoro-benzenesulfonic acid 2-(3(chloro-4-methoxy-benzylamino)-3H-benzoimidazol-5-yl ester
4-Fluoro-benzenesulfonic acid 2-[(3-phenyl-[1,2,4]oxadiazol-5-ylmethyl)-amino]-3H-benzoimidazol-5-yl ester
4-Fluoro-benzenesulfonic acid 2-(3-chloro-benzylamino)-3H-benzoimidazol-5-yl ester
4-Fluoro-benzenesulfonic acid 2-(3-methoxy-benzylamino)-3H-benzoimidazol-5-yl ester
4-Fluoro-benzenesulfonic acid 2-benzylamino-3H-benzoimidazol-5-yl ester
4-cyclopentylamino-benzenesulfonic acid 2-benzylamino-3H-benzoimidazol-5-yl ester 4-Cyclopentylamino-benzenesulfonic acid 2-[(3-phenyl-[1,2,4]oxadiazol-5-ylmethyl)-amino]-3H-benzoimidazol-5-yl ester
4-Cyclopentylamino-benzenesulfonic acid 2-(3-methoxy-benzylamino)-3H-benzoimidazol-5-yl ester
4-Cyclopentylamino-benzenesulfonic acid 2-(3-chloro-4-methoxy-benzylamino)-3H-benzoimidazol-5-yl ester
4-(Cyclopropylmethyl-amino)-benzenesulfonic acid 2-[3-(2-morpholin-4-yl-ethyl)-ureido]-1H-benzoimidazol-5-yl ester
4-(Cyclopropylmethyl-amino)-benzenesulfonic acid 2-[3-(2-morpholin-4-yl-ethyl)-ureido]-1H-benzoimidazol-5-yl ester
4-(Cyclopropylmethyl-amino)-benzenesulfonic acid 2-(3-pyridin-2-ylmethyl)-ureido]-1H-benzoimidazol-5-yl ester
4-(Cyclopropylmethyl-amino)-benzenesulfonic acid 2-[3-(2-methoxy-ethyl)-ureido]-1H-benzoimidazol-5-yl ester
4-(Cyclopropylmethyl-amino)-benzenesulfonic acid 2-[3-(2-ethyl)-ureido]-1H-benzoimidazol-5-yl ester
4-(2-Methoxy-ethylamino)-benzenesulfonic acid 2-[3-(2-morpholin-4-yl-ethyl)-ureido]-1H-benzoimidazol-5-yl ester
4-(2-Methoxy-ethylamino)-benzenesulfonic acid 2-(3-pyridin-2-ylmethyl)-ureido]-1H-benzoimidazol-5-yl ester
4-(2-Methoxy-ethylamino)-benzenesulfonic acid 2-[3-(2-methoxy-ethyl)-ureido]-1H-benzoimidazol-5-yl ester
4-(2-Methoxy-ethylamino)-benzenesulfonic acid 2-[3-(2-ethyl)-ureido]-1H-benzoimidazol-5-yl ester
4-(2-Hydroxy-1-methyl-ethylamino)-benzenesulfonic acid 2-[3-(2-morpholin-4-yl-ethyl)-ureido]-1H-benzoimidazol-5-yl ester
4-(2-Hydroxy-1-methyl-ethylamino)-benzenesulfonic acid 2-(3-pyridin-2-ylmethyl)-ureido]-1H-benzoimidazol-5-yl ester
4-(2-Hydroxy-1-methyl-ethylamino)-benzenesulfonic acid 2-[3-(2-methoxy-ethyl)-ureido]-1H-benzoimidazol-5-yl ester
4-(2-Hydroxy-1-methyl-ethylamino)-benzenesulfonic acid 2-[3-(2-ethyl)-ureido]-1H-benzoimidazol-5-yl ester
4-Benzyloxy-benzenesulfonic acid 2-[3-(2-morpholin-4-yl-ethyl)-ureido]-1H-benzoimidazol-5-yl ester
4-Benzyloxy-benzenesulfonic acid 2-(3-pyridin-2-ylmethyl)-ureido]-1H-benzoimidazol-5-yl ester
4-Benzyloxy-benzenesulfonic acid 2-[3-(2-methoxy-ethyl)-ureido]-1H-benzoimidazol-5-yl ester
4-benzyloxy-benzenesulfonic acid 2-[3-(2-ethyl)-ureido]-1H-benzoimidazol-5-yl ester
4-(2-Morpholin-4-yl-ethylamino)-benzenesulfonic acid 2-(3-pyridin-2-ylmethyl)-ureido]-1H-benzoimidazol-5-yl ester
4-(2-Morpholin-4-yl-ethylamino)-benzenesulfonic acid 2-[3-(2-methoxy-ethyl)-ureido]-1H-benzoimidazol-5-yl ester
4-[(Piperidin-4-ylmethyl)-amino]-benzenesulfonic acid 2-[3-(2-morpholin-4-yl-ethyl)-ureido]-1H-benzoimidazol-5-yl ester
4-[(Piperidin-4-ylmethyl)-amino]-benzenesulfonic acid 2-(3-pyridin-2-ylmethyl)-ureido]-1H-benzoimidazol-5-yl ester
4-[(Piperidin-4-ylmethyl)-amino]-benzenesulfonic acid 2-[3-(2-methoxy-ethyl)-ureido]-1H-benzoimidazol-5-yl ester
4-Benzylamino-benzenesulfonic acid 2-[3-(2-morpholin-4-yl-ethyl)-ureido]-1H-benzoimidazol-5-yl ester
4-Benzylamino-benzenesulfonic acid 2-(3-pyridin-2-ylmethyl)-ureido]-1H-benzoimidazol-5-yl ester
4-Benzylamino-benzenesulfonic acid 2-[3-(2-methoxy-ethyl)-ureido]-1H-benzoimidazol-5-yl ester
4-Benzylamino-benzenesulfonic acid 2-[3-(2-ethyl)-ureido]-1H-benzoimidazol-5-yl ester
4-[(1-ethyl-pyrrolidin-2ylmethyl)-amino]-benzenesulfonic acid 2-(3-pyridin-2-ylmethyl)-ureido]-1H-benzoimidazol-5-yl ester
4-(4-hydroxy-piperidin-1-yl)-benzenesulfonic acid 2-[(4-hydroxy-piperidine-1-carbonyl)-amino]-1H-benzoimidazol-5-yl ester
4-(4-Methyl-piperazin-1-yl)-benzenesulfonic acid 2-[(4-methyl-piperazin-1-carbonyl)-amino]-3H-benzoimidazol-5-yl ester
4-[(tetrahydro-pyran-4-ylmethyl)-amino]-benzenesulfonic acid 2-[3-(tetrahydro-pyran-4-ylmethyl)-ureido]-3H-benzoimidazol-5-yl ester
4-(2-Fluoro-ethylamino)-benzenesulfonic acid 2-[3-(2-fluoro-ethyl)-ureido]-3H-benzoimidazol-5-yl ester
4-(2-piperidin-1-yl-ethylamino)-benzenesulfonic acid 2-[3-(2-piperidin-1-yl-ethyl)-ureido]-3H-benzoimidazol-5-yl ester
4-phenethylamino-benzenesulfonic acid 2-(3-phenethyl-ureido)-3H-benzoimidazol-5-yl ester
4-[3-(2-oxo-pyrrolidin-1-yl)-propylamino]-benzenesulfonic acid 2-{3-[3-(2-oxo-pyrrolidin-1-yl)-propyl]-ureido}-3H-benzoimidazol-5-yl ester
4-(4-fluoro-benzylamino)-benzenesulfonic acid 2-[3-(4-fluoro-benzyl)-ureido]-3H-benzoimidazol-5-yl ester
4-(2-hydroxy-2-methyl-propylamino)-benzenesulfonic acid 2-[3-(2-hydroxy-3-methyl-propyl)-ureido]-3H-benzoimidazol-5-yl ester
4-(3-hydroxy-propylamino)-benzenesulfonic acid 2-[3-(3-hydroxy-propyl)-ureido]-3H-benzoimidazol-5-yl ester
4-(2,2,6,6-tetramethyl-piperidin-4-ylamino)-benzenesulfonic acid 2-[3-(2,2,6,6-tetramethyl-piperidin-4-yl)-ureido]-3H-benzoimidazol-5-yl ester
4-(2-dimethylamino-ethylamino)-benzenesulfonic acid 2-[3-(2-dimethylamino-ethyl)-ureido]-3H-benzoimidazol-5-yl ester
4-morpholin-4-yl-benzenesulfonic acid 2-[(morpholine-4-carbonyl)-amino]-3H-benzoimidazol-5-yl ester
4-(2-Hydroxy-3-methoxy-propylamino)-benzenesulfonic acid 2-[3-(2-hydroxy-3-methoxy-propyl)-ureido]-3H-benzoimidazol-5-yl ester
4-[(Pyridin-2-ylmethyl)-amino]-benzenesulfonic acid 2-(3-pyridin-2-yl-ethyl-ureido)-3H-benzoimidazol-5-yl ester
4-(2-hydroxy-propylamino)-benzenesulfonic acid 2-[3-(2-hydroxy-propyl)-ureido]-3H-benzoimidazol-5-yl ester
4-(4-methoxy-benzylamino)-benzenesulfonic acid 2-[3-(4-methoxy-benzyl)-ureido]-3H-benzoimidazol-5-yl ester
4-(2-pyrrolidin-1-yl-ethylamino)-benzenesulfonic acid 2-[3-(2-pyrrolidin-1-yl-ethyl)-ureido]-3H-benzoimidazol-5-yl ester
4-(1-phenyl-ethylamino)-benzenesulfonic acid 2-[3-(1-phenyl-ethyl)-ureido]-3H-benzoimidazol-5-yl ester
4-(2-diethylamino-ethylamino)-benzenesulfonic acid 2-[3-(2-diethylamino-ethyl)-ureido]-3H-benzoimidazol-5-yl ester
4-(1-hydroxymethyl-cyclopentylamino)-benzenesulfonic acid 2-[3-(1-hydroxy-methyl-cyclopentyl)-ureido]-3H-benzoimidazol-5-yl ester
3-(4-{2-[3-(3-Methoxycarbonyl-ethyl)-ureido]-1H-benzoimidazol-5-yloxysulfonyl}-phenylamino)-propionic acid methyl ester
4-(4-Hydroxy-piperidin-1-yl)-benzenesulfonic acid 2-[3-(2-morpholin-4-yl-ethyl)-ureido]-1H-benzoimidazol-5-yl ester 4-(4-methyl-piperazin-1-yl)-benzenesulfonic acid 2-[3-(2-morpholin-4-yl-ethyl)-ureido]-3H-benzimidazol-5-yl ester
4-(4-methyl-piperazin-1-yl)-benzenesulfonic acid 2-(3-pyridin-2-ylmethyl-ureido)-3H-benzimidazol-5-yl ester
4-(4-methyl-piperazin-1-yl)-benzenesulfonic acid 2-[3-(2-methoxy-ethyl)-ureido]-3H-benzimidazol-5-yl ester
4-(4-hydroxy-piperidin-1-yl)-benzenesulfonic acid 2-[3-(2-morpholin-4-yl-ethyl)-ureido]-3H-benzimidazol-5-yl ester
4-(4-hydroxy-piperidin-1-yl)-benzenesulfonic acid 2-(3-pyridin-2-ylmethyl-ureido)-3H-benzimidazol-5-yl ester
4-(4-hydroxy-piperidin-1-yl)-benzenesulfonic acid 2-[3-(2-methoxy-ethyl)-ureido]-3H-benzimidazol-5-yl ester
4-(4-hydroxy-piperidin-1-yl)-benzenesulfonic acid 2-(3-ethyl-ureido)-3H-benzimidazol-5-yl ester
4-[(Pyridin-2-ylmethyl)-amino]-benzenesulfonic acid 2-[3-(2-morpholin-4-yl-ethyl)-ureido]-3H-benzimidazol-5-yl ester
4-[(Pyridin-2-ylmethyl)-amino]-benzenesulfonic acid 2-(3-pyridin-2-ylmethyl-ureido)-3H-benzimidazol-5-yl ester
4-[(Pyridin-2-ylmethyl)-amino]-benzenesulfonic acid 2-[3-(2-methoxy-ethyl)-ureido]-3H-benzimidazol-5-yl ester
4-[(Pyridin-2-ylmethyl)-amino]-benzenesulfonic acid 2-[3-(2-methoxy-ethyl)-ureido]-3H-benzimidazol-5-yl ester
4-(3-Hydroxy-propylamino)-benzenesulfonic acid 2-[3-(2-morpholin-4-yl-ethyl)-ureido]-3H-benzimidazol-5-yl ester
4-(3-Hydroxy-propylamino)-benzenesulfonic acid 2-(3-pyridin-2-ylmethyl-ureido)-3H-benzimidazol-5-yl ester
4-(3-Hydroxy-propylamino)-benzenesulfonic acid 2-[3-(2-methoxy-ethyl)-ureido]-3H-benzimidazol-5-yl ester
4-(3-Hydroxy-propylamino)-benzenesulfonic acid 2-(3-ethyl-ureido)-3H-benzimidazol-5-yl ester
4-(2,2,6,6-tetramethyl-piperidin-4-ylamino)-benzenesulfonic acid 2-[3-(2-morpholin-4-yl-ethyl)-ureido]-3H-benzimidazol-5-yl ester
4-(2,2,6,6-tetramethyl-piperidin-4-ylamino)-benzenesulfonic acid 2-(3-pyridin-2-ylmethyl-ureido)-3H-benzimidazol-5-yl ester
4-(2-dimethylamino-ethylamino)-benzenesulfonic acid 2-[3-(2-morpholin-4-yl-ethyl)-ureido]-3H-benzimidazol-5-yl ester
4-(2-dimethylamino-ethylamino)-benzenesulfonic acid 2-(3-pyridin-2-ylmethyl-ureido)-3H-benzimidazol-5-yl ester
4-morpholin-4-yl-benzenesulfonic acid 2-[3-(2-morpholin-4-yl-ethyl)-ureido]-3H-benzimidazol-5-yl ester
4-morpholin-4-yl-benzenesulfonic acid 2-(3-pyridin-2-ylmethyl-ureido)-3H-benzimidazol-5-yl ester
4-[3-(2-oxo-pyrrolidin-1-yl)-propylamino]-benzenesulfonic acid 2-[3-(2-morpholin-4-yl-ethyl)-ureido]-3H-benzimidazol-5-yl ester
4-[3-(2-oxo-pyrrolidin-1-yl)-propylamino]-benzenesulfonic acid 2-(3-pyridin-2-ylmethyl-ureido)-3H-benzimidazol-5-yl ester
4-(3-Hydroxy-propylamino)-benzenesulfonic acid 2-(3-ethyl-ureido)-3H-benzimidazol-5-yl ester
4-(2-Hydroxy-2-methyl-propylamino)-benzenesulfonic acid 2-[3-(2-morpholin-4-yl-ethyl)-ureido]-3H-benzimidazol-5-yl ester
4-(2-Hydroxy-2-methyl-propylamino)-benzenesulfonic acid 2-(3-pyridin-2-ylmethyl-ureido)-3H-benzimidazol-5-yl ester
4-(2-Hydroxy-2-methyl-propylamino)-benzenesulfonic acid 2-[3-(2-methoxy-ethyl)-ureido]-3H-benzimidazol-5-yl ester
4-(2-Hydroxy-2-methyl-propylamino)-benzenesulfonic acid-2-[3-(3-hydroxy-propyl)-ureido]-3H-benzimidazol-5-yl ester
4-[(Tetrahydro-pyran-4-ylmethyl)-amino]-benzenesulfonic acid 2-[3-(2-morpholin-4-yl-ethyl)-ureido]-3H-benzimidazol-5-yl ester
4-[(Tetrahydro-pyran-4-ylmethyl)-amino]-benzenesulfonic acid 2-(3-pyridin-2-ylmethyl-ureido)-3H-benzimidazol-5-yl ester
4-[(Tetrahydro-pyran-4-ylmethyl)-amino]-benzenesulfonic acid 2-[3-(2-methoxy-ethyl)-ureido]-3H-benzimidazol-5-yl ester
4-[(Tetrahydro-pyran-4-ylmethyl)-amino]-benzenesulfonic acid 2-[3-(3-hydroxy-propyl)-ureido]-3H-benzimidazol-5-yl ester
4-(2-fluoro-ethylamino)-benzenesulfonic acid 2-[3-(2-morpholin-4-yl-ethyl)-ureido]-3H-benzimidazol-5-yl ester
4-(2-fluoro-ethylamino)-benzenesulfonic acid 2-(3-pyridin-2-ylmethyl-ureido)-3H-benzimidazol-5-yl ester
4-(2-Piperidin-1-yl-ethylamino)-benzenesulfonic acid 2-[3-(2-morpholin-4-yl-ethyl)-ureido]-3H-benzimidazol-5-yl ester
4-(2-Piperidin-1-yl-ethylamino)-benzenesulfonic acid 2-(3-pyridin-2-ylmethyl-ureido)-3H-benzimidazol-5-yl ester
4-phenethylamino-benzenesulfonic acid 2-[3-(2-morpholin-4-yl-ethyl)-ureido]-3H-benzimidazol-5-yl ester
4-phenethylamino-benzenesulfonic acid 2-[3-(2-methoxy-ethyl)-ureido]-3H-benzimidazol-5-yl ester
4-phenethylamino-benzenesulfonic acid 2-(3-ethyl-ureido)-3H-benzimidazol-5-yl ester
4-phenethylamino-benzenesulfonic acid 2-[3-(3-hydroxy-propyl)-ureido]-3H-benzimidazol-5-yl ester
4-(2-hydroxy-propylamino)-benzenesulfonic acid 2-[3-(2-morpholin-4-yl-ethyl)-ureido]-3H-benzimidazol-5-yl ester
4-(2-hydroxy-propylamino)-benzenesulfonic acid 2-(3-ethyl-ureido)-3H-benzimidazol-5-yl ester
4-(4-methoxy-benzylamino)-benzenesulfonic acid 2-[3-(2-morpholin-4-yl-ethyl)-ureido]-3H-benzimidazol-5-yl ester
4-(4-methoxy-benzylamino)-benzenesulfonic acid 2-(3-ethyl-ureido)-3H-benzimidazol-5-yl ester
4-(4-methoxy-benzylamino)-benzenesulfonic acid 2-(3-pyridin-2-ylmethyl-ureido)-3H-benzimidazol-5-yl ester
4-(4-methoxy-benzylamino)-benzenesulfonic acid 2-[3-(3-hydroxy-propyl)-ureido]-3H-benzimidazol-5-yl ester
4-(4-methoxy-benzylamino)-benzenesulfonic acid 2-[3-(2-methoxy-ethyl)-ureido]-3H-benzimidazol-5-yl ester
4-(2-pyrrolidin-1-yl-ethylamino)-benzenesulfonic acid 2-(3-ethyl-ureido)-3H-benzimidazol-5-yl ester
4-(2-pyrrolidin-1-yl-ethylamino)-benzenesulfonic acid 2-(3-pyridin-2-ylmethyl-ureido)-3H-benzimidazol-5-yl ester
4-(2-pyrrolidin-1-yl-ethylamino)-benzenesulfonic acid 2-[3-(2-methoxy-ethyl)-ureido]-3H-benzimidazol-5-yl ester
4-(1-phenyl-ethylamino)-benzenesulfonic acid 2-(3-ethyl-ureido)-3H-benzimidazol-5-yl ester
4-(2-diethylamino-ethylamino)-benzenesulfonic acid 2-(3-pyridin-2-ylmethyl-ureido)-3H-benzimidazol-5-yl ester
Thiophene-2-sulfonic acid 2-[3-(2-ethyl)-ureido]-1H-benzoimidazol-5-yl ester
Thiophene-2-sulfonic acid 2-[3-(2-methoxy-ethyl)-ureido]-1H-benzoimidazol-5-yl ester
Thiophene-2-sulfonic acid 2-[3-(2-morpholin-4-yl-ethyl)-ureido]-1H-benzoimidazol-5-yl ester
Thiophene-2-sulfonic acid 2-(3-pyridin-2-ylmethyl)-ureido]-1H-benzoimidazol-5-yl ester 4-{2-[3-(2-methoxy-ethyl)-ureido]-1H-benzoimidazol-5-yloxysulfonyl}-phenyl ester Benzoic acid 4-{2-[3-(2-morpholin-4-yl-ethyl)-ureido}-1H-benzoimidazol-5-yloxy-sulfonyl}-phenyl ester Benzoic acid 4-[2-([3-pyridin-2-ylmethyl)-ureido)-1H-benzoimidazol-5-yloxy-sulfonyl]-phenyl ester 2,6-difluoro-benzenesulfonic acid 2-(3-pyridin-2-ylmethyl-ureido)-3H-benzoimidazol-5-yl ester 2,6-difluoro-benzenesulfonic acid 3-(2-methoxy-ethyl)-3H-benzoimidazol-5-yl ester

DETAILED DESCRIPTION OF THE INVENTION

In still yet another embodiment is disclosed use of compounds of formula (I) for treating cancer diseases.

In still yet another embodiment is disclosed a method of inhibiting CDK4 enzymes in a mammal in recognized need of such treatment comprising administering to the mammal a therapeutically effective amount of compounds of formula (I).

In still yet another embodiment is disclosed a pharmaceutical composition which comprises a therapeutically effective amount of a compound of formula (I) in combination with a pharmaceutically acceptable carrier.

The term "pharmaceutically acceptable salt", as used herein, refers to salts, which are suitable for use in contact with the tissues of humans and lower animals. Pharmaceutically acceptable salts are described in detail in J. Pharmaceutical Sciences, 1977, 66:1 et seq. hereby incorporated by reference. Representative acid addition salts include acetate, citrate, aspartate, benzenesulfonate, hydrochloride, lactate, maleate, methanesulfonate, oxalate, and phosphate.

Chemical Synthesis

Compounds of the present invention can be easily prepared starting from 2-amino-5-(-4-fluorophenylsulfonyloxy)nitrobenzene, the process of preparation of which is described in U.S. Pat. No. 3,996,368.

In a first step this starting material is reacted with the amine bearing the R1 radical in a suitable solvent for carrying out the reaction. Among the list of solvents suitable for dissolving 2-amino-5-(-4-fluorophenylsulfonyloxy)nitrobenzene and the amine can be cited the glycols such as ethyl glycol, and the aprotic solvents such as dioxane, dimethylformamide, N-methylpyrrolidone. The preferred temperature for this reaction is comprised between room temperature and the reflux temperature. To recover the intermediate product it is preferred to precipitate the intermediate with hydrochloric acid.

In a second step the compound of step 1 is hydrogenated with hydrogen preferably in presence of Raney nickel (nitro group reduction method A) or palladium on carbon (nitro group reduction method B) in a suitable solvent choosen among the same list as for step 1 in mixture with an alcohol such as methanol. After reaction the catalyst is taken off by filtration.

In a third step the benzimidazole ring is closed by action of 1,3-bis(methoxycarbonyl)-2-methyl-2-thiopseudourea on the intermediate obtained in step 2 without intermediate separation. The reaction mixture is heated to reflux with stirring. The final product (methyl-benzimidazole-2-carbamate) is isolated after evaporation of the solvent under reduced pressure and solubilization in ethyl acetate then crystallisation. A final purification is carried out in methanol with a crystallisation in the same solvent.

Methyl-benzimidazole-2-carbamate can be converted to benzimidazole-2-ureas by treatment with an amine in a suitable solvent such as dimethylformamide, tetrahydrofuran or N-methylpyrrolidone in the presence of a base such as 1,8-diazabicyclo[5.4.0]undec-7-ene in a pressure vessel. The preferred temperature for this reaction is comprised between room temperature and 120° C.

tert-Butyl-benzimidazole-2-carbamate can be prepared by performing the third step described above using 1,3-bis(tert-butoxycarbonyl)-2-methyl-2-thiopseudourea instead of 1,3-bis(methoxycarbonyl)-2-methyl-2-thiopseudourea. These derivatives can be converted to the corresponding 2-aminobenzimidazole derivative using tert-butylcarbamate deprotection methods known by the persons skilled in the art. The 2-aminobenzimidazoles can be converted to the corresponding amides by reaction with carboxylic acid derivatives using methods known by the persons skilled in the art.

Formulations

The present invention also provides pharmaceutical compositions, which comprise compounds of the present invention formulated together with one or more non-toxic pharmaceutically acceptable carriers. The pharmaceutical compositions may be specially formulated for oral administration in solid or liquid form or for parenteral injection.

The term "parenteral", as used herein, refers to modes of administration, which include intravenous, intramuscular, intraperitoneal, subcutaneous and infusion.

Solid dosage forms for oral administration include capsules, tablets, pills, powders and granules. In such solid dosage forms, the active compound is mixed with at least one inert, pharmaceutically acceptable excipient or carrier.

Solid compositions of a similar type may also be employed as fillers in soft and hard-filled gelatin capsules.

The compounds of the present invention may be administered alone or mixed with other anticancer agents. Among the possible combinations, there may be mentioned alkylating agents and in particular cyclophosphamide, melphalan, ifosfamide, chlorambucil, busulfan, thiotepa, prednimustine, carmustine, lomustine, semustine, streptozotocin, decarbazine, temozolomide, procarbazine and hexamethylmelamine platinum derivatives such as in particular cisplatin, carboplatin or oxaliplatin, antibiotic agents such as in particular bleomycin, mitomycin, dactinomycin, antimicrotubule agents such as in particular vinblastine, vincristine, vindesine, vinorelbine, taxoids (paclitaxel and docetaxel), anthracyclines such as in particular doxorubicin, daunorubicin, idarubicin, epirubicin, mitoxantrone, losoxantrone, group I and II topoisomerases such as etoposide, teniposide, amsacrine, irinotecan, topotecan and tomudex, fluoropyrimidines such as 5-fluorouracil, UFT, floxuridine, cytidine analogues such as 5-azacytidine, cytarabine, gemcitabine, 6-mercaptomurine, 6-thioguanine, adenosine analogues such as pentostatin, cytarabine or fludarabine phosphate, methotrexate and folinic acid, various enzymes and compounds such as L-asparaginase, hydroxyurea, trans-retinoic acid, suramine, dexrazoxane, amifostine, herceptin as well as oestrogenic and androgenic hormones.

It is also possible to combine a radiation treatment with the compounds of the present invention. This treatment may be administered simultaneously, separately or sequentially. The treatment will be adapted to the patient to be treated by the practitioner.

The invention will be more fully described by the following examples, which must not be considered as a limitation of the invention.

EXAMPLES

Method for Analytical Determination

Liquid Chromatography Coupled to Mass Spectrometry (LC/MS) Analysis LC/MS analyses were conducted on a Micromass instrument model LCT linked to an HP 1100 model instrument. Compound abundance was detected using an HP G1315A (model) photodiode array detector in the 200–600 nm wavelength range and a Sedex 65 (model) evaporative light scattering detector. Mass spectra were acquired in the 160 to 2000 amu range. Data were analysed using the Micromass MassLynx software. Separation were carried out on a Hypersil Highpurity C18, 5 μm particle size column (50×4.6 mm) eluted by a linear gradient of 10 to 90% acetonitrile containing 0.05% (v/v) trifluoroacetic acid (TFA) in water containing 0.05% (v/v) TFA in 6.50 min at a flow rate of 1 ml/min.

Method for Purification

LC/MS Triggered Purification

Compounds were purified by LC/MS using a Waters FractionLynx system composed of a Waters model 600 gradient pump, a Waters model 515 regeneration pump, a Waters Reagent Manager make-up pump, a Waters model 2700 sample manager autoinjector, two Rheodyne model LabPro switches, a Waters model 996 photodiode array detector, a Waters model ZMD mass spectrometer and a Gilson model 204 fraction collector. The Waters FractionLynx software controlled the instrument. Separation were conducted alternatively on two Waters Symmetry columns ($C_{18}$, 5 μM, 19×50 mm, catalogue number 186000210), one column was under regeneration by a 95/5 (v/v) water/acetonitrile mixture containing 0.07% TFA (v/v) while the other one is separating. Columns were eluted by a linear gradient of acetonitrile containing 0.07% (v/v) TFA in water containing 0.07% (v/v) TFA, from 5 to 95% (v/v) in 8 min and 2 min at 95% acetonitrile containing 0.07% (v/v) TFA, at a flow rate of 10 ml/min. At the output of the separating column the flow was split to the 1/1000 ratio using a LC Packing AccuRate splitter; 1/1000 of the flow was mixed with methanol (0.5 ml/min. flow rate) and sent to the detectors, this flow was split again ¾ of the flow was sent to the photodiode array detector and ¼ to the mass spectrometer; the rest of the output of the column (999/1000) was sent to the fraction collector were flow was directed normally to waste unless expected mass signal was detected by the FractionLynx software. The FractionLynx software was supplied with molecular formulas of expected compounds and triggered the collection of compounds when mass signal corresponding to $[M+H]^+$ and $[M+Na]^+$ are detected. In certain cases (depending on analytical LC/MS result, when $[M+2H]^{++}$ was detected as an intense ion) the FractionLynx software was additionally supplied with calculated half molecular weight (MW/2), in these conditions collection was also triggered when mass signal corresponding to $[M+2H]^{++}$ and $[M+Na+H]^{++}$ are detected. Compounds were collected in tarred glass tubes. After collection, solvent was evaporated in a Jouan model RC 10.10 centrifuge evaporator or a Genevac model HT8 centrifuge evaporator and the amount of compound was determined by weighing of the tubes after solvent evaporation.

Method of Preparation of Compounds of the Invention 2-amino-5-(4-fluorophenylsulfonyloxy)nitrobenzene (melting point 161° C.), the starting material, can be prepared according to U.S. Pat. No. 3,996,368.

Example 1

Preparation of Methyl-5-(4-[2-hydroxyethyl]aminophenylsulfonyloxy)benzimidazole-2-carbamate

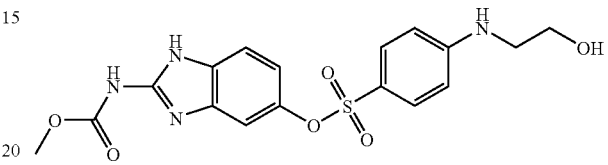

step 1: 15.6 g of 2-amino-5-(4-fluorophenylsulfonyloxy) nitrobenzene were combined with 25 ml ethanolamine in 100 ml ethyl glycol in a round bottom flask. The reaction mixture was heated to reflux for 90 min and then cooled on ice. Reaction mixture was then diluted with 250 ml of 2N aqueous HCl, the compound precipitated and was filtered off with suction. The preciptate was the washed with water and dried, yielding 15.5 g of 2-amino-5-(4-[2-hydroxyethyl] aminophenylsulfonyloxy)nitrobenzene (melting point 180° C.).

step 2: 15.5 g of 2-amino-5-(4-[2-hydroxyethyl]aminophenylsulfonyloxy)nitrobenzene in 75 ml of methanol and 75 ml of dimethylformamide are hydrogenated under atmospheric pressure with a catalytic amount of Raney Nickel (method A). After hydrogen uptake is complete, the catalyst was filtered off with suction, washed with methanol and the filtrate is concentred under reduced pressure step 3: concentrated filtrate of step 2 was taken up in 150 ml methanol and 30 ml of glacial acetic acid, 10.3 g of 1,3-bis(methoxycarbonyl)-2-methyl-2-thiopseudourea was added and reaction mixture was heated to reflux with stirring for 3 hours. Solvents were then evaporated under reduced pressure, concentrate was then dissolved in hot ethylacetate, crystallized by cooling and washed with ethylacetate. Compound was then solubilized in 250 ml refluxing methanol, crystallized by cooling and washed with methanol and dried yielding 7.4 g of the title compound. (Melting point 170° C., LC/MS analysis: retention time=2.8 min., mass spectrum: 407.24, $[M+H]^+$)

Example 2

Preparation of Methyl-5-(4-[4-hydroxbutyl]aminophenylsulfonyloxy)benzimidazole-2-carbamate

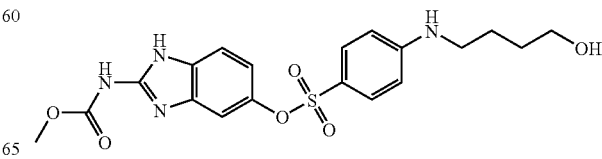

step 1: 19.7 g of 2-amino-5-(4-fluorophenylsulfonyloxy) nitrobenzene were combined with 20 g butanolamine in 200 ml N-methylpyrrolidinone in a round bottom flask. The reaction mixture was heated to reflux for 120 min and then solvent was evaporated under reduced pressure. Concentrate was then solubilized with ethylacetate and extracted with 2N aqueous HCl and water and then dried over sodium sulfate and dried under reduced pressure. The concentrate was recrystallized in isopropanol, filtered under suction, washed with isopropanol and dried, yielding 13.1 g of 2-amino-5-(4-[4-hydroxbuyl]aminophenylsulfonyloxy)nitrobenzene (melting point 105° C.).

step 2: 13.1 g of 2-amino-5-(4-[4-hydroxbutyl]aminophenylsulfonyloxy)nitrobenzene in 75 ml of methanol and 75 ml of dimethylformamide are hydrogenated under atmospheric pressure with a catalytic amount of Raney Nickel (Method A). After hydrogen uptake is complete, the catalyst was filtered off with suction, washed with methanol and the filtrate is concentred under reduced pressure.

step 3: concentrated filtrate of step 2 was taken up in 100 ml methanol and 20 ml of glacial acetic acid, 8.2 g of 1,3-bis(methoxycarbonyl)-2-methyl-2-thiopseudourea was added and reaction mixture was heated to reflux with stirring for 3 hours. Solvents were then evaporated under reduced pressure, concentrate washed with 2N aqueous ammonia, water and dried. Concentrate was then dissolved in hot ethyl acetate, crystallized by cooling and washed with ethyl acetate. Compound was then solubilized in refluxing methanol, crystallized by cooling and washed with methanol and dried yielding 6.3 g of the title compound. (Melting point 180° C., LC/MS analysis: retention time=2.9 min., mass spectrum: 435.29, [M+H]$^+$)

Example 3

Preparation of Methyl-5-(4-[2-methoxyethyl]aminophenylsulfonyloxy)benzimidazole-2-carbamate

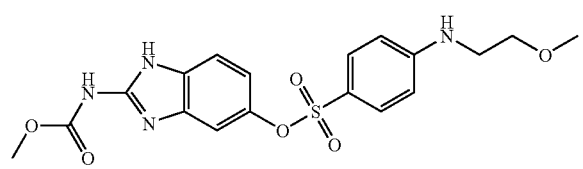

step 1: 15.6 g of 2-amino-5-(4-fluorophenylsulfonyloxy) nitrobenzene were combined with 35 ml methoxyethylamine in 100 ml dioxane in a round bottom flask. The reaction mixture was heated to reflux for 8 hours and then cooled to 40° C. and extracted two times with 250 ml water. Concentrate was solubilized with ethyl acetate and extracted with 2N aqueous HCl and water, the organic phase was then dried under reduced pressure, yielding 19.2 g of 2-amino-5-(4-[2-methoxyethyl]aminophenylsulfonyloxy)nitrobenzene (melting point 105° C.).

step 2: 18.2 g of 2-amino-5-(4-[2-methoxyethyl]aminophenylsulfonyloxy)nitrobenzene in 75 ml of methanol and 75 ml of dimethylformamide are hydrogenated under atmospheric pressure with a catalytic amount of Raney Nickel (Method A). After hydrogen uptake is complete, the catalyst was filtered off with suction, washed with methanol and the filtrate is concentred under reduced pressure.

step 3: concentrated filtrate of step 2 was taken up in 150 ml methanol and 25 ml of glacial acetic acid, 12.3 g of 1,3-bis(methoxycarbonyl)-2-methyl-2-thiopseudourea was added and reaction mixture was heated to reflux with stirring for 3 hours. Solvents were then evaporated under reduced pressure, and concentrate was crystallized with methanol saturated with ammonia, washed with water, methanol and dried, yielding 12 g of the title compound. (Melting point 155° C., LC/MS analysis: retention time=3.1 min., mass spectrum: 421.25, [M+H]$^+$).

Example 4

Preparation of Methyl-5-(4-[1-imidazolyl]-phenylsulfonyloxy)benzimidazole-2-carbamate

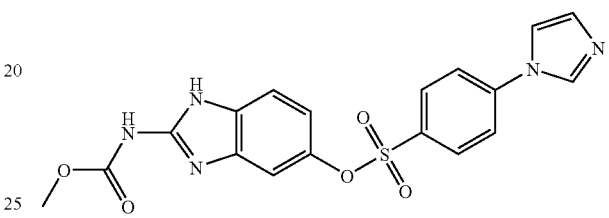

step 1: 15.6 g of 2-amino-5-(4-fluorophenylsulfonyloxy) nitrobenzene were combined with 20.7 g imidazole in 100 ml dimethylformamide in a round bottom flask. The reaction mixture was heated to reflux for 3 hours and then cooled to room temperature. Reaction mixture was then precipitated by addition of water filtered and precipitate was washed with water and dried. Residue was resolubilized in hot ethyl glycol, crystallized by cooling and the crystals were washed with methanol and dried, yielding 10.4 g of 2-amino-5-(4-[1-imidazolyl]-phenylsulfonyloxy)nitro-benzene (melting point 209° C.).

step 2: 10.4 g of 2-amino-5-(4-[1-imidazolyl]-phenylsulfonyloxy)nitrobenzene in 75 ml of methanol and 75 ml of dimethylformamide are hydrogenated under atmospheric pressure with a catalytic amount of Raney Nickel. After hydrogen uptake is complete, the catalyst was filtered off with suction, washed with methanol and the filtrate is concentred under reduced pressure (Method A). Alternatively 5 g of 2-amino-5-(4-[1-imidazolyl]-phenylsulfonyloxy)nitrobenzene in 475 ml of methanol and 25 ml of dimethylformamide are hydrogenated under 5 bars pressure with 10% (w/w) of palladium on carbon at 30° C. during 6 hours (Method B) yielding 4.18 g (91%) of expected product.

step 3: concentrated filtrate of step 2 was taken up in 150 ml methanol and 25 ml of glacial acetic acid, 10.3 g of 1,3-bis(methoxycarbonyl)-2-methyl-2-thiopseudourea was added and reaction mixture was heated to reflux with stirring for 3 hours. After cooling to room temperature reaction mixture was precipitated by addition of ethyl acetate, filtered by suction and washed by ethyl acetate. Filtrate was then resolubilized with 50 ml dimethylformamide and 250 ml of methanol was added. Mixture crystallised upon cooling and crystals were washed with methanol and dried under reduced pressure, yielding 9.4 g of the title compound. (Melting point 258° C., LC/MS analysis: retention time=2.5 min., mass spectrum: 414.23, [M+H]$^+$; 382.19 fragmentation of carbamate: loss of methanol, NMR, IR).

Example 5

Preparation of Methyl-5-(4-[2-pyridylmethyl]aminophenylsulfonyloxy)benzimidazole-2-carbamate

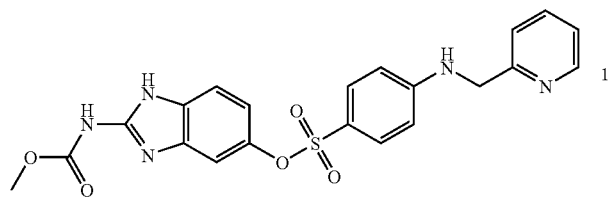

In a similar manner to examples 1 to 4, title compound was obtained by reacting 2-aminomethylpyridine with 2-amino-5-(4-fluorophenylsulfonyloxy)nitrobenzene at step 1 of the procedure described above and using nitro group reduction method A. (LC/MS analysis: retention time=2.6 min., mass spectrum: 454.28, [M+H]$^+$; 907.53, [2M+H]$^+$; 422.24, fragmentation of carbamate: loss of methanol).

Example 6

Preparation of Methyl-5-(4-ethylaminophenylsulfonyloxy)benzimidazole-2-carbamate

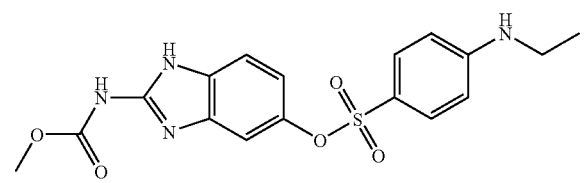

In a similar manner to examples 1 to 4, title compound was obtained by reacting ethylamine with 2-amino-5-(4-fluorophenylsulfonyloxy)nitrobenzene at step 1 of the procedure described above and using nitro group reduction method A. (LC/MS analysis: retention time=3.2 min., mass spectrum: 390.98, [M+H]$^+$).

Example 7

Preparation of Methyl-5-(4-[N-Glycinyl]-phenylsulfonyloxy)benzimidazole-2-carbamate

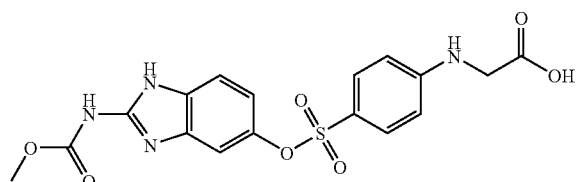

In a similar manner to examples 1 to 4, title compound was obtained by reacting glycine with 2-amino-5-(4-fluorophenylsulfonyloxy)nitrobenzene at step 1 of the procedure described above and using nitro group reduction method A. (LC/MS analysis: retention time=2.8 min., mass spectrum: 421.21, [M+H]$^+$).

Example 8

Preparation of Methyl-5-(4-[1-methyl,2-hydroxyethyl]aminophenylsulfonyloxy)benzimidazole-2-carbamate

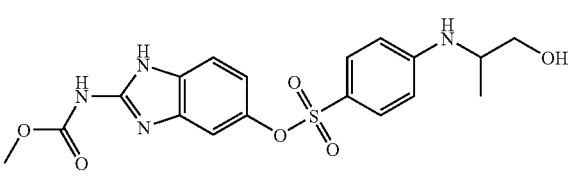

In a similar manner to examples 1 to 4, title compound was obtained by reacting 2-aminopropanol with 2-amino-5-(4-fluorophenylsulfonyloxy)nitrobenzene at step 1 of the procedure described above and using nitro group reduction method A. (LC/MS analysis: retention time=2.9 min., mass spectrum: 421.27, [M+H]$^+$).

Example 9

Preparation of Methyl-5-(4-[2-methyl,2-hydroxyethyl]aminophenylsulfonyloxy)benzimidazole-2-carbamate

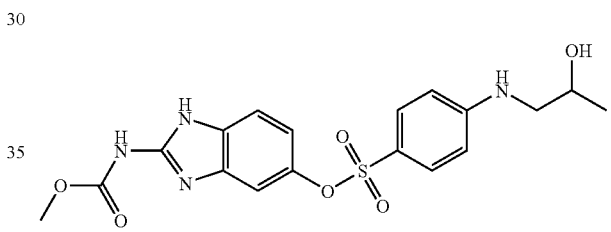

In a similar manner to examples 1 to 4, title compound was obtained by reacting 1-methyl-2-aminoethanol with 2-amino-5-(4-fluorophenylsulfonyloxy)nitrobenzene at step 1 of the procedure described above and using nitro group reduction method A. (LC/MS analysis: retention time=2.9 min., mass spectrum: 421.27, [M+H]$^+$).

Example 10

Preparation of Methyl-5-(4-isopropylaminophenylsulfonyloxy)benzimidazole-2-carbamate

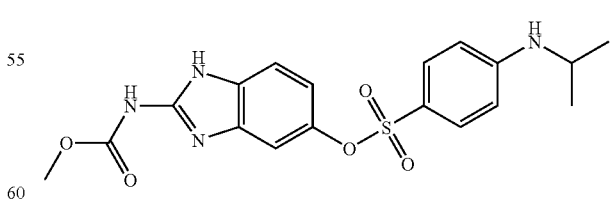

In a similar manner to examples 1 to 4, title compound was obtained by reacting isopropylamine with 2-amino-5-(4-fluorophenylsulfonyloxy)nitrobenzene at step 1 of the procedure described above and using nitro group reduction method A. (LC/MS analysis: retention time=3.4 min., mass spectrum: 405.27, [M+H]$^+$).

Example 11

Preparation of Methyl-5-(4-[1-ethyl, 2-hydroxy-ethyl]aminophenylsulfonyloxy)benzimidazole-2-carbamate

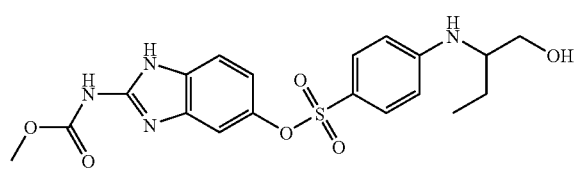

In a similar manner to examples 1 to 4, title compound was obtained by reacting 2-aminobutanol with 2-amino-5-(4-fluorophenylsulfonyloxy)nitrobenzene at step 1 of the procedure described above and using nitro group reduction method A. (LC/MS analysis: retention time=3.0 min., mass spectrum: 435.30, [M+H]$^+$).

Example 12

Preparation of Methyl-5-(4-butylaminophenylsulfonyloxy)benzimidazole-2-carbamate

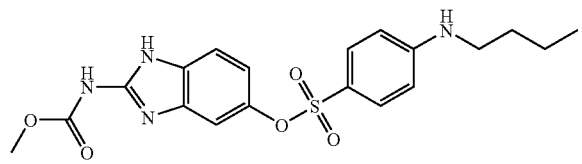

In a similar manner to examples 1 to 4, title compound was obtained by reacting butylamine with 2-amino-5-(4-fluorophenylsulfonyloxy)nitrobenzene at step 1 of the procedure described above and using nitro group reduction method A. (LC/MS analysis: retention time=3.6 min., mass spectrum: 419.25, [M+H]$^+$).

Example 13

Preparation of Methyl-5-(4-[3-methoxypropyl]aminophenyl-sulfonyloxy)benzimidazole-2-carbamate

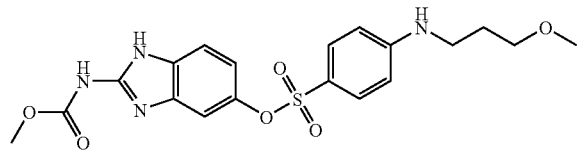

In a similar manner to examples 1 to 4, title compound was obtained by reacting 3-methoxypropanolamine with 2-amino-5-(4-fluorophenylsulfonyloxy)nitrobenzene at step 1 of the procedure described above and using nitro group reduction method A. (LC/MS analysis: retention time=3.2 min., mass spectrum: 435.27, [M+H]$^+$).

Example 14

Preparation of Methyl-5-(4-methylaminophenylsulfonyloxy)benzimidazole-2-carbamate

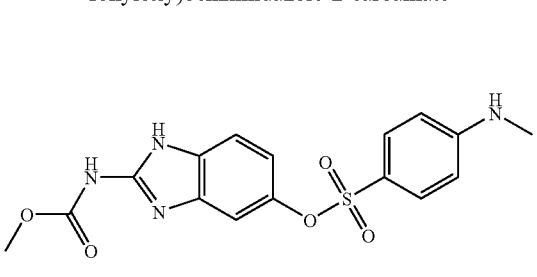

In a similar manner to examples 1 to 4, title compound was obtained by reacting methylamine with 2-amino-5-(4-fluorophenylsulfonyloxy)nitrobenzene at step 1 of the procedure described above and using nitro group reduction method A. (LC/MS analysis: retention time=3.0 min., mass spectrum: 377.22, [M+H]$^+$).

Example 15

Preparation of Methyl-5-(4-[2-sulfonylethyl]aminophenylsulfonyloxy)benzimidazole-2-carbamate

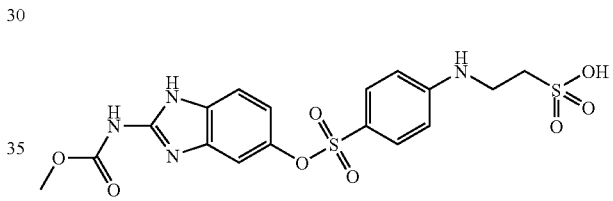

In a similar manner to examples 1 to 4, title compound was obtained by reacting 2-aminoethanesulfonic acid with 2-amino-5-(4-fluorophenylsulfonyloxy)nitrobenzene at step 1 of the procedure described above and using nitro group reduction method A. (LC/MS analysis: retention time=2.6 min., mass spectrum: 471.19, [M+H]$^+$; 941.41, [2M+H]$^+$).

Example 16

Preparation of Methyl-5-(4-aminophenylsulfonyloxy)benzimidazole-2-carbamate

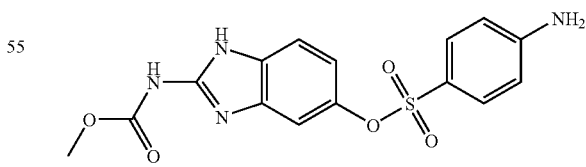

In a similar manner to examples 1 to 4, title compound was obtained by reacting ammonia with 2-amino-5-(4-fluorophenylsulfonyloxy)nitrobenzene at step 1 of the procedure described above and using nitro group reduction method A. (LC/MS analysis: retention time=2.9 min., mass spectrum: 363.19, [M+H]$^+$).

Example 17

Preparation of Methyl-5-(4-[2-diethylaminoethyl]aminophenyl-sulfonyloxy)benzimidazole-2-carbamate

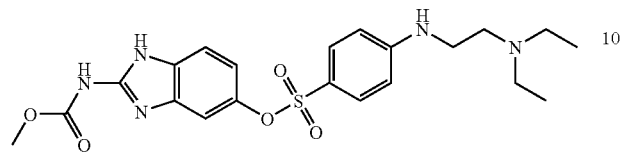

In a similar manner to examples 1 to 4, title compound was obtained by reacting 2-diethylaminoethylamine with 2-amino-5-(4-fluorophenylsulfonyloxy)nitrobenzene at step 1 of the procedure described above and using nitro group reduction method A. (LC/MS analysis: retention time=2.6 min., mass spectrum: 462.34, [M+H]$^+$; 923.65, [2M+H]$^+$; 430.30, fragmentation of carbamate: loss of methanol).

Example 18

Preparation of Methyl-5-(4-[1-tetrathydrofurylmethyl]aminophenyl-sulfonyloxy)benzimidazole-2-carbamate

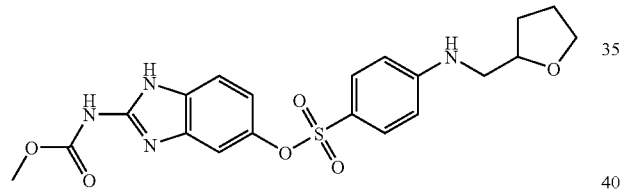

In a similar manner to examples 1 to 4, title compound was obtained by reacting tetrahydrofurfurylamine with 2-amino-5-(4-fluorophenylsulfonyloxy)nitrobenzene at step 1 of the procedure described above and using nitro group reduction method A. (LC/MS analysis: retention time=3.2 min., mass spectrum: 447.24, [M+H]$^+$).

Example 19

Preparation of Methyl-5-(4-cyclopentylaminophenylsulfonyloxy)benzimidazole-2-carbamate

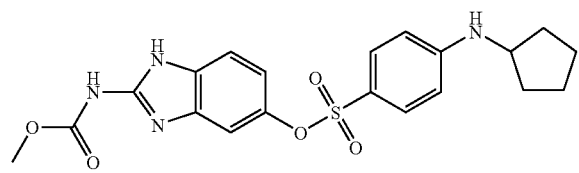

In a similar manner to examples 1 to 4, title compound was obtained by reacting cyclopentylamine with 2-amino-5-(4-fluorophenylsulfonyloxy)nitrobenzene at step 1 of the procedure described above and using nitro group reduction method A. (LC/MS analysis: retention time=3.6 min., mass spectrum: 431.29, [M+H]$^+$).

Example 20

Preparation of Methyl-5-(4-[2-phenylethyl]aminophenylsulfonyloxy)benzimidazole-2-carbamate

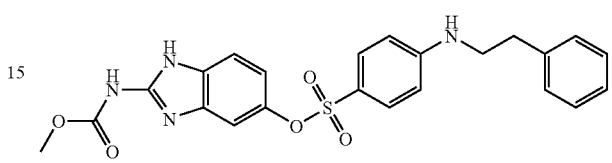

In a similar manner to examples 1 to 4, title compound was obtained by reacting phenethylamine with 2-amino-5-(4-fluorophenylsulfonyloxy)nitrobenzene at step 1 of the procedure described above and using nitro group reduction method A. (LC/MS analysis: retention time=3.6 min., mass spectrum: 467.26, [M+H]$^+$).

Example 21

Preparation of 5-(4-[1-imidazolyl]-phenylsulfonyloxy)-1H-benzimidazole-2-ylamine: an intermediate for amide product synthesis

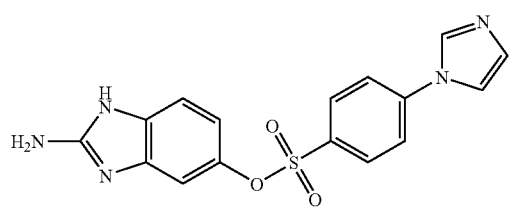

For step 1 and 2, intermediate of title compound is obtained in similar manner to step 1 end 2 of example 4.

step 3: 8 g of step 2 compound were taken up in 128 ml methanol and 21.6 ml acetic acid in a 250 ml round bottom flask. Mixture was heated to reflux and 9.13 g of 1,3-bis(tert-butoxycarbonyl)-2-methyl-2-thiopseudourea was added. Reaction mixture was heated to reflux with stirring for 4 hours. Solid was obtained by cooling to 0° C. for one hour and washed with ethyl acetate, triturated and dried on a glass frit yielding 7.55 g compound.

step 4: Compound of step 3 was taken up in 80 ml dichloromethane and 40 ml trifluoroacetic acid. Reaction mixture was stirred for 4 hours at room temperature. Solvents were evaporated under reduced pressure. Concentrated filtrate was taken in 75 ml water and 50 ml of sodium carbonate aqueous solution (10% w/w). Precipitate obtained was washed with dichloromethane and dried on a glass frit yielding 5.3 g title compound.

Example 22

Preparation of 5-(4-cyclopentylaminophenylsulfonyloxy)-1H-benzimidazole-2-ylamine: an intermediate for amide product synthesis

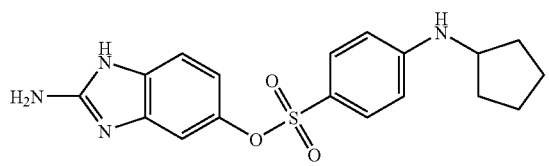

For step 1 and 2, intermediate of title compound is obtained in similar manner to step 1 end 2 of example 19.

For step 3 and 4, title compound is obtained in similar manner to example 21.

Example 23

Preparation of N-[5-(4-Imidazol-1-yl-benzenesulfonyloxy)-1H-benzoimidazol-2-yl]-succinamic acid methyl ester

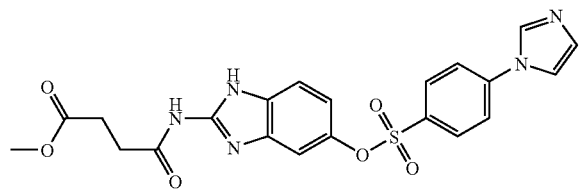

step 1: 8.9 mg of succinamic acid methyl ester, 25 mg of 2-(1H-benzotriazole-1-yl)-1,1,3,3-tetramethyluronium hexafluorophosphate (HBTU) and 12 µl diisopropyl-ethylamine were taken up in 0.4 ml dimethylformamide. Reaction mixture was stirred at room temperature for one hour and 5-(4-[1-imidazolyl]-phenylsulfonyloxy)-1H-benzimidazole-2-ylamine was added in 0.2 ml dimethylformamide. Reaction mixture was then stirred at room temperature for 24 hours. Solvent was evaporated in a Jouan model RC 10.10 centrifuge evaporator and title compound was solubilised in 0.5 ml dimethylsulfoxide for LCMS trigged purification yielding 3.9 mg of N-[5-(4-[1-imidazolyl]-phenylsulfonyloxy)-1H-benzimidazole-2-yl]-succinamic-acid-methyl ester. (LC/MS analysis: retention time=2.70 min., mass spectrum: 470.34, [M+H]$^+$).

Example 24

Preparation of 4-Cyclopentylamino-benzenesulfonic acid 2-(2-tert-butoxycarbonylamino-acetylamino)-1H-benzoimidazol-5-yl ester

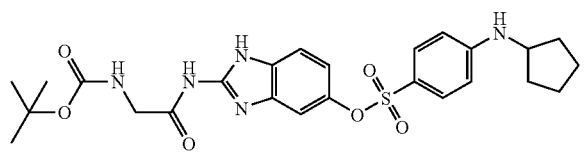

step 1: 11.3 mg of N-(tert-butoxycarbonyl)glycine, 25 mg HBTU and 12 µl diisopropylethylamine were taken up in 0.4 ml dimethylformamide. Reaction mixture was stirred at room temperature for one hour and 5-(4-cyclopentylaminophenylsulfonyloxy)-1H-benzimidazole-2-ylamine was added in 0.2 ml dimethylformamide. Reaction mixture was then stirred at room temperature for 24 hours. Solvent was evaporated in a Jouan model RC 10.10 centrifuge evaporator and title compound was solubilised in 0.5 ml dimethylsulfoxide for LCMS trigged purification yielding 2.4 mg of N-[5-(4-cyclopentylaminophenylsulfonyloxy)-1H-benzimidazole-2-yl]-tert-butoxycarbonylglycineamid. (LC/MS analysis: retention time=3.87 min., mass spectrum: 530.38, [M+H]$^+$).

Example 25

Preparation of N-[5-(4-Cyclopentylamino-benzenesulfonyloxy)-1H-benzoimidazol-2-yl]-succinamic acid methyl ester

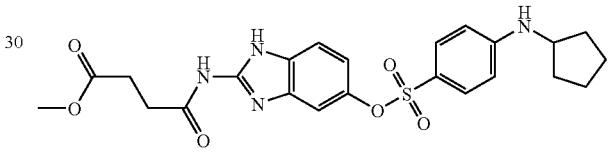

In a similar manner to example 24, title compound was obtained by reacting succinamic acid methyl ester with N-5-(4-cyclopentylaminophenylsulfonyloxy)-1H-benzimidazole-2-ylamine (LC/MS analysis: retention time=3.72 min., mass spectrum: 487.34, [M+H]$^+$).

Example 26

Preparation of 4-[5-(4-Cyclopentylamino-benzenesulfonyloxy)-1H-benzoimidazol-2-ylcarbamoyl]-butyric acid methyl ester

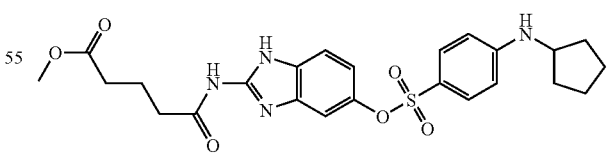

In a similar manner to example 24, title compound was obtained by reacting butyric acid methylester with N-5-(4-cyclopentylaminophenylsulfonyloxy)-1H-benzimidazole-2-ylamine. (LC/MS analysis: retention time=3.75 min., mass spectrum: 501.36, [M+H]$^+$).

Example 27

Preparation of 4-Cyclopentylamino-benzenesulfonic acid 2-(cyclopropanecarbonyl-amino)-1H-benzoimidazol-5-yl ester

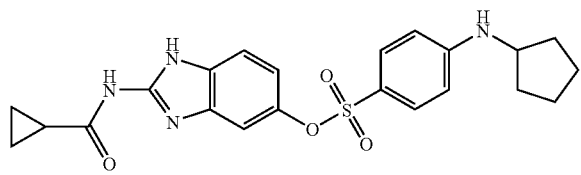

In a similar manner to example 24, title compound was obtained by reacting cyclopropane carboxylic acid with 5-(4-cyclopentylaminophenylsulfonyloxy)-1H-benzimidazole- 2-ylamine. (LC/MS analysis: retention time=3.76 min., mass spectrum: 441.36, [M+H]$^+$).

Example 28

Preparation of 4-Cyclopentylamino-benzenesulfonic acid 2-(2-methoxy-acetylamino)-1H-benzoimidazol-5-yl ester

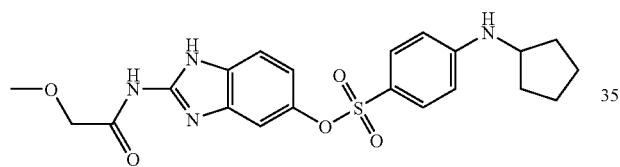

In a similar manner to example 24, title compound was obtained by reacting methoxyaceticacid with 5-(4-cyclopentylaminophenylsulfonyloxy)-1H-benzimidazole-2-ylamine. (LC/MS analysis: retention time=3.66 min., mass spectrum: 445.34, [M+H]$^+$).

Example 29

Preparation of 4-Cyclopentylamino-benzenesulfonic acid 2-(2-dimethylamino-acetylamino)-1H-benzoimidazol-5-yl ester

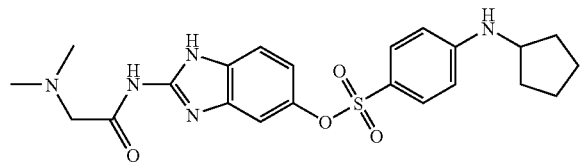

In a similar manner to example 24, title compound was obtained by reacting N,N-dimethylglycine with 5-(4-cyclopentylaminophenylsulfonyloxy)-1H-benzimidazole-2-ylamine. (LC/MS analysis: retention time=3.36 min., mass spectrum: 458.36, [M+H]$^+$).

Example 30

N-[5-(4-[imidazolyl]-phenylsulfonyloxy)-1H-benzimidazole-2-yl]-methylurea

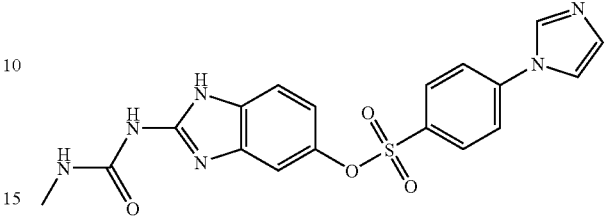

10 mg of methyl-5-(4-[imidazolyl]-phenylsulfoxy)benzimidazole-2-carbamate (example 4) were combined with 50 µl methylamine (2.0 M in tetrahydrofuran) and 5 µl 1,8-Diazabicyclo[5.4.0]undec-7-ene in 2 ml N-methylpyrrolidone/tetrahydrofuran (1/1) in a 24 well Inox plate for high pressure reaction. The reaction mixture was put under a 10 Bars argon pressure and then heated to 80° C. for 4 hours, and then cooled at room temperature. Compounds were put in an assay tube and tetrahydrofuran was evaporated under reduced pressure and compound in N-methylpyrrolidone were directly purified by preparative LCMS under conditions described above. After purification, solution was dry-concentrated in a JOUAN RC1010 evaporator. (LC/MS analysis: retention time=2.23 min., mass spectrum: 413.23, [M+H]$^+$).

Example 31

N-[5-(4-cyclopentylaminophenylsulfonyloxy)-1H-benzimidazole-2-yl]-methylurea

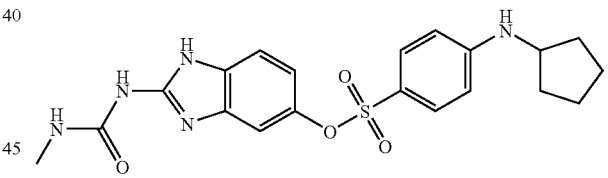

In a similar manner to example 30, title compound was obtained by reacting methyl-5-(4-cyclopentylaminophenylsulfonyloxy)benzimidazole-2-carbamate (example 19) with methylamine (2.0 M in tetrahydrofuran). (LC/MS analysis: retention time=3.30 min., mass spectrum: 430.27, [M+H]$^+$).

Example 32

N-[5-(4-cyclopentylaminophenylsulfonyloxy)-1H-benzimidazole-2-yl]-dimethylurea

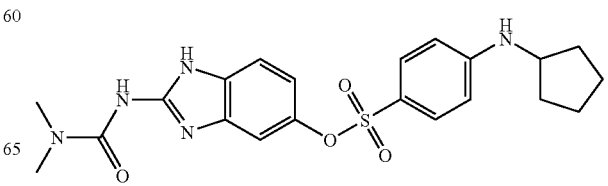

Title compound was obtained by reacting 10 mg of methyl-5-(4-cyclopentylaminophenylsulfonyloxy)benzimidazole-2-carbamate (example 19) with 50 µl dimethylamine (2.0 M in tetrahydrofuran) and 5 µl 1,8-diazabicyclo[5.4.0]undec-7-ene in 2 ml dimethylformamide in a 24 well Inox plate for high pressure reaction. The reaction mixture was put under a 10 Bars argon pressure and then heated to 80° C. for 4 hours, and then cooled at room temperature. Compounds were put in an assay tube and dimethylformamide was evaporated in a JOUAN RC1010 evaporator. Compound was diluted in 0.5 ml dimethylsulfoxide for LC/MS trigged purification yielding 9 mg of the title compound (LC/MS analysis: retention time=3.35 min., mass spectrum: 444.29, [M+H]+).

Example 33

4-Cyclopentylamino-benzenesulfonic acid 2-(3-cyclopropyl-ureido)-1H-benzoimidazol-5-yl ester

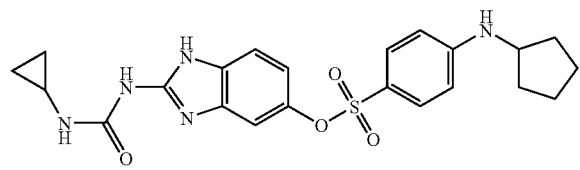

10 mg of methyl-5-(4-cyclopentylaminophenylsulfonyloxy)benzimidazole-2-carbamate (example 19) were combined with 25 µl cyclopropylamine and 10 µl 1,8-diazabicyclo[5.4.0]undec-7-ene in 2 ml N-methylpyrrolidone/tetrahydrofuran (0.8/1.2) in a 24 well Inox plate for high pressure reaction. The reaction mixture was put under a 10 Bars argon pressure and then heated to 60° C. for 40 hours, and then cooled to room temperature. Compounds were put in an assay tube, tetrahydrofuran was evaporated under reduced pressure and compound in N-methylpyrrolidone was directly purified by LC/MS trigged purification yielding 8.7 mg title compound. (LC/MS analysis: retention time=3.66 min., mass spectrum: 456.36, [M+H]+).

Example 34

4-Cyclopentylamino-benzenesulfonic acid 2-(3-isopropyl-ureido)-1H-benzoimidazol-5-yl ester

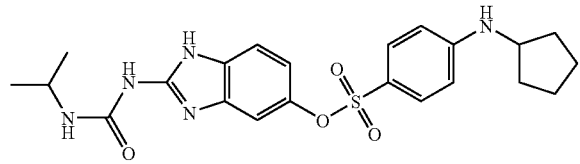

In a similar manner to example 33, title compound was obtained by reacting methyl-5-(4-cyclopentylaminophenyl-sulfonyloxy)benzimidazole-2-carbamate (example 19) with isopropylamine. (LC/MS analysis: retention time=3.78 min., mass spectrum: 458.36, [M+H]+).

Example 35

4-Cyclopentylamino-benzenesulfonic acid 2-(3-butyl-ureido)-1H-benzoimidazol-5-yl ester

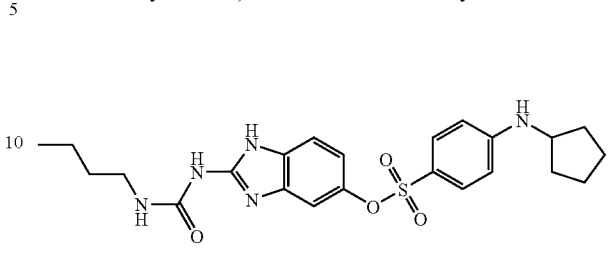

In a similar manner to example 33, title compound was obtained by reacting methyl-5-(4-cyclopentylaminophenyl-sulfonyloxy)benzimidazole-2-carbamate (example 19) with butylamine. (LC/MS analysis: retention time=3.90 min., mass spectrum: 472.39, [M+H]+).

Example 36

4-Imidazol-1-yl-benzenesulfonic acid 2-[3-(2-fluoro-phenyl)-ureido]-1H-benzoimidazol-5-yl ester

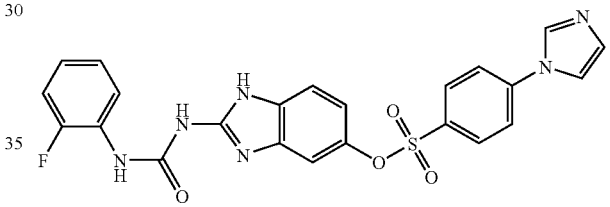

In a similar manner to example 30, title compound was obtained by reacting methyl-5-(4-[imidazolyl]-phenylsulfoxy)benzimidazole-2-carbamate (example 4) with 2-fluoro-aniline. (LC/MS analysis: retention time=3.03 min., mass spectrum: 493.28, [M+H]+).

Example 37

4-Cyclopentylamino-benzenesulfonic acid 2-[3-(2-fluoro-phenyl)-ureido]-1H-benzoimidazol-5-yl ester

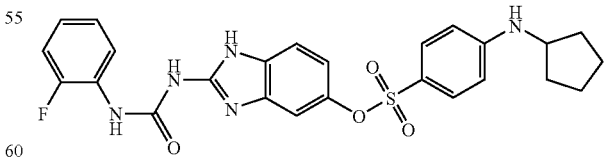

In a similar manner to example 33, title compound was obtained by reacting methyl-5-(4-cyclopentylaminophenyl-sulfonyloxy)benzimidazole-2-carbamate (example 19) with 2-fluoro-aniline. (LC/MS analysis: retention time=3.99 min., mass spectrum: 510.32, [M+H]+).

Example 38

4-Cyclopentylamino-benzenesulfonic acid 2-[3-(3-methoxy-phenyl)-ureido]-1H-benzoimidazol-5-yl ester

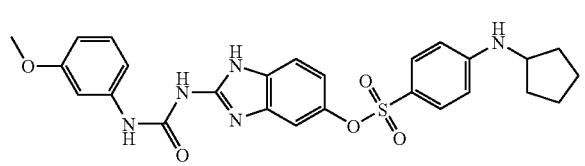

In a similar manner to example 33, title compound was obtained by reacting methyl-5-(4-cyclopentylaminophenyl-sulfonyloxy)benzimidazole-2-carbamate (example 19) with m-anisidine (LC/MS analysis: retention time=4.02 min., mass spectrum: 522.33, [M+H]$^+$).

Example 39

4-Cyclopentylamino-benzenesulfonic acid 2-[3-(4-methoxy-phenyl)-ureido]-1H-benzoimidazol-5-yl ester

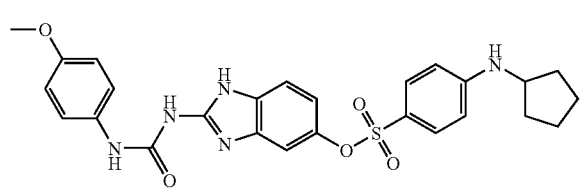

In a similar manner to example 33, title compound was obtained by reacting methyl-5-(4-cyclopentylaminophenyl-sulfonyloxy)benzimidazole-2-carbamate (example 19) with p-anisidine (LC/MS analysis: retention time=3.97 min., mass spectrum: 522.34, [M+H]$^+$).

Example 40

4-Cyclopentylamino-benzenesulfonic acid 2-[3-(4-chloro-phenyl)-ureido]-1H-benzoimidazol-5-yl ester

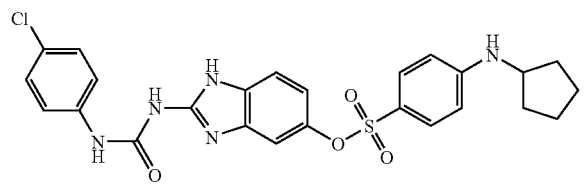

In a similar manner to example 33, title compound was obtained by reacting methyl-5-(4-cyclopentylaminophenyl-sulfonyloxy)benzimidazole-2-carbamate (example 19) with 4-chloroaniline. (LC/MS analysis: retention time=4.20 min., mass spectrum: 526.28, [M+H]$^+$).

Example 41

4-Cyclopentylamino-benzenesulfonic acid 2-[3-(3-fluoro-benzyl)-ureido]-1H-benzoimidazol-5-yl ester

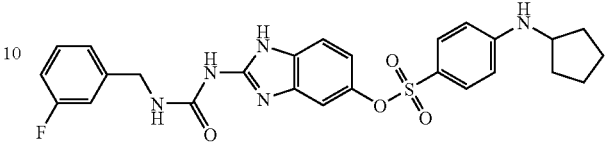

In a similar manner to example 33, title compound was obtained by reacting methyl-5-(4-cyclopentylaminophenyl-sulfonyloxy)benzimidazole-2-carbamate (example 19) with 3-fluorobenzylamine. (LC/MS analysis: retention time=3.96 min., mass spectrum: 524.33, [M+H]$^+$).

Example 42

4-Cyclopentylamino-benzenesulfonic acid 2-[3-(3-chloro-phenyl)-ureido]-1H-benzoimidazol-5-yl ester

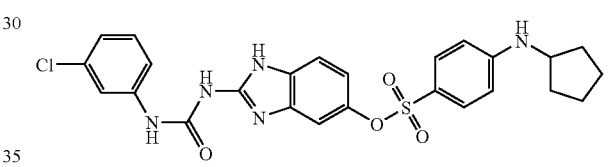

In a similar manner to example 33, title compound was obtained by reacting methyl-5-(4-cyclopentylaminophenyl-sulfonyloxy)benzimidazole-2-carbamate (example 19) with 3-chloroaniline. (LC/MS analysis: retention time=4.21 min., mass spectrum: 526.28, [M+H]$^+$).

Example 43

4-Cyclopentylamino-benzenesulfonic acid 2-(3-isobutyl-ureido)-1H-benzoimidazol-5-yl ester

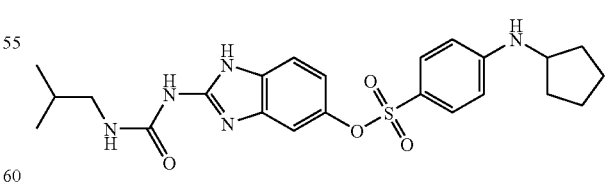

In a similar manner to example 33, title compound was obtained by reacting methyl-5-(4-cyclopentylaminophenyl-sulfonyloxy)benzimidazole-2-carbamate (example 19) with isobutylamine. (LC/MS analysis: retention time=3.88 min., mass spectrum: 472.38, [M+H]$^+$).

Example 44

4-Cyclopentylamino-benzenesulfonic acid 2-[3-(2-dimethylamino-ethyl)-ureido]-1H-benzoimidazol-5-yl ester

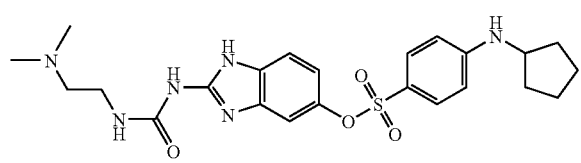

In a similar manner to example 33, title compound was obtained by reacting methyl-5-(4-cyclopentylaminophenyl-sulfonyloxy)benzimidazole-2-carbamate (example 19) with N,N-dimethylethylenediamine. (LC/MS analysis: retention time=3.22 min., mass spectrum: 487.38, [M+H]$^+$).

Example 45

4-Cyclopentylamino-benzenesulfonic acid 2-(3-ethyl-ureido)-1H-benzoimidazol-5-yl ester

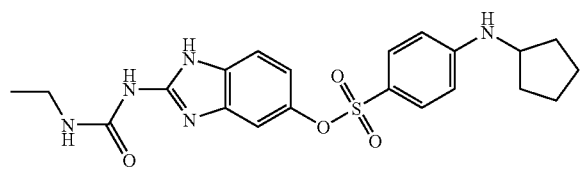

In a similar manner to example 33, title compound was obtained by reacting methyl-5-(4-cyclopentylaminophenyl-sulfonyloxy)benzimidazole-2-carbamate (example 19) with ethylamine (33% in water). (LC/MS analysis: retention time=3.64 min., mass spectrum: 444.35, [M+H]$^+$).

Example 46

{3-[5-(4-Cyclopentylamino-benzenesulfonyloxy)-1H-benzoimidazol-2-yl]-ureido}-acetic acid

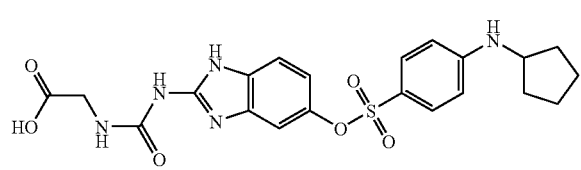

In a similar manner to example 33, title compound was obtained by reacting methyl-5-(4-cyclopentylaminophenyl-sulfonyloxy)benzimidazole-2-carbamate (example 19) with glycine. (LC/MS analysis: retention time=3.48 min., mass spectrum: 474.31, [M+H]$^+$).

Example 47

4-Imidazol-1-yl-benzenesulfonic acid 2-[3-(2-sulfo-ethyl)-ureido]-1H-benzoimidazol-5-yl ester

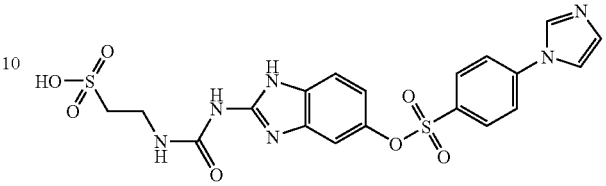

In a similar manner to example 30, title compound was obtained by reacting methyl-5-(4-[imidazolyl]-phenylsulfoxy)benzimidazole-2-carbamate (example 4) with 2-aminoethanesulfonic acid. (LC/MS analysis: retention time=2.40 min., mass spectrum: 507.21, [M+H]$^+$).

Example 48

4-Cyclopentylamino-benzenesulfonic acid 2-[3-(2-methoxy-ethyl)-ureido]-1H-benzoimidazol-5-yl ester

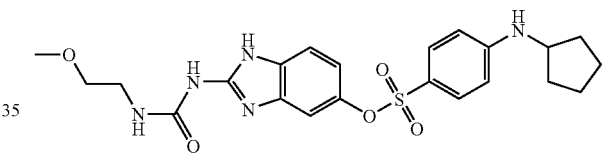

In a similar manner to example 33, title compound was obtained by reacting methyl-5-(4-cyclopentylaminophenyl-sulfonyloxy)benzimidazole-2-carbamate (example 19) with 2-methoxyethylamine. (LC/MS analysis: retention time=3.60 min., mass spectrum: 474.34, [M+H]$^+$).

Example 49

4-Cyclopentylamino-benzenesulfonic acid 2-[3-(4-dimethylamino-phenyl)-ureido]-1H-benzoimidazol-5-yl ester

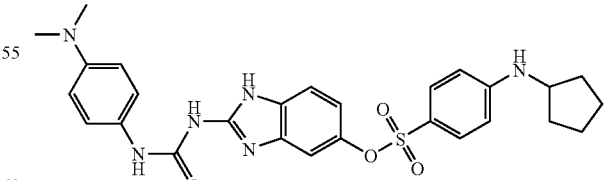

In a similar manner to example 33, title compound was obtained by reacting methyl-5-(4-cyclopentylaminophenyl-sulfonyloxy)benzimidazole-2-carbamate (example 19) with N,N-dimethyl-1,4-phenylenediamine. (LC/MS analysis: retention time=3.42 min., mass spectrum: 535.34, [M+H]$^+$).

Example 50

4-Cyclopentylamino-benzenesulfonic acid 2-(3-pyridin-2-ylmethyl-ureido)-1H-benzoimidazol-5-yl ester

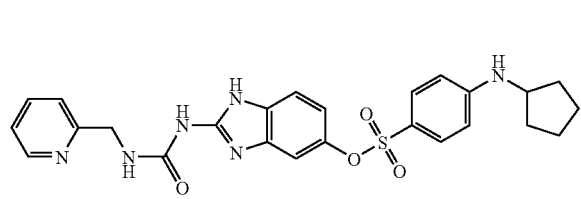

In a similar manner to example 33, title compound was obtained by reacting methyl-5-(4-cyclopentylaminophenyl-sulfonyloxy)benzimidazole-2-carbamate (example 19) with 2-aminomethylpyridine. (LC/MS analysis: retention time=3.30 min., mass spectrum: 507.33, [M+H]$^+$).

Example 51

4-Cyclopentylamino-benzenesulfonic acid 2-(3-cyclobutyl-ureido)-1H-benzoimidazol-5-yl ester

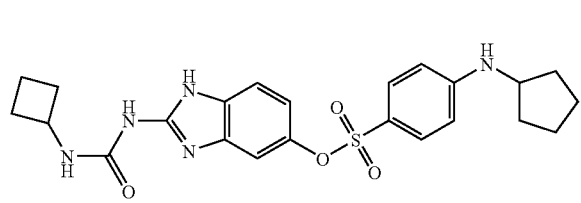

In a similar manner to example 33, title compound was obtained by reacting methyl-5-(4-cyclopentylaminophenyl-sulfonyloxy)benzimidazole-2-carbamate (example 19) with cyclobutylamine. (LC/MS analysis: retention time=3.84 min., mass spectrum: 470.36, [M+H]$^+$).

Example 52

4-Cyclopentylamino-benzenesulfonic acid 2-(3-pyridin-4-ylmethyl-ureido)-1H-benzoimidazol-5-yl ester

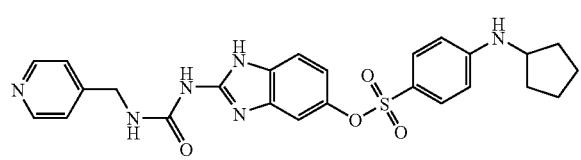

In a similar manner to example 33, title compound was obtained by reacting methyl-5-(4-cyclopentylaminophenyl-sulfonyloxy)benzimidazole-2-carbamate (example 19) with 4-(aminomethyl)pyridine. (LC/MS analysis: retention time=3.24 min., mass spectrum: 507.33, [M+H]$^+$).

Example 53

4-Cyclopentylamino-benzenesulfonic acid 2-(3-tert-butyl-ureido)-1H-benzoimidazol-5-yl ester

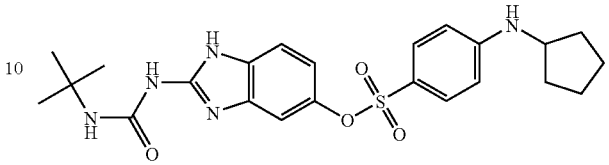

In a similar manner to example 33, title compound was obtained by reacting methyl-5-(4-cyclopentylaminophenyl-sulfonyloxy)benzimidazole-2-carbamate (example 19) with tert-butylamine. (LC/MS analysis: retention time=3.93 min., mass spectrum: 472.36, [M+H]$^+$).

Example 54

4-[(Tetrahydro-furan-2-ylmethyl)-amino]-benzenesulfonic acid 2-(3-methyl-ureido)-1H-benzoimidazol-5-yl ester

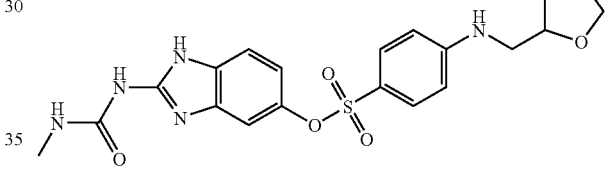

10 mg of methyl-5-(4-[1-tetrathydrofurylmethyl]aminophenyl-sulfonyloxy) benzimidazole-2-carbamate (example 18) were combined with 50 μl methylamine (2.0 M in tetrahydrofuran) and 5 μl 1,8-diazabicyclo[5.4.0]undec-7-ene in 2 ml N-methylpyrrolidone/tetrahydrofuran (1/1) in a 24 well Inox plate for high pressure reaction. The reaction mixture was put under a 10 Bars argon pressure and then heated to 80° C. for 4 hours, and then cooled at room temperature. Compounds were put in an assay tube and tetrahydrofuran was evaporated under reduce pressure and compound in N-methylpyrrolidone were directly purified by preparative LCMS in conditions described above. After purification, solution were dry-concentrated in a JOUAN RC1010 evaporator. (LC/MS analysis: retention time=2.91 min., mass spectrum: 446.07, [M+H]$^+$).

Example 55

4-Fluoro-benzenesulfonic acid 2-(cyclopropanecarbonyl-amino)-1H-benzoimidazol-5-yl ester

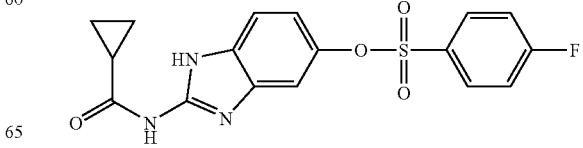

step 1: 10 g of 4-amino-3-nitrophenol in 180 ml of ethanol were hydrogenated under 40 bars pressure at 23° C. temperature with catalytic amound of palladium on carbon. Reaction was performed in an Inox flask for high pressure. After hydrogen uptake was complete, the catalyst was filtered off with suction, washed with methanol and the filtrate was concentred under reduced pressure yielding 8 g of crude 3,4-diaminophenol.

Step 2: 5.75 g of 3,4-diaminophenol were combined with 15.5 g of 1,3-bis(tert-butoxycarbonyl)-2-methyl-2-thiopseudourea in 150 ml methanol and 22 ml acetic acid in a round bottom flask. The reaction mixture was heated to reflux with stirring for 3 hours. Solvents were then evaporated under reduce pressure yielding 7.13 g crude (5-hydroxy-1H-benzoimidazol-2-yl)-carbamic acid tert-butyl ester.

Step 3: 5.98 g of (5-hydroxy-1H-benzoimidazol-2-yl)-carbamic acid tert-butyl ester were combined with 4.67 g of 4-fluorobenzenesulfonyl chloride and 6.75 ml of trietylamine in 100 ml acetone. The reaction mixture was stirred at room temperature for 1 hour. Solvents were evaporated under reduced pressure yielding 6.45 g crude 4-fluoro-benzenesulfonic acid 2-tert-butoxycarbonylamino-1H-benzoimidazol-5-yl ester.

Step 4: 6.45 g of 4-fluoro-benzenesulfonic acid 2-tert-butoxycarbonylamino-1H-benzoimidazol-5-yl ester were combined with 15 ml trifluoroacetic acid in 60 ml dichloromethane. The reaction mixture was stirred overnight at room temperature. Solvents were evaporated under reduced pressure. The residue was washed with ethyl ether and dried on glass frit yielding 6.58 g of 4-fluoro-benzenesulfonic acid 2-amino-1H-benzoimidazol-5-yl ester trifluoroacetic acid salt.

Step 5: 5.53 g of 4-fluoro-benzenesulfonic acid 2-amino-1H-benzoimidazol-5-yl ester trifluoroacetic acid salt were combined with 1.8 ml of cyclopropanecarbonylchloride and 5 ml triethylamine in 75 ml dichloromethane. Reaction mixture was stirred at room temperature for 1 hour. Solvents were evaporated under reduced pressure. The residue was then taken up in dichloromethane, washed with water and dried with magnesium sulfate. Dichloromethane was evaporated under reduced pressure and precipitate obtained was dried on glass frit yielding 4.88 g of 4-fluoro-benzenesulfonic acid 2-amino-3-cyclopropanecarbonyl-3H-benzoimidazol-5-yl ester.

Step 6: 3.27 g of 4-fluoro-benzenesulfonic acid 2-amino-3-cyclopropanecarbonyl-3H-benzoimidazol-5-yl ester; were combined with 106 mg of 4-(dimethylamino)pyridine in 80 ml acetonitrile. the reaction mixture was heated at 85° C. temperature for 72 hours with stirring. Yellow solution obtained was diluted in dichloromethane, washed with water and dried under magnesium sulfate. Solvents were evaporated under reduced pressure yielding 3.19 g of the title compound.

Example 56

Preparation of 4-[(1-Ethyl-pyrrolidin-2-ylmethyl)-amino]-benzenesulfonic acid 2-(cyclopropanecarbonyl-amino)-1H-benzoimidazol-5-yl ester

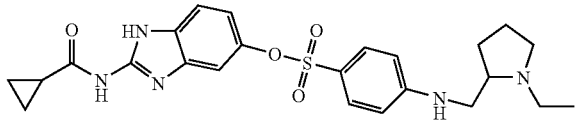

Title compound was obtained by reacting 12 mg of 4-fluoro-benzenesulfonic acid 2-(cyclopropanecarbonyl-amino)-1H-benzoimidazol-5-yl ester (example 55) with 21 mg of 2-(aminomethyl)-1-ethylpyrrolidine and 50 mg cesium carbonate in 600 µl dimethylsulfoxide. Reaction was performed in a 24 well Inox plate for high pressure. The reaction mixture was put under 10 bars argon pressure and then heated to 110° C. for 50 hours. Cesium carbonate was filtered off and compound in DMSO was directly purified by LCMS triggered purification yielding 10.7 mg title compound. (LC/MS analysis: retention time=2.58 min, mass spectrum: 483.99, [M+H]⁺.

Example 57

By using a method similar to that for the preparation of example 30, combining methyl-5-(4-[1-imidazolyl]-phenyl-sulfonyloxy)benzimidazole-2-carbamate precursor (example 4) with suitable amine were obtained the following compounds that were characterized by analytical LC/MS ([M+H]⁺ and retention time given in the following table.

| n° example | Precursor example | Amine | compound | [M + H]⁺ | Retention time (min) |
|---|---|---|---|---|---|
| 57-a | 4 | | 4-Imidazol-1-yl-benzenesulfonic acid 2-(3-phenyl-ureido)-1H-benzoimidazol-5-yl ester | 475.23 | 2.75 |
| 57-b | 4 | | 4-Imidazol-1-yl-benzenesulfonic acid 2-(3-cyclohexyl-ureido)-1H-benzoimidazol-5-yl ester | 481.28 | 2.76 |
| 57-c | 4 | | 4-Imidazol-1-yl-benzenesulfonic acid 2-(3-cyclopentyl-ureido)-1H-benzoimidazol-5-yl ester | 467.24 | 2.62 |

-continued

| n° example | Precursor example | Amine | compound | [M + H]⁺ | Retention time (min) |
|---|---|---|---|---|---|
| 57-d | 4 | 3-fluoroaniline | 4-Imidazol-1-yl-benzenesulfonic acid 2-[3-(3-fluoro-phenyl)-ureido]-1H-benzoimidazol-5-yl ester | 493.22 | 2.87 |
| 57-e | 4 | 2-aminoethanol (ethanolamine, H₂N-CH₂CH₂-OH) | 4-Imidazol-1-yl-benzenesulfonic acid 2-[3-(2-hydroxy-ethyl)-ureido]-1H-benzoimidazol-5-yl ester | 443.23 | 2.32 |
| 57-f | 4 | 4-fluoroaniline | 4-Imidazol-1-yl-benzenesulfonic acid 2-[3-(4-fluoro-phenyl)-ureido]-1H-benzoimidazol-5-yl ester | 493.22 | 2.80 |
| 57-g | 4 | 2-chlorobenzylamine | 4-Imidazol-1-yl-benzenesulfonic acid 2-[3-(2-chloro-benzyl)-ureido]-1H-benzoimidazol-5-yl ester | 523.25 | 3.08 |
| 57-h | 4 | 2-fluorobenzylamine | 4-Imidazol-1-yl-benzenesulfonic acid 2-[3-(2-fluoro-benzyl)-ureido]-1H-benzoimidazol-5-yl ester | 507.28 | 3.00 |
| 57-i | 4 | azetidine | 4-Imidazol-1-yl-benzenesulfonic acid 2-[(azetidine-1-carbonyl)-amino]-1H-benzoimidazol-5-yl ester | 439.31 | 2.55 |
| 57-j | 4 | 3-(aminomethyl)pyridine | 4-Imidazol-1-yl-benzenesulfonic acid 2-(3-pyridin-3-ylmethyl-ureido)-1H-benzoimidazol-5-yl ester | 490.31 | 2.39 |
| 57-k | 4 | 3-(4-methyl-piperazin-1-yl)propylamine | 4-Imidazol-1-yl-benzenesulfonic acid 2-{3-[3-(4-methyl-piperazin-1-yl)-propyl]-ureido}-1H-benzoimidazol-5-yl ester | 539.36 | 2.34 |

-continued

| n° example | Precursor example | Amine | compound | [M + H]+ | Retention time (min) |
|---|---|---|---|---|---|
| 57-l | 4 | NH2-CH2-C6H5 | 4-Imidazol-1-yl-benzenesulfonic acid 2-(3-benzyl-ureido)-1H-benzoimidazol-5-yl ester | 489.25 | 2.71 |

Example 58

By using a method similar to that for the preparation of example 33, combining methyl-5-(4-cyclopentylaminophenylsulfonyloxy)benzimidazole-2-carbamate (example 19) with suitable amine were obtained the following compounds that were characterized by analytical LC/MS ([M+H]+ and retention time given in the following table).

| n° example | Precursor example | Amine | compound | [M + H]+ | Retention time (min) |
|---|---|---|---|---|---|
| 58-a | 19 | aniline | 4-Cyclopentylamino-benzenesulfonic acid 2-(3-phenyl-ureido)-1H-benzoimidazol-5-yl ester | 492.28 | 3.77 |
| 58-b | 19 | cyclohexylamine | 4-Cyclopentylamino-benzenesulfonic acid 2-(3-cyclohexyl-ureido)-1H-benzoimidazol-5-yl ester; | 498.31 | 3.79 |
| 58-c | 19 | cyclopentylamine | 4-Cyclopentylamino-benzenesulfonic acid 2-(3-cyclopentyl-ureido)-1H-benzoimidazol-5-yl ester | 484.29 | 3.68 |
| 58-d | 19 | 3-fluoroaniline | 4-Cyclopentylamino-benzenesulfonic acid 2-[3-(3-fluoro-phenyl)-ureido]-1H-benzoimidazol-5-yl ester | 510.25 | 3.87 |
| 58-e | 19 | ethanolamine | 4-Cyclopentylamino-benzenesulfonic acid 2-[3-(2-hydroxy-ethyl)-ureido]-1H-benzoimidazol-5-yl ester | 460.28 | 3.17 |
| 58-f | 19 | 4-fluoroaniline | 4-Cyclopentylamino-benzenesulfonic acid 2-[3-(4-fluoro-phenyl)-ureido]-1H-benzoimidazol-5-yl ester | 510.24 | 3.80 |
| 58-g | 19 | 2-chlorobenzylamine | 4-Cyclopentylamino-benzenesulfonic acid 2-[3-(2-chloro-benzyl)-ureido]-1H-benzoimidazol-5-yl ester | 540.28 | 4.05 |

-continued

| n° example | Precursor example | Amine | compound | [M + H]+ | Retention time (min) |
|---|---|---|---|---|---|
| 58-h | 19 | 2-fluorobenzylamine | 4-Cyclopentylamino-benzenesulfonic acid 2-[3-(2-fluoro-benzyl)-ureido]-1H-benzoimidazol-5-yl ester | 524.33 | 3.97 |
| 58-i | 19 | azetidine | 4-Cyclopentylamino-benzenesulfonic acid 2-[(azetidine-1-carbonyl)-amino]-1H-benzoimidazol-5-yl ester | 456.37 | 3.60 |
| 58-j | 19 | 3-(aminomethyl)pyridine | 4-Cyclopentylamino-benzenesulfonic acid 2-(3-pyridin-3-ylmethyl-ureido)-1H-benzoimidazol-5-yl ester | 507.35 | 3.24 |
| 58-k | 19 | 3-(4-methylpiperazin-1-yl)propylamine | 4-Cyclopentylamino-benzenesulfonic acid 2-{3-[3-(4-methyl-piperazin-1-yl)-propyl]-ureido}-1H-benzoimidazol-5-yl ester | 556.39 | 3.09 |
| 58-l | 19 | benzylamine | 4-Cyclopentylamino-benzenesulfonic acid 2-(3-benzyl-ureido)-1H-benzoimidazol-5-yl ester | 506.31 | 3.70 |
| 58-m | 19 | 4-amino-butyric acid methyl ester | 4-{3-[5-(4-Cyclopentylamino-benzenesulfonyloxy)-1H-benzoimidazol-2-yl]-ureido}-butyric acid methyl ester | 516.31 | 3.74 |
| 58-n | 19 | 4-amino-butyric acid ethyl ester | 4-{3-[5-(4-Cyclopentylamino-benzenesulfonyloxy)-1H-benzoimidazol-2-yl]-ureido}-butyric acid ethyl ester | 530.30 | 3.84 |
| 58-o | 19 | glycine methyl ester | 4-{3-[5-(4-Cyclopentylamino-benzenesulfonyloxy)-1H-benzoimidazol-2-yl]-ureido}-acetic acid methyl ester | 488.26 | 3.65 |

-continued

| n° example | Precursor example | Amine | compound | [M + H]+ | Retention time (min) |
|---|---|---|---|---|---|
| 58-p | 19 | H2N-propyl-imidazole | 4-Cyclopentylamino-benzenesulfonic acid 2-[3-(3-imidazol-1-yl-propyl)-ureido]-1H-benzoimidazol-5-yl ester | 524.30 | 3.29 |
| 58-q | 19 | L-proline | 1-[5-(4-Cyclopentylamino-benzenesulfonyloxy)-1H-benzoimidazol-2S-ylcarbamoyl]-pyrrolidine-2-carboxylic acid | 514.27 | 3.56 |
| 58-r | 19 | L-proline methyl ester | 1-[5-(4-Cyclopentylamino-benzenesulfonyloxy)-1H-benzoimidazol-2S-yl-carbamoyl]-pyrrolidine-2-carboxylic acid methyl ester | 528.27 | 3.79 |
| 58-s | 19 | glycinamide | 4-Cyclopentylamino-benzenesulfonic acid 2-(3-carbamoylmethyl-ureido)-1H-benzoimidazol-5-yl ester | 473.28 | 3.38 |
| 58-t | 19 | ethyl isonipecotate | 1-[5-(4-Cyclopentylamino-benzenesulfonyloxy)-1H-benzoimidazol-2-yl-carbamoyl]-piperidine-4-carboxylic acid ethyl ester | 556.29 | 3.93 |
| 58-u | 19 | 4-(aminomethyl)piperidine | 4-Cyclopentylamino-benzenesulfonic acid 2-(3-piperidin-4-ylmethyl-ureido)-1H-benzoimidazol-5-yl ester | 513.33 | 3.25 |
| 58-v | 19 | 2-(morpholin-4-yl)ethylamine | 4-Cyclopentylamino-benzenesulfonic acid 2-[3-(2-morpholin-4-yl-ethyl)-ureido]-1H-benzoimidazol-5-yl ester | 529.31 | 3.27 |
| 58-w | 19 | 1,2-diamino-2-methylpropane | 4-Cyclopentylamino-benzenesulfonic acid 2-[3-(2-amino-2-methyl-propyl)-ureido]-1H-benzoimidazol-5-yl ester | 487.32 | 3.25 |

-continued

| n° example | Precursor example | Amine | compound | [M + H]+ | Retention time (min) |
|---|---|---|---|---|---|
| 58-x | 19 | 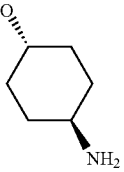 | 4-Cyclopentylamino-benzenesulfonic acid 2-[3-(4trans-hydroxy-cyclohexyl)-ureido]-1H-benzoimidazol-5-yl ester | 514.30 | 3.54 |
| 58-y | 19 | 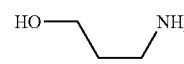 | 4-Cyclopentylamino-benzenesulfonic acid 2-[3-(3-hydroxy-propyl)-ureido]-1H-benzoimidazol-5-yl ester | 474.28 | 3.46 |
| 58-z | 19 | 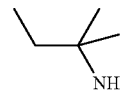 | 4-Cyclopentylamino-benzenesulfonic acid 2-[3-(1,1-dimethyl-propyl)-ureido]-1H-benzoimidazol-5-yl ester | 486.33 | 4.08 |
| 58-aa | 19 | 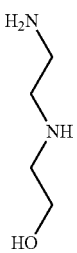 | 4-Cyclopentylamino-benzenesulfonic acid 2-{3-[2-(2-hydroxy-ethylamino)-ethyl]-ureido}-1H-benzoimidazol-5-yl ester | 503.30 | 3.19 |
| 58-ab | 19 |  | 4-Cyclopentylamino-benzenesulfonic acid 2-[3-(4-hydroxy-butyl)-ureido]-1H-benzoimidazol-5-yl ester | 488.29 | 3.49 |
| 58-ac | 19 | 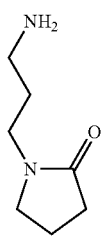 | 4-Cyclopentylamino-benzenesulfonic acid 2-{3-[3-(2-oxo-pyrrolidin-1-yl)-propyl]-ureido}-1H-benzoimidazol-5-yl ester | 541.29 | 3.54 |
| 58-ad | 19 | 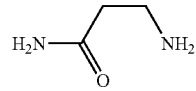 | 4-Cyclopentylamino-benzenesulfonic acid 2-[3-(2-carbamoyl-ethyl)-ureido]-1H-benzoimidazol-5-yl ester | 487.30 | 3.40 |
| 58-ae | 19 | 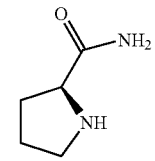 | 4-Cyclopentylamino-benzenesulfonic acid 2-[(2S-carbamoyl-pyrrolidine-1-carbonyl)-amino]-1H-benzoimidazol-5-yl ester | 513.30 | 3.42 |

| n° example | Precursor example | Amine | compound | [M + H]+ | Retention time (min) |
|---|---|---|---|---|---|
| 58-af | 19 |  | 4-Cyclopentylamino-benzenesulfonic acid 2-{3-[2-(2-hydroxy-ethoxy)-ethyl]-ureido}-1H-benzoimidazol-5-yl ester | 504.30 | 3.46 |
| 58-ag | 19 |  | 4-Cyclopentylamino-benzenesulfonic acid 2-[3-(3-pyrrolidin-1-yl-propyl)-ureido]-1H-benzoimidazol-5-yl ester | 527.35 | 3.33 |
| 58-ah | 19 | 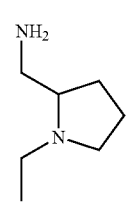 | 4-Cyclopentylamino-benzenesulfonic acid 2-[3-(1-ethyl-pyrrolidin-2-ylmethyl)-ureido]-1H-benzoimidazol-5-yl ester | 527.35 | 3.30 |
| 58-ai | 19 | 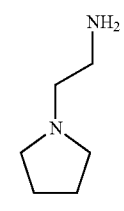 | 4-Cyclopentylamino-benzenesulfonic acid 2-[3-(2-pyrrolidin-1-yl-ethyl)-ureido]-1H-benzoimidazol-5-yl ester | 513.34 | 3.29 |
| 58-aj | 19 | 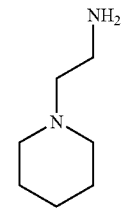 | 4-Cyclopentylamino-benzenesulfonic acid 2-[3-(2-piperidin-1-yl-ethyl)-ureido]-1H-benzoimidazol-5-yl ester | 527.35 | 3.33 |
| 58-ak | 19 | 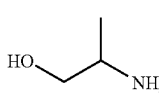 | 4-Cyclopentylamino-benzenesulfonic acid 2-[3-(2-hydroxy-1-methyl-ethyl)-ureido]-1H-benzoimidazol-5-yl ester | 474.30 | 3.51 |
| 58-al | 19 | 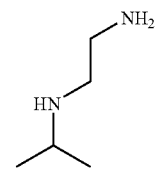 | 4-Cyclopentylamino-benzenesulfonic acid 2-[3-(2-isopropylamino-ethyl)-ureido]-1H-benzoimidazol-5-yl ester | 501.34 | 3.31 |

-continued

| n° example | Precursor example | Amine | compound | [M + H]⁺ | Retention time (min) |
|---|---|---|---|---|---|
| 58-am | 19 | 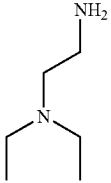 | 4-Cyclopentylamino-benzenesulfonic acid 2-[3-(2-diethylamino-ethyl)-ureido]-1H-benzoimidazol-5-yl ester | 515.34 | 3.31 |
| 58-an | 19 | 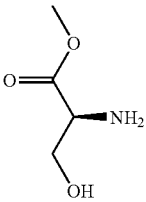 | 2-{3-[5-(4-Cyclopentylamino-benzenesulfonyloxy)-1H-benzoimidazol-2-yl]-ureido}-3S-hydroxy-propionic acid methyl ester | 518.27 | 3.55 |

Example 59

By using a method similar to that for the preparation of example 54, combining methyl-5-(4-[1-tetrahydrofurylmethyl]aminophenyl-sulfonyloxy)benzimidazole-2-carbamate (example 18) with suitable amine were obtained the following compounds that were characterized by analytical LC/MS ([M+H]⁺ and retention time given in the following table).

| n° example | Precursor example | Amine | compound | [M + H]⁺ | Retention time (min) |
|---|---|---|---|---|---|
| 59-a | 18 | 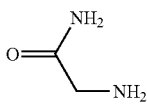 | 4-[(Tetrahydro-furan-2-ylmethyl)-amino]-benzenesulfonic acid 2-(3-carbamoylmethyl-ureido)-1H-benzoimidazol-5-yl ester | 489.15 | 2.78 |
| 59-b | 18 | 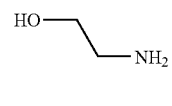 | 4-[(Tetrahydro-furan-2-ylmethyl)-amino]-benzenesulfonic acid 2-[3-(2-hydroxy-ethyl)-ureido]-1H-benzoimidazol-5-yl ester | 476.15 | 2.91 |
| 59-c | 18 | 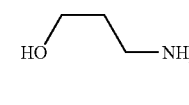 | 4-[(Tetrahydro-furan-2-ylmethyl)-amino]-benzenesulfonic acid 2-[3-(3-hydroxy-propyl)-ureido]-1H-benzoimidazol-5-yl ester | 490.18 | 2.89 |
| 59-d | 18 | 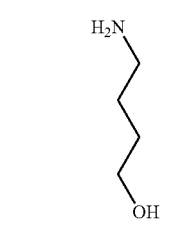 | 4-[(Tetrahydro-furan-2-ylmethyl)-amino]-benzenesulfonic acid 2-[3-(4-hydroxy-butyl)-ureido]-1H-benzoimidazol-5-yl ester | 504.19 | 3.44 |
| 59-e | 18 | 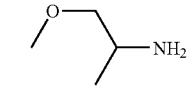 | 4-[(Tetrahydro-furan-2-ylmethyl)-amino]-benzenesulfonic acid 2-[3-(2-methoxy-1-methyl-ethyl)-ureido]-1H-benzoimidazol-5-yl ester | 504.19 | 3.11 |

-continued

| n° example | Precursor example | Amine | compound | [M + H]+ | Retention time (min) |
|---|---|---|---|---|---|
| 59-f | 18 | 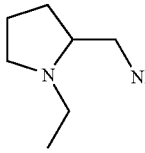 | 4-[(Tetrahydro-furan-2-ylmethyl)-amino]-benzenesulfonic acid 2-[3-(1-ethyl-pyrrolidin-2-ylmethyl)-ureido]-1H-benzoimidazol-5-yl ester | 543.24 | 2.89 |
| 59-g | 18 | 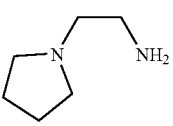 | 4-[(Tetrahydro-furan-2-ylmethyl)-amino]-benzenesulfonic acid 2-[3-(2-pyrrolidin-1-yl-ethyl)-ureido]-1H-benzoimidazol-5-yl ester | 529.22 | 2.66 |
| 59-h | 18 |  | 4-[(Tetrahydro-furan-2-ylmethyl)-amino]-benzenesulfonic acid 2-[3-(3-pyrrolidin-1-yl-propyl)-ureido]-1H-benzoimidazol-5-yl ester | 543.25 | 2.73 |
| 59-i | 18 | 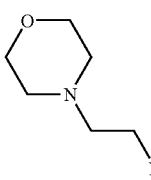 | 4-[(Tetrahydro-furan-2-ylmethyl)-amino]-benzenesulfonic acid 2-[3-(2-morpholin-4-yl-ethyl)-ureido]-1H-benzoimidazol-5-yl ester | 545.23 | 2.61 |
| 59-j | 18 |  | 4-[(Tetrahydro-furan-2-ylmethyl)-amino]-benzenesulfonic acid 2-(3-ethyl-ureido)-1H-benzoimidazol-5-yl ester | 460.17 | 3.08 |
| 59-k | 18 | 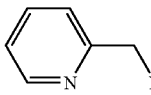 | 4-[(Tetrahydro-furan-2-ylmethyl)-amino]-benzenesulfonic acid 2-(3-pyridin-2-ylmethyl-ureido)-1H-benzoimidazol-5-yl ester | 523.07 | 2.70 |
| 59-l | 18 | 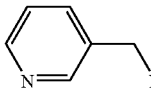 | 4-[(Tetrahydro-furan-2-ylmethyl)-amino]-benzenesulfonic acid 2-(3-pyridin-3-ylmethyl-ureido)-1H-benzoimidazol-5-yl ester | 523.19 | 2.64 |
| 59-m | 18 | 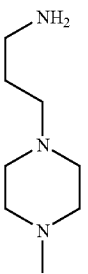 | 4-[(Tetrahydro-furan-2-ylmethyl)-amino]-benzenesulfonic acid 2-{3-[3-(4-methyl-piperazin-1-yl)-propyl]-ureido}-1H-benzoimidazol-5-yl ester | 572.27 | 2.60 |
| 59-n | 18 | 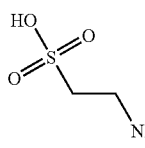 | 4-[(Tetrahydro-furan-2-ylmethyl)-amino]-benzenesulfonic acid 2-[3-(2-sulfo-ethyl)-ureido]-1H-benzoimidazol-5-yl ester | 540.13 | 2.81 |

-continued

| n° example | Precursor example | Amine | compound | [M + H]⁺ | Retention time (min) |
|---|---|---|---|---|---|
| 59-o | 18 | cyclobutyl-CH2-NH2 | 4-[(Tetrahydro-furan-2-ylmethyl)-amino]-benzenesulfonic acid 2-(3-cyclobutyl-ureido)-1H-benzoimidazol-5-yl ester | 486.19 | 3.28 |
| 59-p | 18 | 1-(3-aminopropyl)-2-pyrrolidinone | 4-[(Tetrahydro-furan-2-ylmethyl)-amino]-benzenesulfonic acid 2-{3-[3-(2-oxo-pyrrolidin-1-yl)-propyl]-ureido}-1H-benzoimidazol-5-yl ester | 557.23 | 2.94 |
| 59-q | 18 | H2N-CH2CH2-NH-CH2CH2-OH | 4-[(Tetrahydro-furan-2-ylmethyl)-amino]-benzenesulfonic acid 2-{3-[2-(2-hydroxy-ethylamino)-ethyl]-ureido}-1H-benzoimidazol-5-yl ester | 519.21 | 2.64 |
| 59-r | 18 | 1-(2-aminoethyl)piperidine | 4-[(Tetrahydro-furan-2-ylmethyl)-amino]-benzenesulfonic acid 2-[3-(2-piperidin-1-yl-ethyl)-ureido]-1H-benzoimidazol-5-yl ester | 543.24 | 2.74 |

Example 60

By using a method similar to that for the preparation of example 56, combining 4-fluoro-benzenesulfonic acid 2-(cyclopropanecarbonyl-amino)-1H-benzoimidazol-5-yl ester (example 55) with suitable amine were obtained the following compounds that were characterized by analytical LC/MS ([M+H]⁺ and retention time given in the following table).

| n° example | Precursor example | Amine | compound | [M + H]⁺ | Retention time (min) |
|---|---|---|---|---|---|
| 60-a | 55 | benzylamine | 4-Benzylamino-benzenesulfonic acid 2-(cyclopropanecarbonyl-amino)-1H-benzoimidazol-5-yl ester | 436.3 | 3.68 |
| 60-b | 55 | H2N-CH3 | 4-Methylamino-benzenesulfonic acid 2-(cyclopropanecarbonyl-amino)-1H-benzoimidazol-5-yl ester | 387.3 | 3.18 |
| 60-c | 55 | H2N-CH2CH2-OH | 4-(2-Hydroxy-ethylamino)-benzenesulfonic acid 2-(cyclopropanecarbonyl-amino)-1H-benzoimidazol-5-yl ester | 417.3 | 2.98 |

-continued

| n° example | Precursor example | Amine | compound | [M + H]+ | Retention time (min) |
|---|---|---|---|---|---|
| 60-d | 55 | H₂N~~~OH | 4-(3-Hydroxy-propylamino)-benzenesulfonic acid 2-(cyclopropanecarbonyl-amino)-1H-benzoimidazol-5-yl ester | 431.35 | 3.04 |
| 60-e | 55 | NH₂(CH₂)₄OH | 4-(4-Hydroxy-butylamino)-benzenesulfonic acid 2-(cyclopropanecarbonyl-amino)-1H-benzoimidazol-5-yl ester | 445.35 | 3.10 |
| 60-f | 55 | H₂N-CH(CH₃)-CH₂-O-CH₃ | 4-(2-Methoxy-1-methyl-ethylamino)-benzenesulfonic acid 2-(cyclopropanecarbonyl-amino)-1H-benzoimidazol-5-yl ester | 445.35 | 3.41 |
| 60-g | 55 | NH₂-CH₂CH₂-pyrrolidine | 4-(2-Pyrrolidin-1-yl-ethylamino)-benzenesulfonic acid 2-(cyclopropanecarbonyl-amino)-1H-benzoimidazol-5-yl ester | 470.37 | 2.80 |
| 60-h | 55 | H₂N-CH(Et)-CH₂OH | 4-(1-Hydroxymethyl-propylamino)-benzenesulfonic acid 2-(cyclopropanecarbonyl-amino)-1H-benzoimidazol-5-yl ester | 445.34 | 3.21 |
| 60-i | 55 | H₂N-CH(CH₃)-CH₂OH | 4-(2-Hydroxy-1-methyl-ethylamino)-benzenesulfonic acid 2-(cyclopropanecarbonyl-amino)-1H-benzoimidazol-5-yl ester | 431.34 | 3.08 |
| 60-j | 55 | NH₂-CH₂CH₂-piperidine | 4-(2-Piperidin-1-yl-ethylamino)-benzenesulfonic acid 2-(cyclopropanecarbonyl-amino)-1H-benzoimidazol-5-yl ester | 484.38 | 2.85 |
| 60-k | 55 | pyrrolidine-CH₂CH₂CH₂-NH₂ | 4-(3-Pyrrolidin-1-yl-propylamino)-benzenesulfonic acid 2-(cyclopropanecarbonyl-amino)-1H-benzoimidazol-5-yl ester | 484.37 | 2.85 |
| 60-l | 55 | H₂N-CH₂-C(CH₃)₂-CH₂OH | 4-(3-Hydroxy-2,2-dimethyl-propylamino)-benzenesulfonic acid 2-(cyclopropanecarbonyl-amino)-1H-benzoimidazol-5-yl ester | 459.34 | 3.30 |

| n° example | Precursor example | Amine | compound | [M + H]⁺ | Retention time (min) |
|---|---|---|---|---|---|
| 60-m | 55 | pyridin-3-yl-methylamine (3-aminomethylpyridine) | 4-[(Pyridin-3-yl-methyl)-amino]-benzenesulfonic acid 2-(cyclopropanecarbonyl-amino)-1H-benzoimidazol-5-yl ester | 464.30 | 2.77 |
| 60-n | 55 | 3-(4-methylpiperazin-1-yl)propan-1-amine | 4-[3-(4-Methyl-piperazin-1-yl)-propylamino]-benzenesulfonic acid 2-(cyclopropanecarbonyl-amino)-1H-benzoimidazol-5-yl ester | 513.38 | 2.66 |
| 60-o | 55 | 2-methoxybenzylamine | 4-(2-Methoxy-benzylamino)-benzenesulfonic acid 2-(cyclopropanecarbonyl-amino)-1H-benzoimidazol-5-yl ester | 493.32 | 3.74 |
| 60-p | 55 | 4-hydroxycyclohexylamine | 4-(4-Hydroxy-cyclohexylamino)-benzenesulfonic acid 2-(cyclopropanecarbonyl-amino)-1H-benzoimidazol-5-yl ester | 471.36 | 3.11 |
| 60-q | 55 | N,N-diethylethylenediamine | 4-(2-Diethylamino-ethylamino)-benzenesulfonic acid 2-(cyclopropanecarbonyl-amino)-1H-benzoimidazol-5-yl ester | 472.37 | 2.82 |
| 60-r | 55 | (2S)-2-amino-1-butanol (chiral) | 4-(1S-Hydroxymethyl-propylamino)-benzenesulfonic acid 2-(cyclopropanecarbonyl-amino)-1H-benzoimidazol-5-yl ester | 445.32 | 3.19 |
| 60-s | 55 | N-ethylethylenediamine | 4-(2-Ethylamino-ethylamino)-benzenesulfonic acid 2-(cyclopropanecarbonyl-amino)-1H-benzoimidazol-5-yl ester | 444.34 | 2.75 |

-continued

| n° example | Precursor example | Amine | compound | [M + H]+ | Retention time (min) |
|---|---|---|---|---|---|
| 60-t | 55 | (structure: 2-diisopropylaminoethylamine) | 4-(2-Diisopropylamino-ethylamino)-benzenesulfonic acid 2-(cyclopropanecarbonyl-amino)-1H-benzoimidazol-5-yl ester | 500.38 | 2.91 |
| 60-u | 55 | (structure: 2-morpholin-4-yl-ethylamine) | 4-(2-Morpholin-4-yl-ethylamino)-benzenesulfonic acid 2-(cyclopropanecarbonyl-amino)-1H-benzoimidazol-5-yl ester | 486.34 | 2.76 |
| 60-v | 55 | (structure: 3-aminoquinuclidine) | 4-(1-Aza-bicyclo[2.2.2]-oct-3-ylamino)-benzenesulfonic acid 2-(cyclopropane-carbonyl-amino)-1H-benzoimidazol-5-yl ester | 482.35 | 2.82 |
| 60-w | 55 | (structure: N-phenylethylenediamine) | 4-(2-Phenylamino-ethylamino)-benzenesulfonic acid 2-(cyclopropanecarbonyl-amino)-1H-benzoimidazol-5-yl ester | 492.34 | 3.34 |
| 60-x | 55 | (structure: 1-benzyl-3-aminopyrrolidine) | 4-(1-Benzyl-pyrrolidin-3-ylamino)-benzenesulonic acid 2-(cyclopropane-carbonyl-amino)-1H-benzoimidazol-5-yl ester | 532.35 | 3.05 |
| 60-y | 55 | (structure: D-prolinamide) | 4-(2R-Carbamoyl-pyrrolidin-1-yl)-benzenesulfonic acid 2-(cyclopropanecarbonyl-amino)-1H-benzoimidazol-5-yl ester | 470.32 | 3.00 |
| 60-z | 55 | (structure: 3-dimethylaminopropylamine) | 4-(3-Dimethylamino-propylamino)-benzenesulfonic acid 2-(cyclopropanecarbonyl-amino)-1H-benzoimidazol-5-yl ester; | 458.36 | 2.79 |

-continued

| n° example | Precursor example | Amine | compound | [M + H]+ | Retention time (min) |
|---|---|---|---|---|---|
| 60-aa | 55 | 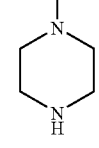 | 4-(2-Piperazin-1-yl-ethylamino)-benzene-sulfonic acid 2-(cyclopropanecarbonyl-amino)-1H-benzoimidazol-5-yl ester | 485.37 | 2.63 |
| 60-ab | 55 | 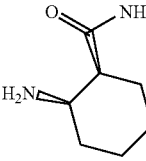 | 4-(2-Carbamoyl-cyclohexylamino)-benzenesulfonic acid 2-(cyclopropanecarbonyl-amino)-1H-benzoimidazol-5-yl ester | 498.34 | 3.24 |
| 60-ac | 55 | 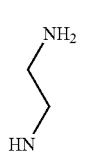 | 4-(2-Acetylamino-ethylamino)-benzenesulfonic acid 2-(cyclopropanecarbonyl-amino)-1H-benzoimidazol-5-yl ester | 458.32 | 2.95 |
| 60-ad | 55 | 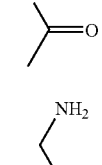 | 4-[2-(2-Amino-ethylamino)-ethylamino]-benzenesulfonic acid 2-(cyclopropanecarbonyl-amino)-1H-benzoimidazol-5-yl ester | 459.34 | 2.60 |
| 60-ae | 55 | 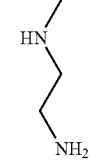 | 4-[3-(2-Oxo-pyrrolidin-1-yl)-propylamino]-benzenesulfonic acid 2-(cyclopropanecarbonyl-amino)-1H-benzoimidazol-5-yl ester | 498.34 | 3.14 |
| 60-af | 55 | 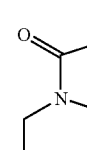 | 4-[2-(1H-Imidazol-4-yl)-ethylamino]-benzenesulfonic acid 2-(cyclopropanecarbonyl-amino)-1H-benzoimidazol-5-yl ester | 467.31 | 2.79 |
| 60-ag | 55 | 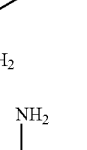 | 4-[(Pyridin-2-ylmethyl)-amino]-benzenesulfonic acid 2-(cyclopropane-carbonyl-amino)-1H-benzoimidazol-5-yl ester | 464.31 | 2.80 |

-continued

| n° example | Precursor example | Amine | compound | [M + H]+ | Retention time (min) |
|---|---|---|---|---|---|
| 60-ah | 55 | H₂N-cyclobutyl | 4-Cyclobutylamino-benzenesulfonic acid 2-(cyclopropanecarbonyl-amino)-1H-benzoimidazol-5-yl ester | 427.31 | 3.63 |
| 60-ai | 55 | H₂N-CH₂CH₂-O-CH₂CH₂-OH | 4-[2-(2-Hydroxy-ethoxy)-ethylamino]-benzenesulfonic acid 2-(cyclopropanecarbonyl-amino)-1H-benzoimidazol-5-yl ester | 461.34 | 3.01 |
| 60-aj | 55 | H₂N-CH₂-CH(OH)-CH₂OH | 4-(2,3-Dihydroxy-propylamino)-benzenesulfonic acid 2-(cyclopropanecarbonyl-amino)-1H-benzoimidazol-5-yl ester | 447.31 | 2.84 |
| 60-ak | 55 | 2-(imidazol-1-yl)ethylamine | 4-(2-Imidazol-1-yl-ethylamino)-benzenesulfonic acid 2-(cyclopropanecarbonyl-amino)-1H-benzoimidazol-5-yl ester | 467.32 | 2.78 |
| 60-al | 55 | HO-CH₂CH₂-NH-CH₂CH₂-NH₂ | 4-[2-(2-Hydroxy-ethylamino)-ethylamino]-benzenesulfonic acid 2-(cyclopropanecarbonyl-amino)-1H-benzoimidazol-5-yl ester | 460.34 | 2.70 |
| 60-am | 55 | H₂N-CH₂CH₂-O-CH₃ | 4-(2-Methoxy-ethylamino)-benzenesulfonic acid 2-(cyclopropanecarbonyl-amino)-1H-benzoimidazol-5-yl ester | 431.32 | 3.27 |
| 60-an | 55 | H₂N-CH(CH₃)-CH₂-N(CH₃)₂ | 4-(2-Dimethylamino-1-methyl-ethylamino)-benzenesulfonic acid 2-(cyclopropanecarbonyl-amino)-1H-benzoimidazol-5-yl ester | 458.36 | 2.79 |
| 60-ao | 55 | 3-aminopyrrolidine | 4-(Pyrrolidin-3-ylamino)-benzenesulfonic acid 2-(cyclopropanecarbonyl-amino)-1H-benzoimidazol-5-yl ester | 442.35 | 2.75 |
| 60-ap | 55 | tryptamine (H₂N-CH₂CH₂-indol-3-yl) | 4-[2-(1H-Indol-3-yl)-ethylamino]-benzenesulfonic acid 2-(cyclopropanecarbonyl-amino)-1H-benzoimidazol-5-yl ester | 516.32 | 3.75 |

| n° example | Precursor example | Amine | compound | [M + H]+ | Retention time (min) |
|---|---|---|---|---|---|
| 60-aq | 55 | H₂N—⟋⟍N⟋⟍ | 4-(2-Dimethylamino-ethylamino)-benzenesulfonic acid 2-(cyclopropanecarbonyl-amino)-1H-benzoimidazol-5-yl ester | 444.35 | 2.74 |
| 60-ar | 55 | H₂N—CH₂CH₂—O—C₆H₅ | 4-(2-Phenoxy-ethylamino)-benzenesulfonic acid 2-(cyclopropanecarbonyl-amino)-1H-benzoimidazol-5-yl ester | 493.32 | 3.78 |
| 60-as | 55 | H₂N-bicycloheptyl | 4-(Bicyclo[2.2.1]hept-2R-ylamino)-benzenesulfonic acid 2-(cyclopropane-carbonyl-amino)-1H-benzoimidazol-5-yl ester | 467.35 | 3.95 |
| 60-at | 55 | H₂N—CH₂CH₂—NH—CH₃ | 4-(2-Methylamino-ethylamino)-benzenesulfonic acid 2-(cyclopropanecarbonyl-amino)-1H-benzoimidazol-5-yl ester | 430.35 | 2.74 |
| 60-au | 55 | NH₂—CH₂CH₂—NH—CH₂CH₂CH₃ | 4-(2-Propylamino-ethylamino)-benzenesulfonic acid 2-(cyclopropanecarbonyl-amino)-1H-benzoimidazol-5-yl ester | 458.36 | 2.84 |
| 60-av | 55 | CH₃CH(NH₂)CH₂—O—C₆H₅ | 4-(1-Methyl-2-phenoxy-ethylamino)-benzenesulfonic acid 2-(cyclopropanecarbonyl-amino)-1H-benzoimidazol-5-yl ester | 507.33 | 3.89 |
| 60-aw | 55 | H₂N—CH₂-(piperidin-4-yl) | 4-[(Piperidin-4-ylmethyl)-amino]-benzenesulfonic acid 2-(cyclopropane-carbonyl-amino)-1H-benzoimidazol-5-yl ester | 470.36 | 2.84 |
| 60-ax | 55 | 4-MeO-C₆H₄-CH₂-NH₂ | 4-(4-Methoxy-benzylamino)-benzenesulfonic acid 2-(cyclopropanecarbonyl-amino)-1H-benzoimidazol-5-yl ester | 493.31 | 3.68 |

-continued

| n° example | Precursor example | Amine | compound | [M + H]+ | Retention time (min) |
|---|---|---|---|---|---|
| 60-ay | 55 | 1H-benzimidazol-5-amine | 4-(1H-Benzoimidazol-5-ylamino)-benzenesulfonic acid 2-(cyclopropanecarbonyl-amino)-1H-benzoimidazol-5-yl ester | 489.29 | 2.80 |
| 60-az | 55 | 3-methoxypropylamine | 4-(3-Methoxy-propylamino)-benzenesulfonic acid 2-(cyclopropanecarbonyl-amino)-1H-benzoimidazol-5-yl ester | 445.10 | 3.17 |
| 60-ba | 55 | 2,2-dimethoxyethylamine | 4-(2,2-Dimethoxy-ethylamino)-benzenesulfonic acid 2-(cyclopropanecarbonyl-amino)-1H-benzoimidazol-5-yl ester | 461.11 | 3.20 |
| 60-bb | 55 | N,N-dimethyl-p-phenylenediamine | 4-(4-Dimethylamino-phenylamino)-benzenesulfonic acid 2-(cyclopropanecarbonyl-amino)-1H-benzoimidazol-5-yl ester | 492.12 | 2.87 |
| 60-bc | 55 | 3-methoxybenzylamine | 4-(3-Methoxy-benzylamino)-benzenesulfonic acid 2-(cyclopropanecarbonyl-amino)-1H-benzoimidazol-5-yl ester | 493.10 | 3.69 |
| 60-bd | 55 | 4-pyrrolidin-1-yl-butylamine | 4-(4-Pyrrolidin-1-yl-butylamino)-benzenesulfonic acid 2-(cyclopropanecarbonyl-amino)-1H-benzoimidazol-5-yl ester | 498.16 | 2.64 |
| 60-be | 55 | 2,3-dimethoxybenzylamine | 4-(2,3-Dimethoxy-benzylamino)-benzenesulfonic acid 2-(cyclopropanecarbonyl-amino)-1H-benzoimidazol-5-yl ester | 523.11 | 3.80 |
| 60-bf | 55 | propargylamine | 4-Prop-2-ynylamino-benzenesulfonic acid 2-(cyclopropanecarbonyl-amino)-1H-benzoimidazol-5-yl ester | 411.07 | 3.15 |

-continued

| n° example | Precursor example | Amine | compound | [M + H]⁺ | Retention time (min) |
|---|---|---|---|---|---|
| 60-bg | 55 | | 4-[4-(2-Hydroxy-ethyl)-piperazin-1-yl]-benzenesulfonic acid 2-(cyclopropanecarbonyl-amino)-1H-benzoimidazol-5-yl ester | 464.09 | 2.48 |
| 60-bh | 55 | | 4-[(Pyridin-4-ylmethyl)-amino]-benzenesulfonic acid 2-(cyclopropane-carbonyl-amino)-1H-benzoimidazol-5-yl ester | 464.09 | 2.48 |
| 60-bi | 55 | | 4-[2-(Ethyl-m-tolyl-amino)-ethylamino]-benzenesulfonic acid 2-(cyclopropanecarbonyl-amino)-1H-benzoimidazol-5-yl ester | 534.18 | 3.10 |
| 60-bj | 55 | | 4-(2-Hydroxy-cyclohexylamino)-benzenesulfonic acid 2-(cyclopropanecarbonyl-amino)-1H-benzoimidazol-5-yl ester | 471.13 | 3.25 |
| 60-bk | 55 | | 4-(3-Dimethylamino-2,2-dimethyl-propylamino)-benzenesulfonic acid 2-(cyclopropanecarbonyl-amino)-1H-benzoimidazol-5-yl ester | 486.18 | 2.64 |
| 60-bl | 55 | | 4-[3-(2-Hydroxy-ethylamino)-propylamino]-benzenesulfonic acid 2-(cyclopropanecarbonyl-amino)-1H-benzoimidazol-5-yl ester | 474.14 | 2.45 |
| 60-bm | 55 | | 4-[(Tetrahydro-furan-2RS-ylmethyl)-amino]-benzenesulfonic acid 2-(cyclopropanecarbonyl-amino)-1H-benzoimidazol-5-yl ester; | 456.80 | 3.15 |

-continued

| n° example | Precursor example | Amine | compound | [M + H]+ | Retention time (min) |
|---|---|---|---|---|---|
| 60-bn | 55 | (Tetrahydro-furan-2R-ylmethyl)-CH2-NH2 | 4-[(Tetrahydro-furan-2R-ylmethyl)-amino]-benzenesulfonic acid 2-(cyclopropanecarbonyl-amino)-1H-benzoimidazol-5-yl ester; | 456.87 | 3.23 |
| 60-bo | 55 | (Tetrahydro-furan-2S-ylmethyl)-CH2-NH2 | (Tetrahydro-furan-2S-ylmethyl)-amino]-benzenesulfonic acid 2-(cyclopropanecarbonyl-amino)-1H-benzoimidazol-5-yl ester; | 456.88 | 3.48 |
| 60-bp | 55 | Butyl-N(H)-CH2CH2-NH2 | 4-(2-Butylamino-ethylamino)-benzenesulfonic acid 2-(cyclopropanecarbonyl-amino)-1H-benzoimidazol-5-yl ester | 471.92 | 2.80 |
| 60-bq | 55 | CH3-NH-CH2CH2CH2-NH2 | 4-(3-Methylamino-propylamino)-benzenesulfonic acid 2-(cyclopropanecarbonyl-amino)-1H-benzoimidazol-5-yl ester | 443.90 | 2.54 |
| 60-br | 55 | H2N-C(O)-CH(NH2)-CH2-C(O)-NH2 | 4-(1S,2-Dicarbamoyl-ethylamino)-benzenesulfonic acid 2-(cyclopropanecarbonyl-amino)-1H-benzoimidazol-5-yl ester | 486.90 | 2.60 |
| 60-bs | 55 | CH3O-C(O)-CH(NH2)-CH2-OH | 2-{4-[2-(Cyclopropanecarbonyl-amino)-1H-benzoimidazol-5-yloxysulfonyl]-phenylamino}-3R-hydroxy-propionic acid methyl ester | 474.83 | 2.81 |
| 60-bt | 55 | H2N-C(O)-CH2CH2-NH2 | 4-(2-Carbamoyl-ethylamino)-benzenesulfonic acid 2-(cyclopropanecarbonyl-amino)-1H-benzoimidazol-5-yl ester | 443.86 | 2.71 |
| 60-bu | 55 | CH3O-CH2CH2CH2-NH2 | 4-(3-Methoxy-propylamino)-benzenesulfonic acid 2-(cyclopropanecarbonyl-amino)-1H-benzoimidazol-5-yl ester | 444.89 | 3.15 |

-continued

| n° example | Precursor example | Amine | compound | [M + H]+ | Retention time (min) |
|---|---|---|---|---|---|
| 60-bv | 55 | (3,4,5-trimethoxybenzylamine) | 4-(3,4,5-Trimethoxy-benzylamino)-benzenesulfonic acid 2-(cyclopropanecarbonyl-amino)-1H-benzoimidazol-5-yl ester | 552.85 | 3.46 |
| 60-bw | 55 | (glycinamide) | 4-(Carbamoylmethyl-amino)-benzenesulfonic acid 2-(cyclopropanecarbonyl-amino)-1H-benzoimidazol-5-yl ester | 429.88 | 2.85 |
| 60-bx | 55 | (ethyl piperidine-4-carboxylate) | 1-{4-[2-(Cyclopropanecarbonyl-amino)-1H-benzoimidazol-5-yloxysulfonyl]-phenyl}-piperidine-4-carboxylic acid ethyl ester | 512.87 | 3.81 |
| 60-by | 55 | (2-methyl-1,2-propanediamine) | 4-(2-Amino-2-methyl-propylamino)-benzenesulfonic acid 2-(cyclopropanecarbonyl-amino)-1H-benzoimidazol-5-yl ester | 443.92 | 2.48 |
| 60-bz | 55 | (methyl 3-aminopropanoate) | 3-{4-[2-(Cyclopropanecarbonyl-amino)-1H-benzoimidazol-5-yloxysulfonyl]-phenylamino}-propionic acid methyl ester | 458.88 | 3.13 |
| 60-ca | 55 | (3-morpholin-4-yl-propylamine) | 4-(3-Morpholin-4-yl-propylamino)-benzenesulfonic acid 2-(cyclopropanecarbonyl-amino)-1H-benzoimidazol-5-yl ester | 499.91 | 2.56 |
| 60-cb | 55 | (5-amino-1-pentanol) | 4-(5-Hydroxy-pentylamino)-benzenesulfonic acid 2-(cyclopropanecarbonyl-amino)-1H-benzoimidazol-5-yl ester | 458.93 | 3.08 |

| n° example | Precursor example | Amine | compound | [M + H]⁺ | Retention time (min) |
|---|---|---|---|---|---|
| 60-cc | 55 | | 4-[(5S-Amino-2,2,4S-trimethyl-cyclopentylmethyl)-amino]-benzenesulfonic acid 2-(cyclopropane-carbonyl-amino)-1H-benzoimidazol-5-yl ester | 511.94 | 3.24 |
| 60-cd | 55 | | 4-(2-Hydroxymethyl-phenylamino)-benzenesulfonic acid 2-(cyclopropanecarbonyl-amino)-1H-benzoimidazol-5-yl ester | 2.98 | 430.91 |
| 60-ce | 55 | | 4-(4-Ethoxy-phenylamino)-benzenesulfonic acid 2-(cyclopropanecarbonyl-amino)-1H-benzoimidazol-5-yl ester | 493.17 | 3.97 |
| 60-cf | 55 | | 4-Ethylamino-benzenesulfonic acid 2-(cyclopropanecarbonyl-amino)-1H-benzoimidazol-5-yl ester | 401.23 | 3.42 |
| 60-cg | 55 | | 4-(2-Sulfo-ethylamino)-benzenesulfonic acid 2-(cyclopropanecarbonyl-amino)-1H-benzoimidazol-5-yl ester | 481.00 | 2.87 |
| 60-ch | 55 | | 4-{4-[2-(Cyclopropanecarbonyl-amino)-1H-benzoimidazol-5-yloxysulfonyl]-phenylamino}-piperidine-1-carboxylic acid ethyl ester | 528.06 | 3.77 |
| 60-ci | 55 | | 4-({4-[2-(Cyclopropanecarbonyl-amino)-1H-benzoimidazol-5-yloxysulfonyl]-phenylamino}-methyl)-benzoic acid | 507.00 | 3.30 |
| 60-cj | 55 | | 4-[(1-Carbamimidoyl-piperidin-4-ylmethyl)-amino]-benzenesulfonic acid 2-(cyclopropanecarbonyl-amino)-1H-benzoimidazol-5-yl ester | 512.10 | 2.73 |

| n° example | Precursor example | Amine | compound | [M + H]+ | Retention time (min) |
|---|---|---|---|---|---|
| 60-ck | 55 | | 4-{4-[2-(Cyclopropanecarbonyl-amino)-1H-benzoimidazol-5-yloxysulfonyl]-phenyl}-piperazine-1-carboxylic acid tert-butyl ester | 542.07 | 3.85 |
| 60-cl | 55 | | 3-{4-[2-(Cyclopropanecarbonyl-amino)-1H-benzoimidazol-5-yloxysulfonyl]-phenylamino}-3-phenyl-propionic acid | 521.03 | 3.38 |
| 60-cm | 55 | | 4-Piperidin-1-yl-benzenesulfonic acid 2-(cyclopropanecarbonyl-amino)-1H-benzoimidazol-5-yl ester | 441.07 | 3.76 |
| 60-cn | 55 | | 4-(1-Methyl-4-oxo-imidazolidin-2-ylideneamino)-benzenesulfonic acid 2-(cyclopropanecarbonyl-amino)-1H-benzoimidazol-5-yl ester | 468.93 | 2.45 |
| 60-co | 55 | | 4-(4-Methyl-piperazin-1-yl)-benzenesulfonic acid 2-(cyclopropanecarbonyl-amino)-1H-benzoimidazol-5-yl ester | 456.21 | 2.94 |
| 60-cp | 55 | | 4-(3-Hydroxy-pyrrolidin-1-yl)-benzenesulfonic acid 2-(cyclopropanecarbonyl-amino)-1H-benzoimidazol-5-yl ester | 442.95 | 3.05 |
| 60-cq | 55 | | 4-(Cyclopropylmethyl-amino)-benzenesulfonic acid 2-(cyclopropanecarbonyl-amino)-1H-benzoimidazol-5-yl ester | 426.97 | 3.61 |
| 60-cr | 55 | | 4-[(2-Dimethylamino-ethyl)-methyl-amino]-benzenesulfonic acid 2-(cyclopropanecarbonyl-amino)-1H-benzoimidazol-5-yl ester | 457.98 | 2.51 |
| 60-cs | 55 | | 4-Isobutylamino-benzenesulfonic acid 2-(cyclopropanecarbonyl-amino)-1H-benzoimidazol-5-yl ester | 428.99 | 3.96 |

-continued

| n° example | Precursor example | Amine | compound | [M + H]+ | Retention time (min) |
|---|---|---|---|---|---|
| 60-ct | 55 | 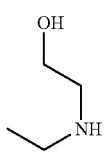 | 4-[Ethyl-(2-hydroxy-ethyl)-amino]-benzenesulfonic acid 2-(cyclopropanecarbonyl-amino)-1H-benzoimidazol-5-yl ester | 444.97 | 2.96 |
| 60-cu | 55 | 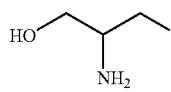 | 4-(2-Hydroxy-1-hydroxymethyl-ethylamino)-benzenesulfonic acid 2-(cyclopropanecarbonyl-amino)-1H-benzoimidazol-5-yl ester | 446.93 | 2.61 |
| 60-cv | 55 | 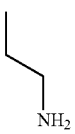 | 4-Propylamino-benzenesulfonic acid 2-(cyclopropanecarbonyl-amino)-1H-benzoimidazol-5-yl ester | 414.96 | 3.45 |
| 60-cw | 55 |  | 4-Cyclopropylamino-benzenesulfonic acid 2-(cyclopropanecarbonyl-amino)-1H-benzoimidazol-5-yl ester | 412.95 | 3.38 |
| 60-cx | 55 | 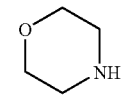 | 4-Morpholin-4-yl-benzenesulfonic acid 2-(cyclopropanecarbonyl-amino)-1H-benzoimidazol-5-yl ester | 442.95 | 3.24 |
| 60-cy | 55 | 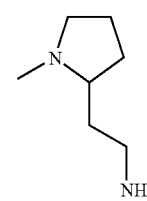 | 4-[2-(1-Methyl-pyrrolidin-2-yl)-ethylamino]-benzenesulfonic acid 2-(cyclopropanecarbonyl-amino)-1H-benzoimidazol-5-yl ester | 483.99 | 2.63 |
| 60-cz | 55 | 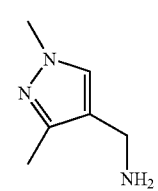 | 4-[(1,3-Dimethyl-1H-pyrazol-4-ylmethyl)-amino]-benzenesulfonic acid 2-(cyclopropane-carbonyl-amino)-1H-benzoimidazol-5-yl ester | 480.96 | 2.99 |
| 60-da | 55 | 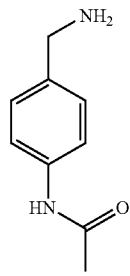 | 4-(4-Acetylamino-benzylamino)-benzenesulfonic acid 2-(cyclopropanecarbonyl-amino)-1H-benzoimidazol-5-yl ester | 519.94 | 3.45 |

| n° example | Precursor example | Amine | compound | [M + H]⁺ | Retention time (min) |
|---|---|---|---|---|---|
| 60-db | 55 | 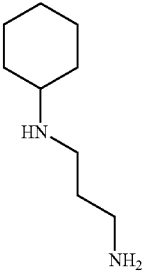 | 4-(3-Cyclohexylamino-propylamino)-benzenesulfonic acid 2-(cyclopropanecarbonyl-amino)-1H-benzoimidazol-5-yl ester | 512.02 | 2.78 |
| 60-dc | 55 | 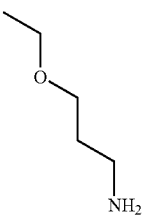 | 4-(3-Ethoxy-propylamino)-benzenesulfonic acid 2-(cyclopropanecarbonyl-amino)-1H-benzoimidazol-5-yl ester | 458.98 | 3.41 |
| 60-dd | 55 |  | 4-Pyrrolidin-1-yl-benzenesulfonic acid 2-(cyclopropanecarbonyl-amino)-1H-benzoimidazol-5-yl ester | 426.96 | 3.53 |
| 60-de | 55 | 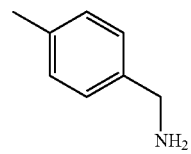 | 4-(4-Methyl-benzylamino)-benzenesulfonic acid 2-(cyclopropanecarbonyl-amino)-1H-benzoimidazol-5-yl ester | 476.96 | 3.81 |
| 60-df | 55 | 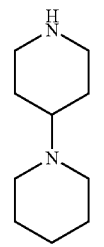 | 4-[1,4']Bipiperidinyl-1'-yl-benzenesulfonic acid 2-(cyclopropanecarbonyl-amino)-1H-benzoimidazol-5-yl ester | 524.01 | 2.76 |
| 60-dg | 55 | 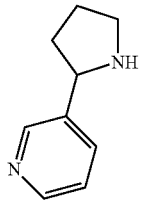 | 4-(2-Pyridin-3-yl-pyrrolidin-1-yl)-benzenesulfonic acid 2-(cyclopropanecarbonyl-amino)-1H-benzoimidazol-5-yl ester | 503.96 | 2.76 |
| 60-dh | 55 | 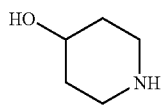 | 4-(4-Hydroxy-piperidin-1-yl)-benzenesulfonic acid 2-(cyclopropanecarbonyl-amino)-1H-benzoimidazol-5-yl ester | 456.97 | 2.90 |
| 60-di | 55 | 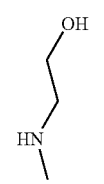 | 4-[(2-Hydroxy-ethyl)-methyl-amino]-benzenesulfonic acid 2-(cyclopropanecarbonyl-amino)-1H-benzoimidazol-5-yl ester | 430.97 | 2.85 |

| n° example | Precursor example | Amine | compound | [M + H]+ | Retention time (min) |
|---|---|---|---|---|---|
| 60-dj | 55 | (2-amino-3-hydroxypyridine) | 4-(3-Hydroxy-pyridin-2-ylamino)-benzenesulfonic acid 2-(cyclopropane-carbonyl-amino)-1H-benzoimidazol-5-yl ester | 465.93 | 2.88 |
| 60-dk | 55 | (4-(aminomethyl)piperidine-1-carboxamide) | 4-[(1-Carbamoyl-piperidin-4-ylmethyl)-amino]-benzenesulfonic acid 2-(cyclopropane-carbonyl-amino)-1H-benzoimidazol-5-yl ester | 513.00 | 2.96 |
| 60-dl | 55 | (2-(1H-pyrrol-1-yl)ethanamine) | 4-(2-Pyrrol-1-yl-ethylamino)-benzenesulfonic acid 2-cyclopropanecarbonyl-amino)-1H-benzoimidazol-5-yl ester | 465.97 | 3.43 |
| 60-dm | 55 | (4-(pyrrolidin-1-yl)piperidine) | 4-(4-Cyclopentyl-piperazin-1-yl)-benzenesulfonic acid 2-(cyclopropanecarbonyl-amino)-1H-benzoimidazol-5-yl ester | 510.01 | 2.88 |
| 60-dn | 55 | (2-propoxyethanamine) | 4-(2-Propoxy-ethylamino)-benzenesulfonic acid 2-(cyclopropanecarbonyl-amino)-1H-benzoimidazol-5-yl ester | 458.99 | 3.43 |
| 60-do | 55 | (N-cyclohexyl-1,3-propanediamine) | 4-(3-Cyclohexylamino-propylamino)-benzenesulfonic acid 2-(cyclopropanecarbonyl-amino)-1H-benzoimidazol-5-yl ester | 512.03 | 2.86 |
| 60-dp | 55 | (5-amino-1H-indole) | 4-(1H-Indol-5-ylamino)-benzenesulfonic acid 2-(cyclopropanecarbonyl-amino)-1H-benzoimidazol-5-yl ester | 487.96 | 2.76 |

-continued

| n° example | Precursor example | Amine | compound | [M + H]+ | Retention time (min) |
|---|---|---|---|---|---|
| 60-dq | 55 | (H2N-CH2-C6H4-NH2, 1,4-diaminomethylbenzene structure) | 4-(4-Amino-benzylamino)-benzenesulfonic acid 2-(cyclopropanecarbonyl-amino)-1H-benzoimidazol-5-yl ester | 477.94 | 2.80 |
| 60-dr | 55 | (2S-methoxymethyl-pyrrolidine structure) | 4-(2S-Methoxymethyl-pyrrolidin-1-yl)-benzenesulfonic acid 2-(cyclopropanecarbonyl-amino)-1H-benzoimidazol-5-yl ester | 470.99 | 3.65 |
| 60-ds | 55 | (4-(2-hydroxyethyl)piperidine structure) | 4-[4-(2-Hydroxy-ethyl)-piperidin-1-yl]-benzenesulfonic acid 2-(cyclopropanecarbonyl-amino)-1H-benzoimidazol-5-yl ester | 485.01 | 3.21 |
| 60-dt | 55 | (2-(2-hydroxyethyl)piperidine structure) | 4-[2-(2-Hydroxy-ethyl)-piperidin-1-yl]-benzenesulfonic acid 2-(cyclopropanecarbonyl-amino)-1H-benzoimidazol-5-yl ester | 485.02 | 3.23 |
| 60-du | 55 | (N-isopropyl-ethylenediamine structure) | 4-(2-Isopropylamino-ethylamino)-benzenesulfonic acid 2-(cyclopropanecarbonyl-amino)-1H-benzoimidazol-5-yl ester | 458.01 | 2.73 |
| 60-dv | 55 | (H2N-CH2-CH2-COOH, β-alanine structure) | 3-{4-[2-(Cyclopropanecarbonyl-amino)-1H-benzoimidazol-5-yloxysulfonyl]-phenyl-amino}-propionic acid | 444.95 | 2.81 |
| 60-dw | 55 | (N,N'-dimethyl-ethylenediamine structure) | 4-[Methyl-(2-methylamino-ethyl)-amino]-benzenesulfonic acid 2-(cyclopropane-carbonyl-amino)-1H-benzoimidazol-5-yl ester | 443.99 | 2.46 |
| 60-dx | 55 | (3-acetylamino-pyrrolidine structure) | 4-(3-Acetylamino-pyrrolidin-1-yl)-benzenesulfonic acid 2-(cyclopropanecarbonyl-amino)-1H-benzoimidazol-5-yl ester | 483.98 | 2.88 |

-continued

| n° example | Precursor example | Amine | compound | [M + H]⁺ | Retention time (min) |
|---|---|---|---|---|---|
| 60-dy | 55 | | {4-[2-(Cyclopropane-carbonyl-amino)-1H-benzoimidazol-5-yloxy-sulfonyl]-phenylamino}-acetic acid | 430.94 | 2.88 |
| 60-dz | 55 | | 4-(4-Hydroxy-piperidin-1-yl)-benzenesulfonic acid 2-(cyclopropanecarbonyl-amino)-1H-benzoimidazol-5-yl ester | 456.98 | 2.96 |
| 60-ea | 55 | | 4-(4-Dimethylamino-benzylamino)-benzenesulfonic acid 2-(cyclopropanecarbonyl-amino)-1H-benzoimidazol-5-yl ester | 506.02 | 2.78 |
| 60-eb | 55 | | 4-(3-Imidazol-1-yl-propylamino)-benzenesulfonic acid 2-(cyclopropanecarbonyl-amino)-1H-benzoimidazol-5-yl ester | 480.98 | 2.78 |
| 60-ec | 55 | | 4-(Quinoxalin-5-ylamino)-benzenesulfonic acid 2-(cyclopropane-carbonyl-amino)-1H-benzoimidazol-5-yl ester | 500.96 | 3.41 |
| 60-ed | 55 | | 4-[4-(2-Hydroxy-ethyl)-piperazin-1-yl]-benzenesulfonic acid 2-(cyclopropanecarbonyl-amino)-1H-benzoimidazol-5-yl ester | 486.00 | 2.48 |
| 60-ef | 55 | | 4-(2-Hydroxy-1,1-dimethyl-ethylamino)-benzenesulfonic acid 2-(cyclopropanecarbonyl-amino)-1H-benzoimidazol-5-yl ester | 444.98 | 2.49 |
| 60-eg | 55 | | 1-{4-[2-(Cyclopropanecarbonyl-amino)-1H-benzoimidazol-5-yloxysulfonyl]-phenyl}-piperidine-4-carboxylic acid | 484.98 | 3.11 |

-continued

| n° example | Precursor example | Amine | compound | [M + H]+ | Retention time (min) |
|---|---|---|---|---|---|
| 60-eh | 55 | | 6-{4-[2-(Cyclopropanecarbonyl-amino)-1H-benzoimidazol-5-yloxysulfonyl]-phenylamino}-hexanoic acid methyl ester | 500.99 | 3.70 |
| 60-ei | 55 | | 4-[4-(4-Methoxy-phenyl)-piperazin-1-yl]-benzenesulfonic acid 2-(cyclopropanecarbonyl-amino)-1H-benzoimidazol-5-yl ester | 547.99 | 3.23 |
| 60-ej | 55 | | 4-[4-(2-Methoxy-ethyl)-piperazin-1-yl]-benzenesulfonic acid 2-(cyclopropanecarbonyl-amino)-1H-benzoimidazol-5-yl ester | 500.01 | 2.51 |
| 60-ek | 55 | | 4-[(2-Hydroxy-ethyl)-phenyl-amino]-benzenesulfonic acid 2-(cyclopropanecarbonyl-amino)-1H-benzoimidazol-5-yl ester | 492.96 | 3.65 |
| 60-el | 55 | | 4-[(Furan-2-ylmethyl)-amino]-benzenesulfonic acid 2-(cyclopropane-carbonyl-amino)-1H-benzoimidazol-5-yl ester | 452.94 | 3.38 |
| 60-em | 55 | | 4-(4-Carbamoyl-piperidin-1-yl)-benzenesulfonic acid 2-(cyclopropanecarbonyl-amino)-1H-benzoimidazol-5-yl ester | 483.98 | 2.90 |
| 60-en | 55 | | 4-(3-Methyl-piperazin-1-yl)-benzenesulfonic acid 2-(cyclopropanecarbonyl-amino)-1H-benzoimidazol-5-yl ester | 456.00 | 2.54 |
| 60-eo | 55 | | 4-(2,6-Dimethyl-morpholin-4-yl)-benzenesulfonic acid 2-(cyclopropanecarbonyl-amino)-1H-benzoimidazol-5-yl ester | 471.01 | 3.61 |

| n° example | Precursor example | Amine | compound | [M + H]+ | Retention time (min) |
|---|---|---|---|---|---|
| 60-ep | 55 | (4-phenylpiperazine) | 4-(4-Phenyl-piperazin-1-yl)-benzenesulfonic acid 2-(cyclopropanecarbonyl-benzoimidazol-5-yl ester | 518.00 | 3.71 |
| 60-eq | 55 | (4-(pyridin-2-yl)piperazine) | 4-(4-Pyridin-2-yl-piperazin-1-yl)-benzenesulfonic acid 2-(cyclopropanecarbonyl-amino)-1H-benzoimidazol-5-yl ester | 519.00 | 2.70 |
| 60-er | 55 | (N,N-diethyl-4-methylpentane-1,4-diamine) | 4-(4-Diethylamino-1-methyl-butylamino)-benzenesulfonic acid 2-(cyclopropanecarbonyl-amino)-1H-benzoimidazol-5-yl ester | 514.06 | 2.98 |
| 60-es | 55 | (ethyl piperazine-1-carboxylate) | 4-{4-[2-(Cyclopropanecarbonyl-amino)-1H-benzoimidazol-5-yloxysulfonyl]-phenyl}-piperazine-1-carboxylic acid ethyl ester | 513.99 | 3.38 |
| 60-et | 55 | (5-amino-naphthalen-1-ol) | 4-(5-Hydroxy-naphthalen-1-ylamino)-benzenesulfonic acid 2-(cyclopropanecarbonyl amino)-1H-benzoimidazol-5-yl ester | 514.95 | 3.35 |
| 60-eu | 55 | (4-(2-aminoethyl)-2-methoxyphenol) | 4-[2-(4-Hydroxy-3-methoxy-phenyl)-ethylamino]-benzenesulfonic acid 2-(cyclopropanecarbonyl-amino)-1H-benzoimidazol-5-yl ester | 522.97 | 2.88 |

| n° example | Precursor example | Amine | compound | [M + H]+ | Retention time (min) |
|---|---|---|---|---|---|
| 60-ev | 55 | | 4-(9H-Purin-6-ylamino)-benzenesulfonic acid 2-(cyclopropanecarbonyl-amino)-1H-benzoimidazol-5-yl ester | 490.94 | 2.71 |
| 60-ew | 55 | | 1-{4-[2-(Cyclopropanecarbonyl-amino)-1H-benzoimidazol-5-yloxysulfonyl]-phenyl}-piperidine-3-carboxylic acid | 484.98 | 3.18 |
| 60-ex | 55 | | 4-(3,3-Dimethyl-piperidin-1-yl)-benzenesulfonic acid 2-(cyclopropanecarbonyl-amino)-1H-benzoimidazol-5-yl ester | 469.03 | 4.18 |
| 60-ey | 55 | | 4-(4-Methyl-piperidin-1-yl)-benzenesulfonic acid 2-(cyclopropanecarbonyl-amino)-1H-benzoimidazol-5-yl ester | 455.02 | 3.83 |
| 60-ez | 55 | | 4-(2-Pyridin-2-yl-ethylamino)-benzenesulfonic acid 2-(cyclopropanecarbonyl-amino)-1H-benzoimidazol-5-yl ester | 477.98 | 2.58 |
| 60-fa | 55 | | 4-(3-Hydroxymethyl-phenyl-amino)-benzene-sulfonic acid 2-(cyclopropanecarbonyl-amino)-1H-benzoimidazol-5-yl ester | 478.98 | 2.80 |
| 60-fb | 55 | | 4-(2-Oxo-2,3-dihydro-1H-pyrimidin-4-ylideneamino)-benzenesulfonic acid 2-(cyclopropanecarbonyl-amino)-1H-benzoimidazol-5-yl ester | 466.94 | 2.46 |
| 60-fc | 55 | | 4-(3-Piperidin-1-yl-propylamino)-benzenesulfonic acid 2-(cyclopropanecarbonyl-amino)-1H-benzoimidazol-5-yl ester | 498.05 | 2.85 |

| n° example | Precursor example | Amine | compound | [M + H]+ | Retention time (min) |
|---|---|---|---|---|---|
| 60-fd | 55 | | 4-[2-(1H-Indol-3-yl)-ethylamino]-benzenesulfonic acid 2-(cyclopropanecarbonyl-amino)-1H-benzoimidazol-5-yl ester | 515.98 | 3.89 |
| 60-fe | 55 | | 4-(5-Carbamoyl-1H-imidazol-4-ylamino)-benzenesulfonic acid 2-(cyclopropanecarbonyl-amino)-1H-benzoimidazol-5-yl ester | 481.96 | 2.68 |
| 60-ff | 55 | | 4-(1-Hydroxymethyl-butylamino)-benzenesulfonic acid 2-(cyclopropanecarbonyl-amino)-1H-benzoimidazol-5-yl ester | 459.01 | 3.33 |
| 60-fg | 55 | | 4-(1-Benzyl-piperidin-4-ylamino)-benzenesulfonic acid 2-(cyclopropane-carbonyl-amino)-1H-benzoimidazol-5-yl ester | 546.04 | 2.81 |
| 60-fh | 55 | | 4-{4-[2-(2-Hydroxy-ethoxy)-ethyl]-piperazin-1-yl}-benzenesulfonic acid 2-(cyclopropane-carbonyl-amino)-1H-benzoimidazol-5-yl ester | 530.01 | 2.49 |
| 60-fi | 55 | | 4-(4-Methyl-[1,4]diazepan-1-yl)-benzenesulfonic acid 2-(cyclopropanecarbonyl-amino)-1H-benzoimidazol-5-yl ester | 470.03 | 2.48 |

-continued

| n° example | Precursor example | Amine | compound | [M + H]⁺ | Retention time (min) |
|---|---|---|---|---|---|
| 60-fj | 55 | 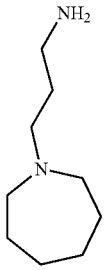 | 4-(3-Azepan-1-yl-propylamino)-benzenesulfonic acid 2-(cyclopropanecarbonyl-amino)-1H-benzoimidazol-5-yl ester | 512.06 | 2.73 |
| 60-fk | 55 | 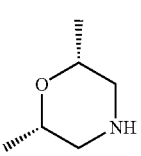 | 4-(2,6-cis-Dimethyl-morpholin-4-yl)-benzenesulfonic acid 2-(cyclopropanecarbonyl-amino)-1H-benzoimidazol-5-yl ester | 512.04 | 3.73 |
| 60-fl | 55 | 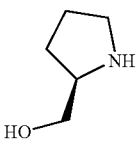 | 4-(2S-Hydroxymethyl-pyrrolidin-1-yl)-benzenesulfonic acid 2-(cyclopropanecarbonyl-amino)-1H-benzoimidazol-5-yl ester | 457.00 | 3.19 |
| 60-fm | 55 | 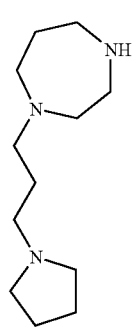 | 4-[4-(3-Pyrrolidin-1-yl-propyl)-[1,4]diazepan-1-yl]-benzenesulfonic acid 2-(cyclopropanecarbonyl-amino)-1H-benzoimidazol-5-yl ester | 567.07 | 2.39 |

Example 61

Preparation of 4-trifluoromethoxy-benzenesulfonic acid 2-methoxycarbonylamino-1H-benzoimidazol-5-yl ester

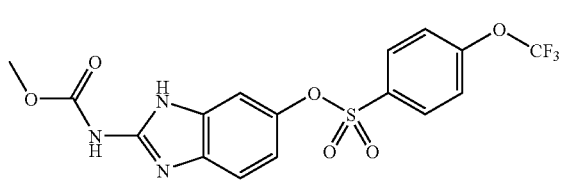

step 1: 7.82 g of 4-amino-3-nitrophenol in 460 ml of methanol were hydrogenated with catalytic amount of palladium on carbon (800 mg, 10% Pd/C). After hydrogen uptake was complete, the catalyst was filtered off, washed with methanol and the filtrate was concentrated under reduced pressure to give 6 g of crude 3,4-diaminophenol.

Step 2: 6 g of 3,4-diaminophenol were combined with 9.8 g of 1,3-bis(methoxycarbonyl)-2-methyl-2-thiopseudourea in 50 ml methanol and 30 ml acetic acid. The reaction mixture was refluxed for 4 hours. Solvents were then evaporated under reduce pressure yielding 10.8 g crude (5-hydroxy-1H-benzoimidazol-2-yl)-carbamic acid methyl ester. The residue was subjected to flash chromatography eluting with a mixture of dichloromethane-methanol (9:1; v/v) to give 5.6 g of a beige solid. Mass spectrum: 208 [M+H]⁺, retention time=0.56 minute.

Step 3: A stirred solution of (5-hydroxy-1H-benzoimidazol-2-yl)-carbamic acid methyl ester (100 mg) and 4-trifluoromethoxy-benzenesulfonyl chloride (126 mg) in acetone (3 ml) was treated with triethylamine (130 µl). After stirring at ambient temperature for 4 hours, the reaction mixture was evaporated. The residue was subjected to flash chromatography on silica eluting with a mixture of ethyl acetate and heptane (1:1, v/v) to give 4-trifluoromethoxy-benzenesulfonic acid 2-methoxycarbonylamino-1H-benzoimidazol-5-yl ester (65 mg) as an off-white solid Mass spectrum: 432 [M+H]⁺; retention time=15.04 minutes.

Example 62

By using a method similar to that for the preparation of example 61, combining (5-hydroxy-1H-benzoimidazol-2-yl)-carbamic acid methyl ester with suitable benzene sulfonyl chloride were obtained the following compounds that were characterized by analytical LC/MS ([M+H]+ and retention time given in the following table).

| Example | Benzene sulfonyl chloride | Compound | Retention time (minutes) | Mass [M + H]+ |
|---|---|---|---|---|
| 62-a | | 3,5-Dimethyl-isoxazole-4-sulfonic acid 2-methoxycarbonylamino-1H-benzoimidazol-5-yl ester | 15.87 | 367 |
| 62-b | | Thiophene-2-sulfonic acid 2-methoxycarbonylamino-1H-benzoimidazol-5-yl ester | 14.95 | 354 |
| 62-c | | 5-Isoxazol-3-yl-thiophene-2-sulfonic acid 2-methoxycarbonylamino-1H-benzoimidazol-5-yl ester | 12.58 | 421 |
| 62-d | | 2-Fluoro-benzenesulfonic acid 2-methoxycarbonylamino-1H-benzoimidazol-5-yl ester | 10.37 | 366 |
| 62-e | | 5-(1-Methyl-5-trifluoromethyl-1H-pyrazol-3-yl)-thiophene-2-sulfonic acid 2-methoxycarbonylamino-1H-benzoimidazol-5-yl ester | 16.58 | 502 |
| 62-f | | 3-Trifluoromethoxy-benzenesulfonic acid 2-methoxycarbonylamino-1H-benzoimidazol-5-yl ester | 4.06 | 432 |
| 62-g | | 2-Trifluoromethoxy-benzenesulfonic acid 2-methoxycarbonylamino-1H-benzoimidazol-5-yl ester | 13.06 | 432 |
| 62-h | | 2,6-Difluoro-benzenesulfonic acid 2-methoxycarbonylamino-1H-benzoimidazol-5-yl ester | 9.76 | 384 |

-continued

| Example | Benzene sulfonyl chloride | Compound | Retention time (minutes) | Mass [M + H]+ |
|---|---|---|---|---|
| 62-i | (3-methoxy-benzenesulfonyl chloride structure) | 3-Methoxy-benzenesulfonic acid 2-methoxycarbonylamino-1H-benzoimidazol-5-yl ester | 10.16 | 378 |
| 62-j | (3-chlorosulfonyl-thiophene-2-carboxylic acid methyl ester structure) | 3-(2-Methoxycarbonylamino-1H-benzoimidazol-5-yloxysulfonyl)-thiophene-2-carboxylic acid methyl ester | 8.07 | 412 |
| 62-k | (3,4-dimethoxy-benzenesulfonyl chloride structure) | 3,4-Dimethoxy-benzenesulfonic acid 2-methoxycarbonylamino-1H-benzoimidazol-5-yl ester | 9.32 | 408 |
| 62-l | (3-nitro-benzenesulfonyl chloride structure) | 3-Nitro-benzenesulfonic acid 2-methoxycarbonylamino-1H-benzoimidazol-5-yl ester | 11.56 | 393 |
| 62-m | (3-trifluoromethyl-benzenesulfonyl chloride structure) | 3-Trifluoromethyl-benzenesulfonic acid 2-methoxycarbonylamino-1H-benzoimidazol-5-yl ester | 14.19 | 416 |
| 62-n | (2-cyano-benzenesulfonyl chloride structure) | 2-Cyano-benzenesulfonic acid 2-methoxycarbonylamino-1H-benzoimidazol-5-yl ester | 9.43 | 373 |
| 62-o | (2-trifluoromethyl-benzenesulfonyl chloride structure) | 2-Trifluoromethyl-benzenesulfonic acid 2-methoxycarbonylamino-1H-benzoimidazol-5-yl ester | 13.26 | 416 |
| 62-p | (2,4-difluoro-benzenesulfonyl chloride structure) | 2,4-Difluoro-benzenesulfonic acid 2-methoxycarbonylamino-1H-benzoimidazol-5-yl ester | 11.35 | 384 |

-continued

| Example | Benzene sulfonyl chloride | Compound | Retention time (minutes) | Mass [M + H]$^+$ |
|---|---|---|---|---|
| 62-q | 5-fluoro-2-methyl-benzenesulfonyl chloride | 5-Fluoro-2-methyl-benzenesulfonic acid 2-methoxycarbonylamino-1H-benzoimidazol-5-yl ester | 12.93 | 380 |
| 62-r | 3-fluoro-benzenesulfonyl chloride | 3-Fluoro-benzenesulfonic acid 2-methoxycarbonylamino-1H-benzoimidazol-5-yl ester | 11.19 | 366 |
| 62-s | 4-cyano-benzenesulfonyl chloride | 4-Cyano-benzenesulfonic acid 2-methoxycarbonylamino-1H-benzoimidazol-5-yl ester | 10.37 | 373 |
| 62-t | 2,5-dimethoxy-4-(methoxycarbonyl)thiophene-2-sulfonyl chloride | 2-Methoxy-5-(2-methoxycarbonylamino-3H-benzoimidazol-5-yloxysulfonyl)-thiophene-3-carboxylic acid methyl ester | 8.52 | 442 |
| 62-u | 1,3,5-trimethyl-1H-pyrazole-4-sulfonyl chloride | 1,3,5-Trimethyl-1H-pyrazole-4-sulfonic acid 2-methoxycarbonylamino-3H-benzoimidazal-5-yl ester | 6.96 | 380 |
| 62-v | 6-morpholin-4-yl-pyridine-3-sulfonyl chloride | 6-Morpholin-4-yl-pyridine-3-sulfonic acid 2-methoxycarbonylamino-3H-benzoimidazol-5-yl ester | 7.82 | 434 |
| 62-w | 2,4,6-trifluoro-benzenesulfonyl chloride | 2,4,6-Trifluoro-benzenesulfonic acid 2-methoxycarbonylamino-1H-benzoimidazol-5-yl ester | 3.34 | 402 |

Example 63

Preparation of 4-benzyloxy-benzenesulfonic acid 2-methoxycarbonylamino-1H-benzoimidazol-5-yl ester

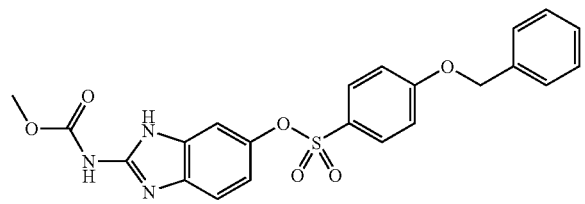

Step 1: A stirred solution of 4-amino-3-nitro-phenol (3 g) and benzoic acid 4-chlorosulfonyl-phenyl ester (5.7 g) in acetone (80 ml) was treated with triethylamine (5.4 ml). After stirring at ambient temperature for 14 hours, the reaction mixture was evaporated. The residue was triturated with diisopropylic ether, filtered off and dried under vacuum to give 5.22 g of benzoic acid 4-amino-3-nitro-phenoxysulfonyl)-phenyl ester (5.22 g) as a yellow solid Mass spectrum: 401 [M+H]$^+$; retention time=4.59 minutes.

Step 2: A solution benzoic acid 4-amino-3-nitro-phenoxysulfonyl)-phenyl ester (3 g) and 2N aqueous solution of sodium hydroxyde in methanol (55 ml) was reluxed for 2 hours. The reaction mixture was concentrated and water (100 ml) and ethyl acetate (100 ml) were added. The organic layer was dried over magnesium sulfate then evaporated to give 1.77 g of crude 4-hydroxy-benzenesulfonic acid 4-amino-3-nitro-phenyl ester.

Step 3: A solution of cesium carbonate (156 mg) in water (0.3 ml) was added to a solution of 4-hydroxy-benzenesulfonic acid 4-amino-3-nitro-phenyl ester (150 mg) and benzyl bromide (58 μl) in dimethylformamide (3 ml). The reaction mixture was heated at 80° C. for 3 hours then allowed to cool to ambient temperature, poured into water (25 ml) and extracted three times with ethyl acetate (30 ml). The combined extracts were dried over magnesium sulfate then evaporated to give 189 mg of crude 4-benzyloxy-benzenesulfonic acid 4-amino-3-nitrophenyl ester.

Step 4: Sodium dithionite (624 mg) was added to a solution of 4-benzyloxy-benzenesulfonic acid 4-amino-3-nitrophenyl ester (180 mg) and sodium hydroxyde (0.5 N, 3.1 ml) in ethanol (6 ml) at 80° C. The reaction mixture was stirred at 80° C. for 10 minutes then filtered and the filtrate was evaporated. The residue was extracted three times with ethyl acetate (15 ml). The combined extracts were dried over magnesium sulfate then evaporated to 137 mg of crude 4-benzyloxy-benzenesulfonic acid 3,4-diamino-phenyl ester.

Step 5: preparation of 4-Benzyloxy-benzenesulfonic acid 2-methoxycarbonylamino-1H-benzoimidazol-5-yl ester To a solution of 4-benzyloxy-benzenesulfonic acid 3,4-diamino-phenyl ester (134 mg) in acetic acid (0.83 ml) and methanol (2.5 ml) at 80° C. was added 1,3-bis(methoxycarbonyl)-2-methyl-2-thiopseudourea (89 mg). The reaction mixture was refluxed for 2 hours then allowed to cool to ambient temperature and stirred at this temperature for 14 hours. The resultant precipitate was filtered, washed with diethyl ether and dried under vacuum to afford 4-benzyloxy-benzenesulfonic acid 2-methoxycarbonylamino-1H-benzoimidazol-5-yl ester as a beige solid. Mass spectrum: 454 [M+H]$^+$; retention time=11.46 minutes.

Example 64

By using a method similar to that for the preparation of example 63, combining in step 3 the 4-hydroxy-benzenesulfonic acid 4-amino-3-nitro-phenyl ester with suitable alkyl halide were obtained the following compounds that were characterized by analytical LC/MS ([M+H]$^+$ and retention time given in the following table).

| Example | Alkyl halide | Compound | Retention time (minutes) | Mass [M + H]$^+$ |
|---|---|---|---|---|
| 64-a | ⌒I | 4-Ethoxy-benzenesulfonic acid 2-methoxycarbonylamino-3H-benzoimidazol-5-yl ester | 12.34 | 392 |
| 64-d | Cl⌒N(morpholine)O | 4-(2-Morpholin-4-yl-ethoxy)-benzenesulfonic acid 2-methoxycarbonylamino-3H-benzoimidazol-5-yl ester | 3.24 | 477 |
| 64-c | Br⌒O⌒ | 4-(2-Methoxy-ethoxy)-benzenesulfonic acid 2-methoxycarbonylamino-3H-benzoimidazol-5-yl ester | 9.97 | 422 |
| 64-d | Cl⌒N(piperidine) | 4-(2-piperidin-1-yl-ethoxy)-benzenesulfonic acid 2-methoxycarbonylamino-3H-benzoimidazol-5-yl ester | 3.94 | 475 |
| 64-e | Br⌒C(=O)O⌒ | [4-(2-Methoxycarbonylamino-3H-benzoimidazol-5-yloxysulfonyl)-phenoxy]-acetic acid | 7.23 | 422 |

Example 65

Preparation of 4-(2-oxo-2-pyrrolidin-1-yl-ethoxy)-benzenesulfonic acid 2-methoxycarbonylamino-1H-benzoimidazol-5-yl-ester

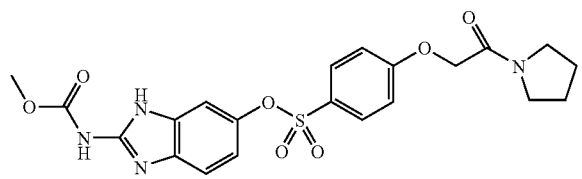

A solution of [4-(2-methoxycarbonylamino-3H-benzoimidazol-5-yloxysulfonyl)-phenoxy]-acetic acid (40 mg, example 64-e) in dry dimethylformamide (3 ml) was treated with N-{(dimethylamino)(1H-1,2,3-triazolo[4,5-b]pyridin-1-yl)methylene}-N-methylmethanaminium hexafluorophosphate N-oxide (39 mg) and diisopropylethylamine (50 µl). After stirring at ambient temperature for 30 minutes, pyrrolidine (21 µl) was added and the mixture stirred at room temperature for a further 3 hours. The solvent was removed in vacuo and the residue was purified by triggered LC/MS to give 4-(2-oxo-2-pyrrolidin-1-yl-ethoxy)-benzenesulfonic acid 2-methoxycarbonylamino-1H-benzoimidazol-5-yl-ester as an off-white solid. Mass spectrum: 475[M+H]+; retention time=8.39 minutes.

Example 66

By using a method similar to that for the preparation of example 65, combining [4-(2-methoxycarbonylamino-3H-benzoimidazol-5-yloxysulfonyl)-phenoxy]-acetic acid with suitable amine were obtained the following compounds that were characterized by analytical LC/MS ([M+H]+ and retention time given in the following table).

Example 67

Preparation of 4-(cyclopropylmethyl-amino)-benzene sulfonic acid 2-methoxycarbonylamino-1H-benzoimidazol-5-yl ester

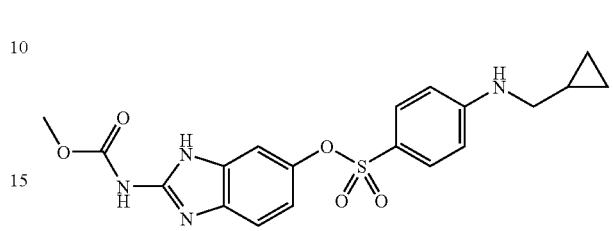

Step 1: preparation of 4-(cyclopropylmethyl-amino)-benzenesulfonic acid 4-amino-3-nitro-phenyl ester A solution of 4-fluoro-benzenesulfonic acid 4-amino-3-nitro-phenyl ester (800 mg) and cyclopropylmethylamine (890 µl) in N-methylpyrrolidinone (8 ml) was heated at 110° C. in a sealed tube for 14 hours. The reaction mixture was then poured into water (150 ml) and extracted three times with ethyl acetate (40 ml). The combined extracts were dried over magnesium sulfate and then evaporated. The residue was subjected to flash chromatography on silica eluting with a mixture of ethyl acetate and heptane (50:50, v/v) to give 4-(cyclopropylmethyl-amino)-benzenesulfonic acid 4-amino-3-nitro-phenyl ester (786 mg) as a yellow solid.

Step 2: Sodium dithionite (3 g) was added to a solution of 4-(cyclopropylmethyl-amino)-benzenesulfonic acid 4-amino-3-nitro-phenyl ester (783 mg) and sodium hydroxide (0.5 N, 15 ml) in ethanol (30 ml) at 80° C. The reaction mixture was stirred at 80° C. for 10 minutes then filtered then the filtrate was evaporated. The residue was extracted three times with ethyl acetate (30 ml). The combined extracts were dried over magnesium sulfate then evaporated to give 652 mg of 4-(cyclopropylmethyl-amino)-benzenesulfonic acid 3,4-diamino-phenyl ester.

| Example | Amine | Compound | Retention time (minutes) | Mass [M + H]+ |
|---|---|---|---|---|
| 66-a | —N⏑N—H (methyl-piperazine) | 4-[2-(4-Methyl-piperazin-1-yl)-2-oxo-ethoxy]-benzenesulfonic acid 2-methoxycarbonylamino-1H-benzoimidazol-5-yl ester | 1.96 | 504 |
| 66-b | H-N(H)-CH2CH2CH2-N(Et)(Et) | 4-[(3-diethylamino-propylcarbamoyl)-methoxy]-benzenesulfonic acid 2-methoxycarbonylamino-1H-benzoimidazol-5-yl ester | 1.96 | 534 |
| 66-c | H2N-CH2-(furan-2-yl) | 4-{[(furan-2-ylmethyl)-carbamoyl]-methoxy}-benzenesulfonic acid 2-methoxycarbonylamino-1H-benzoimidazol-5-yl ester | 10.89 | 501 |

Step 3: To a solution of 4-(cyclopropylmethyl-amino)-benzenesulfonic acid 3,4-diamino-phenyl ester (648 mg) in acetic acid (4.5 ml) and methanol (40 ml) at 80° C. was added 1,3-bis(methoxycarbonyl)-2-methyl-2-thiopseudourea (580 mg). The reaction mixture was refluxed for 4 hours then allowed to cool to ambient temperature and stirred at this temperature for 14 hours. The resultant precipitate was filtered, washed with diethyl ether and dried under vacuum to afford 4-(cyclopropylmethyl-amino)-benzene sulfonic acid 2-methoxycarbonylamino-1H-benzoimidazol-5-yl ester (378 mg) as a beige solid. Mass spectrum: 417 $[M+H]^+$; retention time=13.16 minutes.

Example 68

By using a method similar to that for the preparation of example 67, combining 4-fluoro-benzenesulfonic acid 4-amino-3-nitro-phenyl ester with suitable amine in step 1 were obtained the following compounds that were characterized by analytical LC/MS ($[M+H]^+$ and retention time given in the following table).

| Example | Amine | Compound | Retention time (minutes) | Mass $[M + H]+$ |
|---|---|---|---|---|
| 68-a | 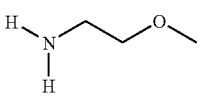 | 4-(2-methoxy-ethylamino)-benzenesulfonic acid 2-methoxycarbonylamino-1H-benzoimidazol-5-yl ester | 8.89 | 421 |
| 68-b | 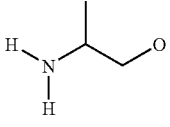 | 4-(2-hydroxy-1-methyl-ethylamino)-benzenesulfonic acid 2-methoxycarbonylamino-1H-benzoimidazol-5-yl ester | 6.84 | 421 |
| 68-c | 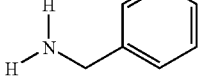 | 4-(benzylamino)-benzenesulfonic acid 2-methoxycarbonylamino-1H-benzoimidazol-5-yl ester | 4.4 | 453 |
| 68-d | 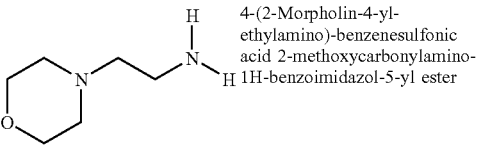 | 4-(2-Morpholin-4-yl-ethylamino)-benzenesulfonic acid 2-methoxycarbonylamino-1H-benzoimidazol-5-yl ester | 2.44 | 476 |
| 68-e | 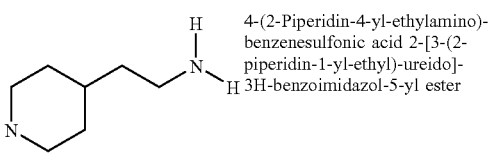 | 4-(2-Piperidin-4-yl-ethylamino)-benzenesulfonic acid 2-[3-(2-piperidin-1-yl-ethyl)-ureido]-3H-benzoimidazol-5-yl ester | 2.77 | 460 |
| 68-f | 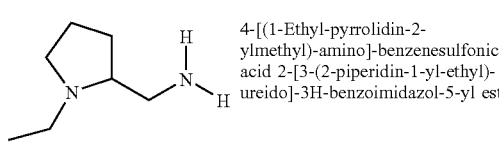 | 4-[(1-Ethyl-pyrrolidin-2-ylmethyl)-amino]-benzenesulfonic acid 2-[3-(2-piperidin-1-yl-ethyl)-ureido]-3H-benzoimidazol-5-yl ester | 2.3 | 474 |

Example 69

Preparation of 4-cyclopentylamino-benzenesulfonic acid 2-(3,4-dimethoxy-phenylamino)-1H-benzoimidazol-5-yl ester

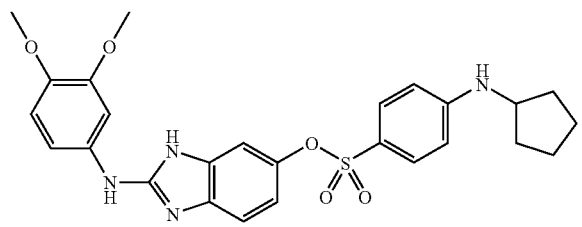

Step 1: A solution of 1-benzyl-6-methoxy-1H-benzoimidazole (3 g) in dry tetrahydrofuran (65 ml), cooled to −78° C., was treated with a solution of n-butyllithium in hexanes (12 ml, 15%). After stirring for 45 minutes the mixture was treated with N-chlorosuccinimide (2.24 g in 65 ml of tetrahydrofuran) then allowed to warm slowly to ambient temperature. The reaction mixture was allowed to stir at ambient temperature for 2 hours then treated with a saturated aqueous solution of ammonium chloride (100 ml) and extracted three times with ethyl acetate (65 ml). The combined extracts were dried over magnesium sulfate and then evaporated. The residue was subjected to flash column chromatography on silica eluting with a mixture of ethyl acetate and hexane (1:1, v/v) to 1-benzyl-2-chloro-6-methoxy-1H-benzoimidazole (2.09 g) as a yellow solid. Mass spectrum: 273 [M+H]$^+$, retention time=3.93 minutes.

Step 2: A mixture of 1-benzyl-2-chloro-6-methoxy-1H-benzoimidazole (600 mg), hydrobromic acid (48%, 11 ml) and glacial acetic acid (6 ml) was heated under reflux for 1 hour. After cooling the mixture was neutralised by addition of 10% sodium bicarbonate solution then extracted 3 times with dichloromethane (30 ml). The combined extracts were dried over magnesium sulfate and then evaporated to give 3-benzyl-2-chloro-3H-benzoimidazol-5-ol (470 mg) as a yellow solid. Mass spectrum: 259 [M+H]$^+$ retention time=3.4 minutes.

Step 3: A mixture of 3-benzyl-2-chloro-3H-benzoimidazol-5-ol (250 mg) and 4-amino veratrole (296 mg) in N-methylpyrrolidinone (3 ml) was heated at 150° C. in a sealed tube for 4 hours then allowed to cool. The reaction mixture was then poured into water (30 ml) and extracted three times with ethyl acetate (30 ml). The combined extracts were dried over magnesium sulfate and then evaporated. The residue was subjected to flash chromatography on silica eluting with a mixture of dichloromethane and methanol (95:5, v/v) to give 3-benzyl-2-(3,4-dimethoxy-phenylamino)-3H-benzoimidazol-5-ol (141 mg) as a yellow solid. Mass spectrum: 376 [M+H]$^+$ retention time: 3.44 minutes.

Step 4: A stirred solution of 3-benzyl-2-(3,4-dimethoxy-phenylamino)-3H-benzoimidazol-5-ol (141 mg) and 4-fluoro-benzenesulfonyl chloride (190 mg) in acetone (8 ml) was treated with triethylamine (258 μl). After stirring at ambient temperature for 4 hours, the reaction mixture was evaporated. The residue was subjected to flash chromatography on silica eluting with a mixture of ethyl acetate and heptane (1:1, v/v) to give 4-fluoro-benzenesulfonic acid 3-benzyl-2-(3,4-dimethoxy-phenylamino)-3H-benzoimidazol-5-yl ester (157 mg) as a yellow solid. Mass spectrum: 534 [M+H]$^+$, retention time: 3.7 minutes.

Step 5: A solution of 4-fluoro-benzenesulfonic acid 3-benzyl-2-(3,4-dimethoxy-phenylamino)-3H-benzoimidazol-5-yl ester (151 mg) and cyclopentylamine (118 μl) in N-methylpyrrolidinone (1.5 ml) was heated at 110° C. in a sealed tube for 3 hours. The reaction mixture was allowed to cool then poured into water (30 ml) and extracted three times with ethyl acetate. The combined extracts were dried over magnesium sulfate then evaporated. The residue was subjected to flash chromatography on silica eluting with a mixture of ethyl acetate and heptane (1:1, v/v) to give 4-cyclopentylamino-benzenesulfonic acid 3-benzyl-2-(3,4-dimethoxy-phenylamino)-3H-benzoimidazol-5-yl ester (122 mg) as a brown solid. Mass spectrum: 599 [M+H]$^+$, retention time=4.0 minutes.

Example 70

By using a method similar to that for the preparation of example 69, combining 3-benzyl-2-chloro-3H-benzoimidazol-5-ol with suitable amine in step 3 were obtained the following compounds that were characterized by analytical LC/MS ([M+H]$^+$ and retention time given in the following table).

| Example | Amine | Compound | Retention time (minute) | Mass [M + H]$^+$ |
|---|---|---|---|---|
| 70-a | aniline (PhNH₂) | 4-Cyclopentylamino-benzenesulfonic acid 2-phenylamino-1H-benzoimidazol-5-yl ester | 12.31 | 449 |

-continued

| Example | Amine | Compound | Retention time (minute) | Mass [M + H]+ |
|---|---|---|---|---|
| 70-b | 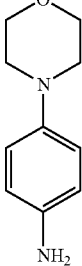 | 4-Cyclopentylamino-benzenesulfonic acid 2-(4-morpholin-4-yl-phenylamino)-1H-benzoimidazol-5-yl ester | 11.58 | 534 |
| 70-c | 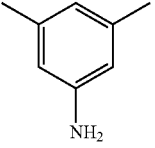 | 4-Cyclopentylamino-benzenesulfonic acid 2-(3,5-dimethyl-phenylamino)-1H-benzoimidazol-5-yl ester | 9.55 | 477 |
| 70-d | 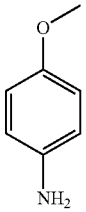 | 4-Cyclopentylamino-benzenesulfonic acid 2-(4-methoxy-phenylamino)-1H-benzoimidazol-5-yl ester | 8.69 | 479 |
| 70-e | 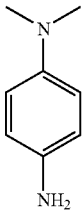 | 4-Cyclopentylamino-benzenesulfonic acid 2-(4-dimethylamino-phenylamino)-1H-benzoimidazol-5-yl ester | 8.59 | 492 |
| 70-f | 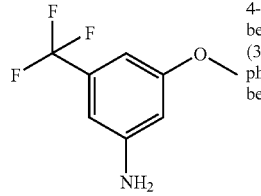 | 4-Cyclopentylamino-benzenesulfonic acid 2-(3-methoxy-5-trifluoromethyl-phenylamino)-1H-benzoimidazol-5-yl ester | 11.94 | 547 |
| 70-g | 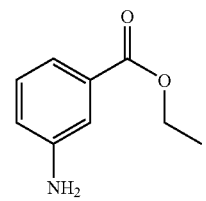 | 3-[5-(4-Cyclopentylamino-benzenesulfonyloxy)-1H-benzoimidazol-2-ylamino]-benzoic acid ethyl ester | 10.13 | 521 |

| Example | Amine | Compound | Retention time (minute) | Mass [M + H]+ |
|---|---|---|---|---|
| 70-h | | 4-Cyclopentylamino-benzenesulfonic acid 2-[(4-(4-methyl-piperazin-1-yl)-phenylamino)-1H-benzoimidazol-5-yl ester | 6.64 | 547 |

Example 71

Preparation of 4-cyclopentylamino-benzenesulfonic acid 2-(3-phenyl-propionylamino)-1H-benzoimidazol-5-yl ester

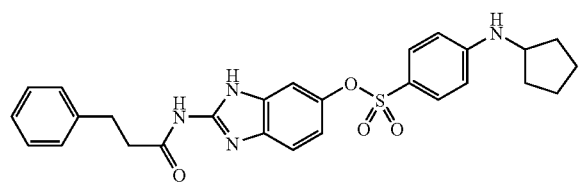

A solution of 3-phenyl propionic acid (9.7 mg) in dry dimethylformamide (0.6 ml) was treated with N-{(dimethylamino)(1H-1,2,3-triazolo[4,5-b]pyridin-1-yl)methylene}-N-methylmethanaminium hexafluorophosphate N-oxide (21 mg) and diisopropylethylamine (12 µl). After stirring at ambient temperature for 30 minutes, 4-cyclopentylamino-benzenesulfonic acid 2-amino-3H-benzoimidazol-5-yl ester (20 mg) was added and the mixture stirred at room temperature for a further 3 hours. The solvent was removed under vacuo and the residue was purified by triggered LC/MS to give 4-cyclopentylamino-benzenesulfonic acid 2-(3-phenyl-propionylamino)-1H-benzoimidazol-5-yl ester as an off-white solid (11 mg). Mass spectrum: 505 [M+H]+; retention time=4.59 minutes.

Example 72

Preparation of 4-cyclopentylamino-benzenesulfonic acid 2-[2-2-methoxy-ethoxy)-acetylamino]-1H-benzoimidazol-5-yl ester

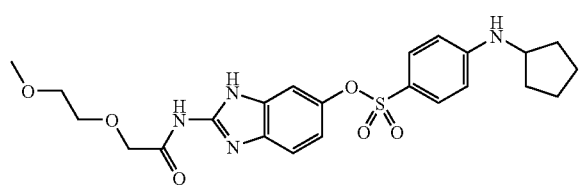

By proceeding in a manner similar to example 71 above but using (2-methoxy-ethoxy)-acetic acid there was prepared 4-cyclopentylamino-benzenesulfonic acid 2-[2-2-methoxy-ethoxy)-acetylamino]-1H-benzoimidazol-5-yl ester as an off-white solid. Mass spectrum: 489 [M+H]+; retention time=4.06 minutes.

Example 73

Preparation of 4-fluoro-benzenesulfonic acid 2-(3 (chloro-4-methoxy-benzylamino)-3H-benzoimidazol-5-yl ester

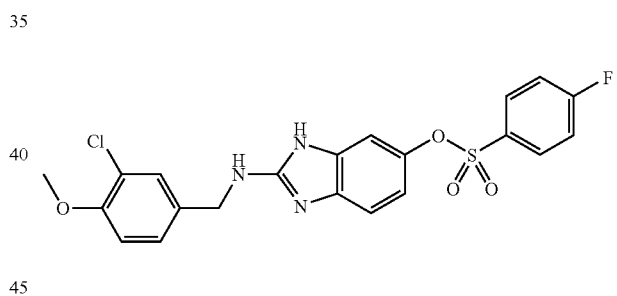

Step 1: A stirred solution of 4-fluoro-benzenesulfonic acid 2-tert-butoxycarbonylamino-3H-benzoimidazol-5-yl ester (Example 55 (step 3), 200 mg) in dry dimethylformamide (3 ml) was treated with sodium hydride (12 mg, 60% dispersion in mineral oil). After stirring for 30 minutes the mixture was treated with a solution of 3-chloro-4-methoxy-benzyl bromide (94 mg) in dimethylformamide (1 ml) and stirring was continued for a further 3 hours. The reaction mixture was poured into water (10 ml) and then extracted three times with ethyl acetate (10 ml). The combined extracts were dried over magnesium sulfate and then evaporated. The residue was subjected to flash chromatography on silica eluting with a mixture of ethyl acetate and heptane (1:2, v/v) to give 4-fluoro-benzenesulfonic acid 2-[tert-butoxycarbonyl-(3-chloro-4-methoxy-benzyl)-amino]-3H-benzoimidazol-5-yl ester (70 mg) as a beige solid.

Step 2: preparation of 4-fluoro-benzenesulfonic acid 2-(3-(chloro-4-methoxy-benzylamino)-3H-benzoimidazol-5-yl ester Trifluoroacetic acid (1 ml) was added to a solution of 4-fluoro-benzenesulfonic acid 2-[tert-butoxycarbonyl-(3-chloro-4-methoxy-benzyl)-amino]-3H-benzoimidazol-5-yl ester (67 mg) in dichloromethane (4 ml). After cooling, the mixture was neutralised by addition of saturated sodium bicarbonate solution. Water (10 ml) was added and the solution extracted three times with dichloromethane (10 ml). The combined extracts were dried over magnesium sulfate and then evaporated. The residue was subjected to flash chromatography on silica eluting with a mixture of ethyl acetate and heptane (1:1, v/v) to give 4-fluoro-benzenesulfonic acid 2-(3-(chloro-4-methoxy-benzylamino)-3H-benzoimidazol-5-yl ester (53 mg) as an off-white solid. Mass spectrum: 462 [M+H]$^+$; retention time=7.69 minutes.

Example 74

By using a method similar to that for the preparation of example 73, combining 4-fluoro-benzenesulfonic acid 2-tert-butoxycarbonylamino-3H-benzoimidazol-5-yl ester with suitable benzyl halide were obtained the following compounds that were characterized by analytical LC/MS ([M+H]$^+$ and retention time given in the following table).

Example 75

Preparation of 4-cyclopentylamino-benzenesulfonic acid 2-benzylamino-3H-benzoimidazol-5-yl ester

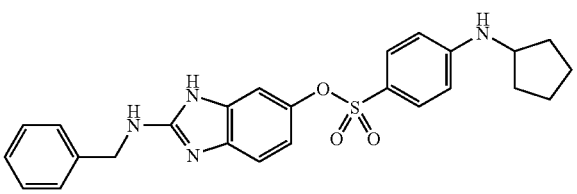

A solution of 4-fluoro-benzenesulfonic acid 2-benzylamino-3H-benzoimidazol-5-yl ester (20 mg) and cyclopentylamine (21 µl) in N-methylpyrrolidinone (0.5 ml) was heated at 110° C. in a sealed tube for 2 hours. The reaction mixture was then purified by triggered LC/MS to give 4-cyclopentylamino-benzenesulfonic acid 2-benzylamino-3H-benzoimidazol-5-yl ester as an off-white solid (4 mg). Mass spectrum: 463 [M+H]$^+$; retention time=8.35 minutes.

| Example | Benzyl halide | Compound | Retention time (minute) | Mass [M + H]$^+$ |
|---|---|---|---|---|
| 74-a | | 4-Fluoro-benzenesulfonic acid 2-[(3-phenyl-[1,2,4]-oxadiazol-5-ylmethyl)-amino]-3H-benzoimidazol-5-yl ester | 8.13 | 466 |
| 74-b | | 4-Fluoro-benzenesulfonic acid 2-(3-chloro-benzylamino)-3H-benzoimidazol-5-yl ester | 7.72 | 432 |
| 74-c | | 4-Fluoro-benzenesulfonic acid 2-(3-methoxy-benzylamino)-3H-benzoimidazol-5-yl ester | 7.31 | 428 |
| 74-d | | 4-Fluoro-benzenesulfonic acid 2-benzylamino-3H-benzoimidazol-5-yl ester | 7.43 | 398 |

Example 76

By using a method similar to that for the preparation of example 75, combining cyclopentylamine with suitable 4-fluoro-benzenesulfonic acid 2-benzylamino-3H-benzoimidazol-5-yl ester (example 73, 74a–74c) were obtained the following compounds that were characterized by analytical LC/MS ([M+H]+ and retention time given in the following table).

| Example | Precursor | Compound | Retention time (minute) | Mass [M + H]+ |
|---|---|---|---|---|
| 76-a | 74-a | 4-Cyclopentylamino-benzenesulfonic acid 2-[(3-phenyl-[1,2,4]oxadiazol-5-ylmethyl)-amino]-3H-benzoimidazol-5-yl ester | 3.91 | 531 |
| 76-b | 74-c | 4-Cyclopentylamino-benzenesulfonic acid 2-(3-methoxy-benzylamino)-3H-benzoimidazol-5-yl ester | 8.41 | 493 |
| 76-c | 73 | 4-Cyclopentylamino-benzenesulfonic acid 2-(3-chloro-4-methoxy-benzylamino)-3H-benzoimidazol-5-yl ester | 3.58 | 527 |

Example 77

Preparation of 4-(Cyclopropylmethyl-amino)-benzenesulfonic acid 2-[3-(2-morpholin-4-yl-ethyl)-ureido]-1H-benzoimidazol-5-yl ester

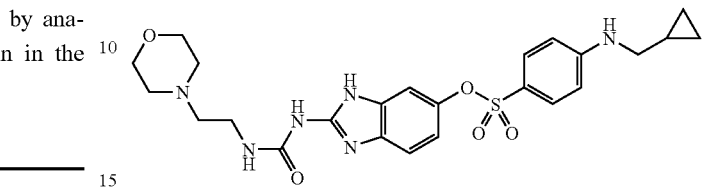

A solution of 4-(cyclopropylmethyl-amino)-benzenesulfonic acid 2-methoxycarbonylamino-3H-benzoimidazol-5-yl ester (example 67, 40 mg) and 2-(aminoethyl)-morpholine (125 mg) in tetrahydrofuran (2 ml) and N-methylpyrrolidinone (0.2 ml) was heated at 90° C. for 36 hours. The reaction mixture was then evaporated and purified by triggered LC/MS to give 4-(cyclopropylmethyl-amino)-benzenesulfonic acid 2-[3-(2-morpholin-4-yl-ethyl)-ureido]-1H-benzoimidazol-5-yl ester as an off-white solid (27 mg). Mass spectrum: 515 [M+H]+; retention time=5.97 minutes.

Example 78

By using a method similar to that for the preparation of example 77, combining 4-(substituted-amino)-benzenesulfonic acid 2-methoxycarbonylamino-3H-benzoimidazol-5-yl ester [example 63, 67, 68] with suitable amine were obtained the following compounds that were characterized by analytical LC/MS ([M+H]+ and retention time given in the following table).

| Example | Precursor | Amine | Compound | Retention time (minutes) | Mass [M + H]+ |
|---|---|---|---|---|---|
| 78-a | 67 | morpholinoethylamine | 4-(Cyclopropylmethyl-amino)-benzenesulfonic acid 2-[3-(2-morpholin-4-yl-ethyl)-ureido]-1H-benzoimidazol-5-yl ester | 5.97 | 515 |
| 78-b | 67 | 2-(aminomethyl)pyridine | 4-(Cyclopropylmethyl-amino)-benzenesulfonic acid 2-(3-pyridin-2-ylmethyl)-ureido]-1H-benzoimidazol-5-yl ester | 8.55 | 493 |
| 78-c | 67 | 2-methoxyethylamine | 4-(Cyclopropylmethyl-amino)-benzenesulfonic acid 2-[3-(2-methoxy-ethyl)-ureido]-1H-benzoimidazol-5-yl ester | 10.66 | 460 |
| 78-d | 67 | ethylamine | 4-(Cyclopropylmethyl-amino)-benzenesulfonic acid 2-[3-(2-ethyl)-ureido]-1H-benzoimidazol-5-yl ester | 11.07 | 430 |
| 78-e | 68-a | morpholinoethylamine | 4-(2-Methoxy-ethylamino)-benzenesulfonic acid 2-[3-(2-morpholin-4-yl-ethyl)-ureido]-1H-benzoimidazol-5-yl ester | 5.74 | 519 |

-continued

| Example | Precursor | Amine | Compound | Retention time (minutes) | Mass [M + H]+ |
|---|---|---|---|---|---|
| 78-f | 68-a | pyridin-2-ylmethylamine | 4-(2-Methoxy-ethylamino)-benzenesulfonic acid 2-(3-pyridin-2-ylmethyl)-ureido]-1H-benzoimidazol-5-yl ester | 6.62 | 497 |
| 78-g | 68-a | 2-methoxyethylamine | 4-(2-Methoxy-ethylamino)-benzenesulfonic acid 2-[3-(2-methoxy-ethyl)-ureido]-1H-benzoimidazol-5-yl ester | 7.39 | 464 |
| 78-h | 68-a | ethylamine | 4-(2-Methoxy-ethylamino)-benzenesulfonic acid 2-[3-(2-ethyl)-ureido]-1H-benzoimidazol-5-yl ester | 7.53 | 434 |
| 78-i | 68-b | 2-morpholin-4-yl-ethylamine | 4-(2-Hydroxy-1-methyl-ethylamino)-benzenesulfonic acid 2-[3-(2-morpholin-4-yl-ethyl)-ureido]-1H-benzoimidazol-5-yl ester | 5.36 | 519 |
| 78-j | 68-b | pyridin-2-ylmethylamine | 4-(2-Hydroxy-1-methyl-ethylamino)-benzenesulfonic acid 2-(3-pyridin-2-ylmethyl)-ureido]-1H-benzoimidazol-5-yl ester | 6.11 | 497 |
| 78-k | 68-b | 2-methoxyethylamine | 4-(2-Hydroxy-1-methyl-ethylamino)-benzenesulfonic acid 2-[3-(2-methoxy-ethyl)-ureido]-1H-benzoimidazol-5-yl ester | 6.81 | 464 |
| 78-l | 68-b | ethylamine | 4-(2-Hydroxy-1-methyl-ethylamino)-benzenesulfonic acid 2-[3-(2-ethyl)-ureido]-1H-benzoimidazol-5-yl ester | 6.94 | 434 |
| 78-m | 63 | 2-morpholin-4-yl-ethylamine | 4-Benzyloxy-benzenesulfonic acid 2-[3-(2-morpholin-4-yl-ethyl)-ureido]-1H-benzoimidazol-5-yl ester | 7.55 | 552 |
| 78-n | 63 | pyridin-2-ylmethylamine | 4-Benzyloxy-benzenesulfonic acid 2-(3-pyridin-2-ylmethyl)-ureido]-1H-benzoimidazol-5-yl ester | 8.99 | 530 |
| 78-o | 63 | 2-methoxyethylamine | 4-Benzyloxy-benzenesulfonic acid 2-[3-(2-methoxy-ethyl)-ureido]-1H-benzoimidazol-5-yl ester | 13.97 | 497 |
| 78-p | 63 | ethylamine | 4-benzyloxy-benzenesulfonic acid 2-[3-(2-ethyl)-ureido]-1H-benzoimidazol-5-yl ester | 10.12 | 467 |
| 78-r | 68-d | pyridin-2-ylmethylamine | 4-(2-Morpholin-4-yl-ethylamino)-benzenesulfonic acid 2-(3-pyridin-2-ylmethyl)-ureido]-1H-benzoimidazol-5-yl ester | 4.61 | 552 |
| 78-s | 68-d | 2-methoxyethylamine | 4-(2-Morpholin-4-yl-ethylamino)-benzenesulfonic acid 2-[3-(2-methoxy-ethyl)-ureido]-1H-benzoimidazol-5-yl ester | 1.47 | 519 |
| 78-t | 68-e | 2-morpholin-4-yl-ethylamine | 4-[(Piperidin-4-ylmethyl)-amino]-benzenesulfonic acid 2-[3-(2-morpholin-4-yl-ethyl)-ureido]-1H-benzoimidazol-5-yl ester | 4.47 | 558 |

-continued

| Example | Precursor | Amine | Compound | Retention time (minutes) | Mass [M + H]+ |
|---|---|---|---|---|---|
| 78-u | 68-e | 2-(aminomethyl)pyridine | 4-[(Piperidin-4-ylmethyl)-amino]-benzenesulfonic acid 2-(3-pyridin-2-ylmethyl)-ureido]-1H-benzoimidazol-5-yl ester | 5.12 | 536 |
| 78-v | 68-e | 2-methoxyethylamine | 4-[(Piperidin-4-ylmethyl)-amino]-benzenesulfonic acid 2-[3-(2-methoxy-ethyl)-ureido]-1H-benzoimidazol-5-yl ester | 1.47 | 503 |
| 78-w | 68-c | 4-(2-aminoethyl)morpholine | 4-Benzylamino-benzenesulfonic acid 2-[3-(2-morpholin-4-yl-ethyl)-ureido]-1H-benzoimidazol-5-yl ester | 7.16 | 551 |
| 78-x | 68-c | 2-(aminomethyl)pyridine | 4-Benzylamino-benzenesulfonic acid 2-(3-pyridin-2-ylmethyl)-ureido]-1H-benzoimidazol-5-yl ester | 8.52 | 529 |
| 78-y | 68-c | 2-methoxyethylamine | 4-Benzylamino-benzenesulfonic acid 2-[3-(2-methoxy-ethyl)-ureido]-1H-benzoimidazol-5-yl ester | 9.29 | 496 |
| 78-z | 68-c | ethylamine | 4-Benzylamino-benzenesulfonic acid 2-[3-(2-ethyl)-ureido]-1H-benzoimidazol-5-yl ester | 9.35 | 466 |
| 78-aa | 68-f | 2-(aminomethyl)pyridine | 4-[(1-ethyl-pyrrolidin-2ylmethyl)-amino]-benzenesulfonic acid 2-(3-pyridin-2-ylmethyl)-ureido]-1H-benzoimidazol-5-yl ester | 2.14 | 549 |

Example 79

Preparation of 4-(4-hydroxy-piperidin-1-yl)-benzenesulfonic acid 2-[(4-hydroxy-piperidine-1-carbonyl)-amino]-1H-benzoimidazol-5-yl ester

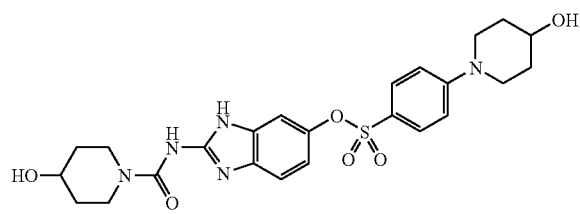

A solution of 4-fluoro-benzenesulfonic acid 2-tert-butoxycarbonylamino-3H-benzoimidazol-5-yl ester (200 mg, example 55 (Step 3) and 4-hydroxypiperidine (554 mg) in N-methylpyrrolidinone (6 ml) was heated at 110° C. for 24 hours. The reaction mixture was then poured into water (120 ml) and extracted three times with ethyl acetate (50 ml). The combined extracts were dried over magnesium sulfate and then evaporated. The residue was subjected to flash chromatography on silica eluting with a mixture of dichloromethane and methanol (95 C: 5, v/v) to give (4-hydroxy-piperidin-1-yl)-benzenesulfonic acid 2-[(4-hydroxy-piperidine-1-carbonyl)-amino]-1H-benzoimidazol-5-yl ester (125 mg) as a beige solid. Mass Spectrum: 516 [M+H]+, retention time=6.51 minutes.

Example 80

By using a method similar to that for the preparation of example 79, combining 4-fluoro-benzenesulfonic acid 2-tert-butoxycarbonylamino-3H-benzoimidazol-5-yl ester with suitable amine were obtained the following compounds that were characterized by analytical LC/MS ([M+H]+ and retention time given in the following table).

| Example | Amine | Compound | Retention time (minutes) | Mass [M + H]+ |
|---|---|---|---|---|
| 80-a | | 4-(4-Methyl-piperazin-1-yl)-benzenesulfonic acid 2-[(4-methyl-piperazin-1-carbonyl)-amino]-3H-benzoimidazol-5-yl ester | 0.53 | 514 |
| 80-b | | 4-[(tetrahydro-pyran-4-ylmethyl)-amino]-benezenesulfonic acid 2-[3-(tetrahydro-pyran-4-ylmethyl)-ureido]-3H-benzoimidazol-5-yl ester | 8.14 | 544 |
| 80-c | | 4-(2-Fluoro-ethylamino)-benzenesulfonic acid 2-[3-(2-fluoro-ethyl)-ureido]-3H-benzoimidazol-5-yl ester | 7.82 | 440 |
| 80-d | | 4-(2-piperidin-1-yl-ethylamino)-benzenesulfonic acid 2-[3-(2-piperidin-1-yl-ethyl)-ureido]-3H-benzoimidazol-5-yl ester | 0.5 | 440 |
| 80-e | | 4-phenethylamino-benzenesulfonic acid 2-(3-phenethyl-ureido)-3H-benzoimidazol-5-yl ester | 4.4 | 556 |
| 80-f | | 4-[3-(2-oxo-pyrrolidin-1-yl)-propylamino]-benzenesulfonic acid 2-{3-[3-(2-owo-pyrrolidin-1-yl)-propyl]-ureido}-3H-benzoimidazol-5-yl ester | 3.09 | 598 |
| 80-g | | 4-(4-fluoro-benzylamino)-benzenesulfonic acid 2-[3-(4-fluoro-benzyl)-ureido]-3H-benzoimidazol-5-yl ester | 4.25 | 564 |
| 80-h | | 4-(2-hydroxy-2-methyl-propylamino)-benzenesulfonic acid 2-[3-(2-hydroxy-3-methyl-propyl)-ureido]-3H-benzoimidazol-5-yl ester | 7.02 | 492 |
| 80-i | | 4-(3-hydroxy-propylamino)-benzenesulfonic acid 2-[3-(3-hydroxy-propyl)-ureido]-3H-benzoimidazol-5-yl ester | 2.7 | 464 |
| 80-j | | 4-(2,2,6,6-tetramethyl-piperidin-4-ylamino)-benzenesulfonic acid 2-[3-(2,2,6,6-tetramethyl-piperidin-4-yl)-ureido]-3H-benzoimidazol-5-yl ester | 2.44 | 626 |
| 80-k | | 4-(2-dimethylamino-ethylamino)-benzene sulfonic acid 2-[3-(2-dimethylamino-ethyl)-ureido]-3H-benzoimidazol-5-yl ester | 0.70 | 490 |
| 80-l | | 4-morpholin-4-yl-benzenesulfonic acid 2-[(morpholine-4-carbonyl)-amino]-3H-benzoimidazol-5-yl ester | 3.16 | 488 |

-continued

| Example | Amine | Compound | Retention time (minutes) | Mass [M + H]+ |
|---|---|---|---|---|
| 80-m | MeO-CH2-CH(OH)-CH2-NH-H | 4-(2-Hydroxy-3-methoxy-propylamino)-benzenesulfonic acid 2-[3-(2-hydroxy-3-methoxy-propyl)-ureido]-3H-benzoimidazol-5-yl ester | 4.71 | 524 |
| 80-n | (pyridin-2-ylmethyl)amine structure | 4-[(Pyridin-2-ylmethyl)-amino]-benzenesulfonic acid 2-(3-pyridin-2-ylmethyl-ureido)-3H-benzoimidazol-5-yl ester | 5.53 | 530 |
| 80-o | HO-CH(CH3)-CH2-NH-H | 4-(2-hydroxy-propylamino)-benzenesulfonic acid 2-[3-(2-hydroxy-propyl)-ureido]-3H-benzoimidazol-5-yl ester | 2.7 | 463 |
| 80-p | 4-methoxybenzylamine structure | 4-(4-methoxy-benzylamino)-benzenesulfonic acid 2-[3-(4-methoxy-benzyl)-ureido]-3H-benzoimidazol-5-yl ester | 4.43 | 588 |
| 80-q | 2-(pyrrolidin-1-yl)ethylamine structure | 4-(2-pyrrolidin-1-yl-ethylamino)-benzenesulfonic acid 2-[3-(2-pyrrolidin-1-yl-ethyl)-ureido]-3H-benzoimidazol-5-yl ester | 2.19 | 542 |
| 80-r | 1-phenylethylamine structure | 4-(1-phenyl-ethylamino)-benzenesulfonic acid 2-[3-(1-phenyl-ethyl)-ureido]-3H-benzoimidazol-5-yl ester | 4.63 | 556 |
| 80-s | Et2N-CH2-CH2-NH-H | 4-(2-diethylamino-ethylamino)-benzene sulfonic acid 2-[3-(2-diethylamino-ethyl)-ureido]-3H-benzoimidazol-5-yl ester | 2.75 | 546 |
| 80-t | 1-(hydroxymethyl)cyclopentylamine structure | 4-(1-hydroxymethyl-cyclopentylamino)-benzenesulfonic acid 2-[3-(1-hydroxymethyl-cyclopentyl)-ureido]-3H-benzoimidazol-5-yl ester | 3.45 | 544 |
| 80-u | MeO2C-CH2-CH2-NH-H | 3-(4-{2-[3-(3-Methoxycarbonyl-ethyl)-ureido]-1H-benzoimidazol-5-yloxysulfonyl}-phenylamino)-propionic acid methyl ester | 3.26 | 520 |

Example 81

Preparation of 4-(4-Hydroxy-piperidin-1-yl)-benzenesulfonic acid 2-[3-(2-morpholin-4-yl-ethyl)-ureido]-1H-benzoimidazol-5-yl ester

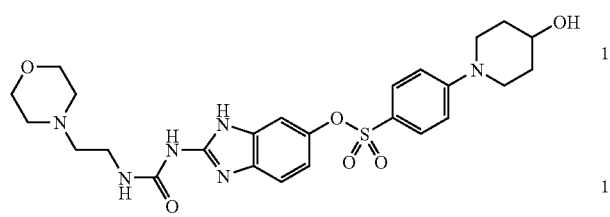

A solution of 4-(4-hydroxy-piperidin-1-yl)-benzenesulfonic acid 2-[(4-hydroxy-piperidine-1-carbonyl)-amino]-1H-benzoimidazol-5-yl ester (example 79, 20 mg) and 2-(aminomethyl)-morpholine (50 mg) in tetrahydrofuran (1 ml) and N-methylpyrrolidinone (0.2 ml) was heated at 95° C. for 22 hours. The reaction mixture was then evaporated and purified by triggered LC/MS to give 4-(4-hydroxy-piperidin-1-yl)-benzenesulfonic acid 2-[3-(2-morpholin-4-yl-ethyl)-ureido]-1H-benzoimidazol- 5-yl ester as an off-white solid (7 mg). Mass spectrum: 545 [M+H]$^+$; retention time=5.47 minutes.

Example 82

By using a method similar to that for the preparation of example 81, combining [example 80a–u] with suitable amine was obtained the following compounds that were characterized by analytical LC/MS ([M+H]$^+$ and retention time given in the following table).

| Example | Precursor | Amine | Compound | Retention time (minutes) | Mass [M + H]+ |
|---|---|---|---|---|---|
| 82-a | 80-a | | 4-(4-methyl-piperazin-1-yl)-benzene sulfonic acid 2-[3-(2-morpholin-4-yl-ethyl)-ureido]-3H-benzimidazol-5-yl ester | 5.12 | 544 |
| 82-b | 80-a | | 4-(4-methyl-piperazin-1-yl)-benzene sulfonic acid 2-(3-pyridin-2-ylmethyl-ureido)-3H-benzimidazol-5-yl ester | 4.46 | 522 |
| 82-c | 80-a | | 4-(4-methyl-piperazin-1-yl)-benzene sulfonic acid 2-[3-(2-methoxy-ethyl)-ureido]-3H-benzimidazol-5-yl ester | 5.86 | 489 |
| 82-d | 79 | | 4-(4-hydroxy-piperidin-1-yl)-benzene sulfonic acid 2-[3-(2-morpholin-4-yl-ethyl)-ureido]-3H-benzimidazol-5-yl ester | 5.47 | 545 |
| 82-e | 79 | | 4-(4-hydroxy-piperidin-1-yl)-benzene sulfonic acid 2-(3-pyridin-2-ylmethyl-ureido)-3H-benzimidazol-5-yl ester | 6.4 | 523 |
| 82-f | 79 | | 4-(4-hydroxy-piperidin-1-yl)-benzene sulfonic acid 2-[3-(2-methoxy-ethyl)-ureido]-3H-benzimidazol-5-yl ester | 7.06 | 490 |
| 82-g | 79 | | 4-(4-hydroxy-piperidin-1-yl)-benzene sulfonic acid 2-(3-ethyl-ureido)-3H-benzimidazol-5-yl ester | 3.3 | 460 |
| 82-h | 80-n | | 4-[(Pyridin-2-ylmethyl)-amino]-benzene sulfonic acid 2-[3-(2-morpholin-4-yl-ethyl)-ureido]-3H-benzimidazol-5-yl ester | 4.83 | 552 |
| 82-i | 80-n | | 4-[(Pyridin-2-ylmethyl)-amino]-benzene sulfonic acid 2-(3-pyridin-2-ylmethyl-ureido)-3H-benzimidazol-5-yl ester | 5.53 | 530 |

-continued

| Example | Precursor | Amine | Compound | Retention time (minutes) | Mass [M + H]+ |
|---|---|---|---|---|---|
| 82-j | 80-n | 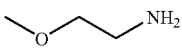 | 4-[(Pyridin-2-ylmethyl)-amino]-benzene sulfonic acid 2-[3-(2-methoxy-ethyl)-ureido]-3H-benzimidazol-5-yl ester | 6.6 | 497 |
| 82-k | 80-n |  | 4-[(Pyridin-2-ylmethyl)-amino]-benzene sulfonic acid 2-[3-(2-methoxy-ethyl)-ureido]-3H-benzimidazol-5-yl ester | 6.2 | 467 |
| 82-l | 80-i | 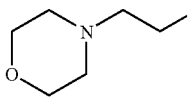 | 4-(3-Hydroxy-propylamino)-benzenesulfonic acid 2-[3-(2-morpholin-4-yl-ethyl)-ureido]-3H-benzimidazol-5-yl ester | 6.2 | 497 |
| 82-m | 80-i | 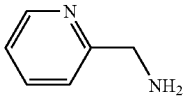 | 4-(3-Hydroxy-propylamino)-benzenesulfonic acid 2-(3-pyridin-2-ylmethyl-ureido)-3H-benzimidazol-5-yl ester | 5.48 | 519 |
| 82-n | 80-i | 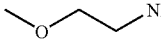 | 4-(3-Hydroxy-propylamino)-benzenesulfonic acid 2-[3-(2-methoxy-ethyl)-ureido]-3H-benzimidazol-5-yl ester | 6.84 | 464 |
| 82-o | 80-i |  | 4-(3-Hydroxy-propylamino)-benzenesulfonic acid 2-(3-ethyl-ureido)-3H-benzimidazol-5-yl ester | | |
| 82-p | 80-j | 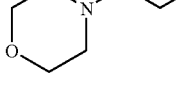 | 4-(2,2,6,6-tetramethyl-piperidin-4-ylamino)-benzenesulfonic acid 2-[3-(2-morpholin-4-yl-ethyl)-ureido]-3H-benzimidazol-5-yl ester | 0.41 | 600 |
| 82-q | 80-j | 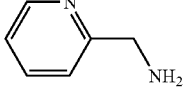 | 4-(2,2,6,6-tetramethyl-pipendin-4-ylamino)-benzenesulfonic acid 2-(3-pyridin-2-ylmethyl-ureido)-3H-benzimidazol-5-yl ester | 0.42 | 576 |
| 82-r | 80-k | 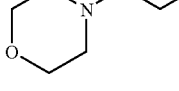 | 4-(2-dimethylamino-ethylamino)-benzenesulfonic acid 2-[3-(2-morpholin-4-yl-ethyl)-ureido]-3H-benzimidazol-5-yl ester | 0.41 | 532 |
| 82-s | 80-k | 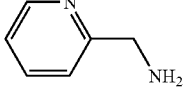 | 4-(2-dimethylamino-ethylamino)-benzenesulfonic acid 2-(3-pyridin-2-ylmethyl-ureido)-3H-benzimidazol-5-yl ester | 0.41 | 510 |
| 82-t | 80-l | 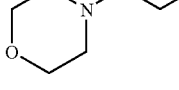 | 4-morpholin-4-yl-benzenesulfonic acid 2-[3-(2-morpholin-4-yl-ethyl)-ureido]-3H-benzimidazol-5-yl ester | 0.4 | 531 |
| 82-u | 80-l | 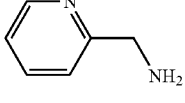 | 4-morpholin-4-yl-benzenesulfonic acid 2-(3-pyridin-2-ylmethyl-ureido)-3H-benzimidazol-5-yl ester | 2.9 | 509 |
| 82-v | 80-f | 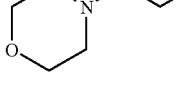 | 4-[3-(2-oxo-pyrrolidin-1-yl)-propylamino]-benzenesulfonic acid 2-[3-(2-morpholin-4-yl-ethyl)-ureido]-3H-benzimidazol-5-yl ester | 2.6 | 586 |

-continued

| Example | Precursor | Amine | Compound | Retention time (minutes) | Mass [M + H]+ |
|---|---|---|---|---|---|
| 82-w | 80-f | pyridin-2-ylmethylamine | 4-[3-(2-oxo-pyrrolidin-1-yl)-propylamino]-benzenesulfonic acid 2-(3-pyridin-2-ylmethyl-ureido)-3H-benzimidazol-5-yl ester | 2.46 | 485 |
| 82-x | 80-g | 2-methoxyethylamine | 4-(4-fluoro-benzylamino)-benzenesulfonic acid 2-(3-ethyl-ureido)-3H-benzimidazol-5-yl ester | 9.29 | 514 |
| 82-y | 80-h | 2-morpholin-4-yl-ethylamine | 4-(2-Hydroxy-2-methyl-propylamino)-benzenesulfonic acid 2-[3-(2-morpholin-4-yl-ethyl)-ureido]-3H-benzimidazol-5-yl ester | 6.61 | 511 |
| 82-z | 80-h | pyridin-2-ylmethylamine | 4-(2-Hydroxy-2-methyl-propylamino)-benzenesulfonic acid 2-(3-pyridin-2-ylmethyl-ureido)-3H-benzimidazol-5-yl ester | 6.29 | 533 |
| 82-aa | 80-h | 2-methoxyethylamine | 4-(2-Hydroxy-2-methyl-propylamino)-benzenesulfonic acid 2-[3-(2-methoxy-ethyl)-ureido]-3H-benzimidazol-5-yl ester | 2.89 | 478 |
| 82-ab | 80-h | 3-methoxypropylamine | 4-(2-Hydroxy-2-methyl-propylamino)-benzenesulfonic acid-2-[3-(3-hydroxy-propyl)-ureido]-3H-benzimidazol-5-yl ester | 7.33 | 478 |
| 82-ac | 80-b | 2-morpholin-4-yl-ethylamine | 4-[(Tetrahydro-pyran-4-ylmethyl)-amino]-benzenesulfonic acid 2-[3-(2-morpholin-4-yl-ethyl)-ureido]-3H-benzimidazol-5-yl ester | 7.28 | 537 |
| 82-ad | 80-b | pyridin-2-ylmethylamine | 4-[(Tetrahydro-pyran-4-ylmethyl)-amino]-benzenesulfonic acid 2-(3-pyridin-2-ylmethyl-ureido)-3H-benzimidazol-5-yl ester | 6.88 | 559 |
| 82-ae | 80-b | 2-methoxyethylamine | 4-[(Tetrahydro-pyran-4-ylmethyl)-amino]-benzenesulfonic acid 2-[3-(2-methoxy-ethyl)-ureido]-3H-benzimidazol-5-yl ester | 8.67 | 504 |
| 82-af | 80-b | 3-hydroxypropylamine | 4-[(Tetrahydro-pyran-4-ylmethyl)-amino]-benzenesulfonic acid 2-[3-(3-hydroxy-propyl)-ureido]-3H-benzimidazol-5-yl ester | 8.03 | 504 |
| 82-ag | 80-c | 2-morpholin-4-yl-ethylamine | 4-(2-fluoro-ethylamino)-benzenesulfonic acid 2-[3-(2-morpholin-4-yl-ethyl)-ureido]-3H-benzimidazol-5-yl ester | 2.5 | 507 |
| 82-ah | 80-c | pyridin-2-ylmethylamine | 4-(2-fluoro-ethylamino)-benzenesulfonic acid 2-(3-pyridin-2-ylmethyl-ureido)-3H-benzimidazol-5-yl ester | 2.46 | 485 |
| 82-ai | 80-d | 2-morpholin-4-yl-ethylamine | 4-(2-Piperidin-1-yl-ethylamino)-benzenesulfonic acid 2-[3-(2-morpholin-4-yl-ethyl)-ureido]-3H-benzimidazol-5-yl ester | 5.47 | 550 |

-continued

| Example | Precursor | Amine | Compound | Retention time (minutes) | Mass [M + H]+ |
|---|---|---|---|---|---|
| 82-aj | 80-d | (pyridin-2-ylmethylamine) | 4-(2-Piperidin-1-yl-ethylamino)-benzenesulfonic acid 2-(3-pyridin-2-ylmethyl-ureido)-3H-benzimidazol-5-yl ester | 4.25 | 572 |
| 82-ak | 80-e | 2-morpholin-4-yl-ethylamine | 4-phenethylamino-benzenesulfonic acid 2-[3-(2-morpholin-4-yl-ethyl)-ureido]-3H-benzimidazol-5-yl ester | 3.14 | 565 |
| 82-al | 80-e | 2-methoxy-ethylamine | 4-phenethylamino-benzenesulfonic acid 2-[3-(2-methoxy-ethyl)-ureido]-3H-benzimidazol-5-yl ester | 3.78 | 510 |
| 82-am | 80-e | ethylamine | 4-phenethylamino-benzenesulfonic acid 2-(3-ethyl-ureido)-3H-benzimidazol-5-yl ester | 3.83 | 480 |
| 82-an | 80-e | 3-hydroxy-propylamine | 4-phenethylamino-benzenesulfonic acid 2-[3-(3-hydroxy-propyl)-ureido]-3H-benzimidazol-5-yl ester | 3.57 | 510 |
| 82-ao | 80-o | 2-morpholin-4-yl-ethylamine | 4-(2-hydroxy-propylamino)-benzenesulfonic acid 2-[3-(2-morpholin-4-yl-ethyl)-ureido]-3H-benzimidazol-5-yl ester | 2.36 | 519 |
| 82-ap | 80-o | ethylamine | 4-(2-hydroxy-propylamino)-benzenesulfonic acid 2-(3-ethyl-ureido)-3H-benzimidazol-5-yl ester | 2.91 | 434 |
| 82-aq | 80-p | 2-morpholin-4-yl-ethylamine | 4-(4-methoxy-benzylamino)-benzenesulfonic acid 2-[3-(2-morpholin-4-yl-ethyl)-ureido]-3H-benzimidazol-5-yl ester | 3.03 | 581 |
| 82-ar | 80-p | ethylamine | 4-(4-methoxy-benzylamino)-benzenesulfonic acid 2-(3-ethyl-ureido)-3H-benzimidazol-5-yl ester | 3.67 | 496 |
| 82-as | 80-p | pyridin-2-ylmethylamine | 4-(4-methoxy-benzylamino)-benzenesulfonic acid 2-(3-pyridin-2-ylmethyl-ureido)-3H-benzimidazol-5-yl ester | 3.41 | 559 |
| 82-at | 80-p | 3-hydroxy-propylamine | 4-(4-methoxy-benzylamino)-benzenesulfonic acid 2-[3-(3-hydroxy-propyl)-ureido]-3H-benzimidazol-5-yl ester | 3.41 | 526 |
| 82-au | 80-p | 2-methoxy-ethylamine | 4-(4-methoxy-benzylamino)-benzenesulfonic acid 2-[3-(2-methoxy-ethyl)-ureido]-3H-benzimidazol-5-yl ester | 3.61 | 526 |
| 82-av | 80-q | ethylamine | 4-(2-pyrrolidin-1-yl-ethylamino)-benzenesulfonic acid 2-(3-ethyl-ureido)-3H-benzimidazol-5-yl ester | 2.26 | 473 |
| 82-aw | 80-q | pyridin-2-ylmethylamine | 4-(2-pyrrolidin-1-yl-ethylamino)-benzenesulfonic acid 2-(3-pyridin-2-ylmethyl-ureido)-3H-benzimidazol-5-yl ester | 2.08 | 536 |

-continued

| Example | Precursor | Amine | Compound | Retention time (minutes) | Mass [M + H]+ |
|---|---|---|---|---|---|
| 82-ax | 80-q | ![structure] | 4-(2-pyrrolidin-1-yl-ethylamino)-benzenesulfonic acid 2-[3-(2-methoxy-ethyl)-ureido]-3H-benzimidazol-5-yl ester | 2.25 | 503 |
| 82-ay | 80-r | ![structure] | 4-(1-phenyl-ethylamino)-benzenesulfonic acid 2-(3-ethyl-ureido)-3H-benzimidazol-5-yl ester | 3.76 | 480 |
| 82-az | 80-s | ![structure] | 4-(2-diethylamino-ethylamino)-benzenesulfonic acid 2-(3-pyridin-2-ylmethyl-ureido)-3H-benzimidazol-5-yl ester | 3.5 | 543 |

Example 83

Preparation of 1-(6-hydroxy-1H-benzoimidazol-2-yl)-3-(2-methoxy-ethyl)-urea

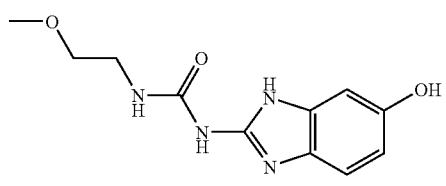

A solution of (6-hydroxy-1H-benzoimidazol-2-yl)-carbamic acid methyl ester (300 mg, example 61) and 2-methoxy-ethylamine (630 IA) in N-methylpyrrolidinone (8 ml) was heated at 90° C. in a sealed tube for 20 hours. The reaction mixture was poured into water (160 ml) and extracted three times with ethyl acetate (40 ml). The combined extracts were dried over magnesium sulfate and then evaporated. The residue was subjected to flash chromatography on silica eluting with a mixture of dichloromethane and methanol (95 C:5 C, v/v) to 1-(6-hydroxy-1H-benzoimidazol-2-yl)-3-(2-methoxy-ethyl)-urea as a yellow solid (180 mg). Mass spectrum: 251 [M+H]$^+$; retention time=0.55 minutes.

Example 84(a)

Preparation of 1-(6-hydroxy-1H-benzoimidazol-2-yl)-3-pyridin-2-ylmethyl-urea

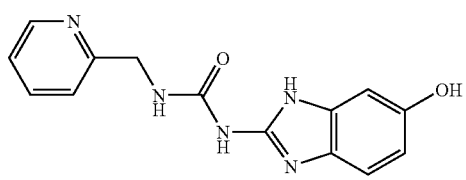

By proceeding in a manner similar to example 83 above but using 2-(aminomethyl)-pyridine there was prepared 1-(6-hydroxy-1H-benzoimidazol-2-yl)-3pyridin-2-ylm-ethyl-urea as a beige solid. Mass spectrum: 284 [M+H]$^+$; retention time=0.55 minutes.

Example 84(b)

Preparation of 1-(6-hydroxy-1H-benzoimidazol-2-yl)-3-(2-morpholin-4-yl-ethyl)-urea

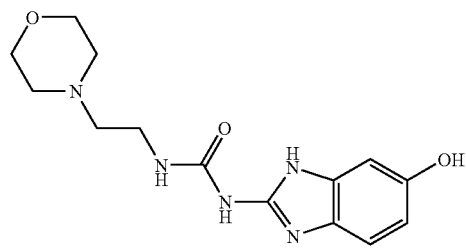

By proceeding in a manner similar to example 83 above but using 2-(aminoethyl)-morpholine there was prepared 1-(6-hydroxy-1H-benzoimidazol-2-yl)-3-(2-morpholin-4-yl-ethyl)-urea as a beige solid. Mass spectrum: 306 [M+H]$^+$; retention time=1.02 minute.

Example 84(c)

Preparation of 1-(6-hydroxy-1H-benzoimidazol-2-yl)-3-(ethyl)-urea

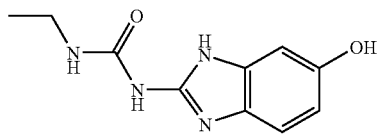

By proceeding in a manner similar to example 83 above but using ethylamine there was prepared 1-(6-hydroxy-1H-benzoimidazol-2-yl)-3-(ethyl)-urea as a beige solid. Mass spectrum: 367 [M+H]$^+$; retention time=1.36 minute.

Example 85

Preparation of thiophene-2-sulfonic acid 2-[3-(2-ethyl)-ureido]-1H-benzoimidazol-5-yl ester

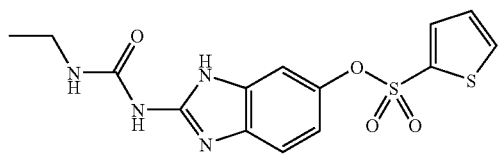

A stirred solution of 1-ethyl-3-(6-hydroxy-1H-benzoimidazol-2-yl)-urea (35 mg, example 84-c) and thiophene-2-sulfonyl chloride (18 mg) in acetone (3 ml) was treated with triethylamine (25 µl). After stirring at ambient temperature for 4 hours, the reaction mixture was evaporated. The residue was filtered and the filtrate evaporated. The residue was directly purified by LCMS triggered purification to give thiophene-2-sulfonic acid 2-[3-(2-ethyl)-ureido]-1H-benzoimidazol-5-yl ester (14 mg) as a off-white solid Mass spectrum: 367 [M+H]$^+$; retention time=7.88 minutes.

Example 86

By using a method similar to that for the preparation of example 85, combining thiophene-2-sulfonyl chloride with suitable 1-(6-hydroxy-1H-benzoimidazol-2-yl)-urea (example 83, 84) were obtained the following compounds that were characterized by analytical LC/MS ([M+H]$^+$ and retention time given in the following table).

Example 87

Preparation of benzoic acid 4-{2-[3-(2-methoxy-ethyl)-ureido]-1H-benzoimidazol-5-yloxysulfonyl}-phenyl ester

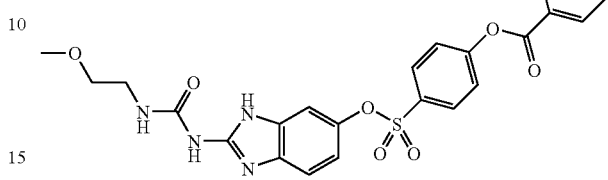

A stirred solution of 1-(6-hydroxy-1H-benzoimidazol-2-yl)-3-(2-methoxy-ethyl)-urea (31 mg, example 82) and benzoic acid 4-chlorosulfonyl-phenyl ester (37 mg) in acetone (0.6 ml) was treated with triethylamine (33 µl). After stirring at ambient temperature for 4 hours, the reaction mixture was evaporated. The residue was filtered and the filtrate evaporated. The residue was directly purified by LCMS triggered purification to give benzoic acid 4-{2-[3-(2-methoxy-ethyl)-ureido]-1H-benzoimidazol-5-yloxysulfonyl}-phenyl ester (7.2 mg) as a off-white solid Mass spectrum: 511 [M+H]$^+$; retention time=9.90 minutes.

Example 88

By using a method similar to that for the preparation of example 87, combining benzoic acid 4-chlorosulfonyl-phenyl ester with suitable 1-(6-hydroxy-1H-benzoimidazol-2-yl)-urea (example 83, 84) were obtained the following compounds that were characterized by analytical LC/MS ([M+H]$^+$ and retention time given in the following table).

| Example | 1-(6-hydroxy-1H-benzoimidazol-2-yl)-urea | Compound | Retention time (minutes) | Masse [M + H]+ |
|---|---|---|---|---|
| 86-a | | Thiophene-2-sulfonic acid 2-[3-(2-methoxy-ethyl)-ureido]-1H-benzoimidazol-5-yl ester | 2.99 | 397 |
| 86-b | | Thiophene-2-sulfonic acid 2-[3-(2-morpholin-4-yl-ethyl)-ureido]-1H-benzoimidazol-5-yl ester | 2.8 | 452 |
| 86-c | | Thiophene-2-sulfonic acid 2-(3-pyridin-2-ylmethyl)-ureido]-1H-benzoimidazol-5-yl ester | 6.52 | 430 |

| Example | 1-(6-hydroxy-1H-benzoimidazol-2-yl)-urea | Compound | Retention time (minutes) | Masse [M + H]+ |
|---|---|---|---|---|
| 88-a | 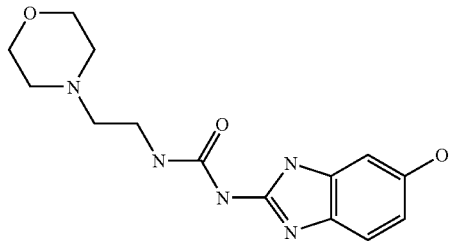 | Benzoic acid 4-{2-[3-(2-morpholin-4-yl-ethyl)-ureido}-1H-benzoimidazol-5-yl-oxysulfonyl}-phenyl ester | 7.44 | 566 |
| 88-b | 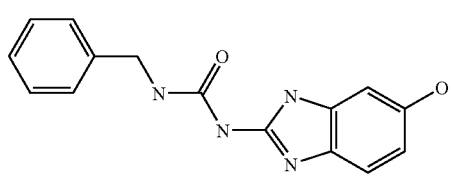 | Benzoic acid 4-[2-([3-pyridin-2-ylmethyl)-ureido)-1H-benzoimidazol-5-yl-oxysulfonyl]-phenyl ester | 8.91 | 544 |

Example 89(a)

Preparation of 2,6-difluoro-benzenesulfonic acid 2-(3-pyridin-2-ylmethyl-ureido)-3H-benzoimidazol-5-yl ester

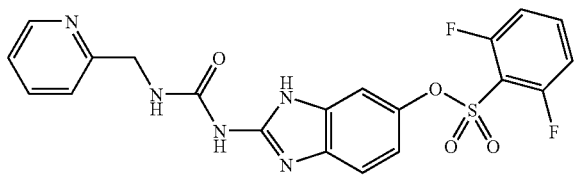

A stirred solution of 1-(6-hydroxy-1H-benzoimidazol-2-yl)-3-pyridin-2-ylmethyl-urea (50 mg, example 83-a) and 2,6-difluoro-benzene-sulfonyl chloride (38 mg) in acetone (1 ml) was treated with triethylamine (48 µl). After stirring at ambient temperature for 4 hours, the reaction mixture was evaporated. The residue was filtered and the filtrate evaporated. The residue was directly purified by LC/MS triggered purification to give benzoic acid 2,6-difluoro-benzene-sulfonic acid 2-(3-pyridin-2-ylmethyl-ureido)-3H-benzoimidazol-5-yl ester (29.6 mg) as a off-white solid Mass spectrum: 427 [M+H]$^+$; retention time=7.86 minutes.

Example 89(b)

Preparation of 2,6-difluoro-benzenesulfonic acid 2-[3-(2-methoxy-ethyl)-ureido]-3H-benzoimidazol-5-yl ester By proceeding in a manner similar to example 89(a) above but using 1-(6-hydroxy-1H-benzoimidazol-2-yl)-3-(2-methoxy-ethyl)-urea there was prepared 2,6-difluoro-benzenesulfonic acid 2-[3-(2-methoxy-ethyl)-ureido]-3H-benzoimidazol-5-yl ester as an off-white solid. Mass spectrum: 427 [M+H]$^+$; retention time=7.86 minutes.

Biological Tests

The experiments described in this report were designed to evaluate the cytotoxicity of "in vitro" Cdk4 inhibitors in comparison with Staurosporine, a non-specific Serine-Threonine kinase inhibitor.

Stock solutions of compounds were made in DMSO at 10 mM and stored at −20° C. Subsequent dilutions were made in 28% DMSO and used to add 3 µl of the drugs at varied concentrations to the HeLa cells.

All cell lines were cultured at 37° C. in a humidified atmosphere containing 5% $CO_2$.

HeLa human epithelial cell line was obtained from the American Type Culture Collection (Rockville, Md., USA). Cells were grown as monolayers in Dubelcco's Modified Eagle Medium containing 2 mM L-glutamine, 200 I.U./ml penicillin, 200 µg/ml streptomycin, and supplemented with 10% (v/v) heat inactivated foetal calf serum. Cells were transferred twice a week at 10$^5$ cells/ml in 75 cm$^2$ flasks after trypsinisation. Different flasks were done to prepare two preparations the day of experiment.

Cell Growth Inhibition

Cells in exponential phase of growth were trypsinised and resuspended in their culture medium at 2.5 10$^4$ cells/ml, in two independent preparations. Cell suspension was distributed in 96 well Cytostar microplates (Amersham) (0.2 ml/well, 5000 cells). Hela cells were coated for 4 hours at 37° C. [$^{14}$C]-thymidine (0.1 µCi/well) and ten final concentrations of molecules (3 µl) ranging from 20 to 0.03 µM were then added. The uptake of [$^{14}$C]-thymidine was measured 48 h after the labelling had been started using a Microbeta Trilux counter (Wallac).

Staurosporine, the reference compound, was evaluated using the same procedure.

CPM measured 48 hours after the test substance had been added to the media, were compared to those obtained with 0.4% final DMSO, in the control wells.

IC$_{50}$, obtained from a dose response curve of 10 concentrations in duplicate is the concentration of drug wich diminishes half the specific signal. It is determined by non-linear regression analysis and calculated as a concentration at middle of curve.

IC$_{50}$ values result from 2 independent experiments for all tested molecules.

CDK4/CyclinD1 Flashplate Assay: 96-well Format

This is a CDK4/CyclinD1 kinase assay in a 96-well Streptavidin-coated Flashplate with a biotinylated-Rb peptide substrate.

Each point is tested in duplicate

Biotinylated-Rb: Biotin-RPPTLSPIPHIPRSPYKFPSS-PLR

| Kinase Buffer: | |
|---|---|
| HEPES, pH 8 | 50 mM |
| MgCl$_2$ 6H$_2$O, pH 7 | 10 mM |
| DTT | 1 mM |

1. Prepare substrate: 1 mg/ml solution made fresh in PBS.
2. Add 100 µg per well to the Flashplate.
3. Incubate for 2 hours at RT.
4. From 10 mM inhibitor stocks in DMSO, make 1 mM, 300 µM, 100 µM, 30 µM and 10 µM series of dilution in DMSO.
5. Wash the Flashplate 3 times with 300 µl PBS to remove unbound peptide substrate.
6. Add the CDK4/CyclinD1 kinase: 70 ng per well, in a volume of 90 µl in kinase buffer (except for "no enzyme" control wells).
7. Add 1 µl[1] per well of inhibitor to test 10 µM, 3 µM, 1 µM, 0.3 µM and 0.1 µM in final concentration per 100 µl in each well.
8. Shake gently the Flashplate 1 minute.
9. Incubate 30 minutes on wet ice.
10. Initiate the reaction with 10 µl kinase buffer containing 1 µM final cold ATP and 1 µCi final $^{33}$P-ATP per well.
11. Shake gently the Flashplate 1 minute.
12. Incubate 45 minutes at RT (no shaking).
13. Wash the Flashplate 3 times with 300 µl PBS
14. Count to detect the incorporation of $^{33}$P-ATP by the kinase to the Rb phosphorylation site.

CDK2/CyclinE Flashplate Assay: 96-well Format

This is a CDK2/CyclinE kinase assay in a 96-well Streptavidin-coated Flashplate with a biotinylated-Rb peptide substrate.

Each Point is Tested in Duplicate

Biotinylated-Rb: Biotin-SACPLNLPLQNNHTAAD-MYLSPVRSPKKKGSTTR-OH

| Kinase Buffer: | |
|---|---|
| HEPES, pH 8.0 | 50 mM |
| MgCl$_2$ 6H$_2$O | 10 mM |
| DTT | 1 mM |

1. Prepare substrate: 1 mg/ml solution made fresh in PBS.
2. Add 4 µg per well to the Flashplate.
3. Incubate for 2 hours at RT.
4. From 10 mM inhibitor stocks in DMSO, make 1 mM, 300 µM, 100 µM, 30 µM and 10 µM series of dilution in DMSO.
5. Was the Flashplate 3 times with 300 µl PBS to remove unbound peptide substrate.
6. Add the CDK2/CyclinE kinase: 200 ng per well, in a volume of 90 µl in kinase buffer (except for "no enzyme" control wells).
7. Add 1 µl per well of inhibitor to test 10 µM, 3 µM, 1 µM, 0.3 µM and 0.1 µM in final concentration per 100 µl in each well.
8. Shake gently the Flashplate 1 minute.
9. Incubate 30 minutes on wet ice.
10. Initiate the reaction with 10 µl kinase buffer containing 1 µM final cold ATP and 1 µCi final $^{33}$P-ATP per well.
11. Shake gently the Flashplate 1 minute.
12. Incubate 45 minutes at RT (no shaking).
13. Wash the Flashplate 3 times with 300 µl PBS
14. Count to detect the incorporation of $^{33}$P-ATP by the kinase to the Rb phosphorylation site.

| Example N° | IC50 CDK4/cyclinD1 (µM) | IC50 CDK2/cyclinE (µM) |
|---|---|---|
| 1 | 1.5 | 0.6 |
| 2 | 2 | 0.7 |
| 3 | 2.4 | 0.5 |
| 4 | 6.3 | 1.5 |
| 5 | 1.12 | 2.2 |
| 6 | 0.84 | 0.3 |
| 7 | 0.47 | 2 |
| 8 | 1.1 | Nd |
| 9 | 2 | Nd |
| 10 | 0.7 | 0.8 |
| 11 | 0.93 | 0.5 |
| 12 | 14% inhibition at 10 µM | Nd |
| 13 | 0.4 | 2 |
| 14 | 0.3 | 0.2 |
| 15 | 0.3 | 1.8 |
| 16 | 0.37 | 1.8 |
| 17 | 6.3 | 2 |
| 18 | 1.3 | 0.6 |
| 19 | 2.92 | 0.7 |
| 20 | >3 | >10 |
| 22 | 1.77 | Nd |
| 23 | 3.1 | 0.4 |
| 24 | 0.6 | 0.4 |
| 25 | 0.13 | 0.08 |
| 26 | 0.68 | 0.13 |
| 27 | 0.6 | 0.042 |
| 28 | 1.03 | 0.6 |
| 29 | 1.7 | 0.6 |
| 30 | 1.8 | 0.9 |
| 31 | 0.5 | 0.1 |
| 32 | >5 | 1.1 |
| 33 | 0.64 | 0.06 |
| 34 | 1.18 | 0.12 |
| 35 | 1.1 | 0.12 |
| 36 | 0.77 | 0.53 |
| 37 | 0.57 | 0.45 |
| 38 | 1.25 | 4.3 |
| 39 | 1.62 | 0.29 |
| 40 | 3.71 | 1.09 |
| 41 | 2.8 | 0.06 |
| 42 | 84% inhibition at 10 µM | 0.91 |
| 43 | 1.9 | 0.2 |
| 44 | 0.6 | 0.13 |
| 45 | 0.6 | 0.06 |
| 46 | 0.012 | 0.06 |
| 47 | 0.8 | 0.16 |
| 48 | 0.3 | 0.04 |
| 49 | 88% inhibition at 10 µM | 0.4 |
| 50 | 0.3 | 0.04 |
| 51 | 0.8 | 0.14 |
| 52 | 1 | 0.08 |

-continued

| Example N° | IC50 CDK4/cyclinD1 (μM) | IC50 CDK2/cyclinE (μM) |
|---|---|---|
| 53 | 83% inhibition at 10 μM | 0.8 |
| 54 | 0.5 | 0.005 |
| 57-a | 1 | 0.24 |
| 57-b | 51% inhibition at 10 μM | 1.9 |
| 57-c | 60% inhibition at 10 μM | 0.6 |
| 57-d | 70% inhibition at 10 μM | 0.5 |
| 57-e | 90% inhibition at 10 μM | 0.3 |
| 57-f | 88% inhibition at 10 μM | 0.5 |
| 57-g | 52% inhibition at 10 μM | 0.6 |
| 57-h | 4.4 | 0.1 |
| 57-i | 27% inhibition at 10 μM | 5.2 |
| 57-j | 3 | 0.1 |
| 57-k | 49% inhibition at 10 μM | 0.6 |
| 57-l | 1 | 0.07 |
| 58-a | 96% inhibition at 10 μM | 0.38 |
| 58-b | 70% inhibition at 10 μM | 0.9 |
| 58-c | 60% inhibition at 10 μM | 0.6 |
| 58-d | 84% inhibition at 10 μM | 1.6 |
| 58-e | 0.1 | 0.04 |
| 58-f | 91% inhibition at 10 μM | 0.7 |
| 58-g | 69% inhibition at 10 μM | 1 |
| 58-h | 3 | 0.1 |
| 58-i | 81% inhibition at 10 μM | 0.3 |
| 58-j | 0.5 | 0.009 |
| 58-k | 0.5 | 0.04 |
| 58-l | 1 | 0.03 |
| 58-m | 0.24 | 0.03 |
| 58-n | 0.6 | Nd |
| 58-o | 0.029 | 0.02 |
| 58-p | 0.6 | Nd |
| 58-q | 1 | Nd |
| 58-r | 80% inhibition at 10 μM | Nd |
| 58-s | 0.012 | 0.02 |
| 58-t | 9 | Nd |
| 58-u | 0.29 | 0.01 |
| 58-v | 0.11 | 0.1 |
| 58-w | 0.19 | 0.25 |
| 58-x | 0.31 | 0.04 |
| 58-y | 0.27 | 0.01 |
| 58-z | 2.23 | Nd |
| 58-aa | 0.34 | 0.1 |
| 58-ab | 0.22 | 0.002 |
| 58-ac | 0.17 | 0.013 |
| 58-ad | 0.13 | 0.016 |
| 58-ae | 1.49 | Nd |
| 58-af | 0.21 | 0.18 |
| 58-ag | 0.39 | 0.04 |
| 58-ah | 0.33 | 0.03 |
| 58-ai | 0.33 | 0.15 |
| 58-aj | 0.38 | 0.37 |
| 58-ak | 0.18 | 0.1 |
| 58-al | 0.25 | 0.15 |
| 58-am | 0.24 | 0.08 |
| 58-an | 0.2 | 0.1 |
| 59-a | 0.1 | 0.008 |
| 59-b | 0.3 | 0.007 |
| 59-c | 1 | 0.007 |
| 59-d | 0.5 | 0.015 |
| 59-e | 1.6 | 0.1 |
| 59-f | 1.8 | 0.06 |
| 59-g | 1.8 | 0.2 |
| 59-h | 1.1 | 0.2 |
| 59-i | 1.2 | 0.04 |
| 59-j | 0.9 | 0.007 |
| 59-k | 0.3 | 0.02 |
| 59-l | 0.3 | 0.004 |
| 59-m | 1.2 | 0.03 |
| 59-n | 0.13 | 0.036 |
| 59-o | 0.8 | 0.04 |
| 59-p | 0.18 | 0.017 |
| 59-q | 0.75 | 0.11 |
| 59-r | 1.8 | 0.22 |
| 60-a | 0.8 | Nd |
| 60-b | 0.15 | Nd |
| 60-c | 0.34 | Nd |
| 60-d | 0.9 | Nd |
| 60-e | 0.9 | Nd |
| 60-f | 1 | Nd |
| 60-g | 1.5 | Nd |
| 60-h | Nd | Nd |
| 60-i | 0.3 | Nd |
| 60-j | Nd | Nd |
| 60-k | Nd | Nd |
| 60-l | 0.4 | Nd |
| 60-m | 0.5 | Nd |
| 60-n | 2 | Nd |
| 60-o | 5 | Nd |
| 60-p | 1.2 | Nd |
| 60-q | 1.8 | Nd |
| 60-r | 0.6 | Nd |
| 60-s | 8 | Nd |
| 60-t | 2 | Nd |
| 60-u | Nd | Nd |
| 60-v | 4.2 | Nd |
| 60-w | 0.5 | Nd |
| 60-x | 5 | Nd |
| 60-y | 2.5 | Nd |
| 60-z | 3 | Nd |
| 60-aa | 3.9 | Nd |
| 60-ab | 4 | Nd |
| 60-ac | 0.8 | Nd |
| 60-ad | 1.3 | Nd |
| 60-ae | 2.2 | Nd |
| 60-af | Nd | Nd |
| 60-ag | Nd | Nd |
| 60-ah | 0.55 | Nd |
| 60-ai | 1.6 | Nd |
| 61 | 2.06 | Nd |
| 62-a | 50% inhibition at 10 μM | Nd |
| 62-b | 0.44 | 0.2 |
| 62-c | 3 | 0.8 |
| 62-d | 1.3 | Nd |
| 62-e | 4.6 | 1 |
| 62-f | 3 | 1.5 |
| 62-g | 3 | 1 |
| 62-h | 0.8 | 0.07 |
| 62-i | 1.5 | 1 |
| 62-j | 3 | 1.5 |
| 62-k | 3 | Nd |
| 62-l | 2.5 | Nd |
| 62-m | 1.2 | Nd |
| 62-n | 1 | Nd |
| 62-o | 1 | Nd |
| 62-p | 0.7 | Nd |
| 62-q | 1.6 | Nd |
| 62-r | 2.5 | Nd |
| 62-s | 1.75 | Nd |
| 63 | 1.5 | Nd |
| 64-a | 1 | Nd |
| 64-b | 50% at 10 μM | Nd |
| 64-c | 4.37 | Nd |
| 64-d | 50% at 10 μM | Nd |
| 64-e | Nd | Nd |
| 65 | Nd | 1 |
| 66-a | 19% inhibition at 10 μM | Nd |
| 66-b | 3.05 | Nd |
| 66-c | Nd | 1 |
| 67 | 91% inhibition at 10 μM | Nd |
| 68-a | 97% inhibition at 10 μM | Nd |
| 68-b | 78% inhibition at 10 μM | Nd |
| 69 | 0.84 | 0.13 |
| 70-a | 1.18 | Nd |
| 70-b | 0.67 | 3 |
| 70-c | 2 | 0.8 |
| 70-d | 0.65 | 0.3 |
| 70-e | 0.5 | 0.8 |
| 70-f | Nd | 5 |
| 70-g | 5 | 1.5 |
| 70-h | 0.14 | 0.25 |
| 78-e | 0.6 | Nd |
| 78-f | 0.1 | Nd |

-continued

| Example N° | IC50 CDK4/cyclinD1 (μM) | IC50 CDK2/cyclinE (μM) |
|---|---|---|
| 78-h | 90% inhibition at 10 μM | Nd |
| 78-i | 97% inhibition at 10 μM | Nd |
| 78-k | 78% inhibition at 10 μM | Nd |
| 78-l | 100% inhibition at 10 μM | Nd |
| 78-n | 54% inhibition at 10 μM | Nd |
| 78-o | 54% inhibition at 10 μM | Nd |
| 78-q | 94% inhibition at 10 μM | Nd |
| 78-s | 88% inhibition at 10 μM | Nd |
| 78-t | 55% inhibition at 10 μM | Nd |
| 78-u | 93% inhibition at 10 μM | Nd |
| 78-v | 46% inhibition at 10 μM | Nd |
| 78-w | 90% inhibition at 10 μM | Nd |
| 80-c | 100% inhibition at 10 μM | Nd |
| 80-m | 103% inhibition at 10 μM | Nd |
| 82-h | 92% inhibition at 10 μM | Nd |

What is claimed is:

1. A compound of formula (I)

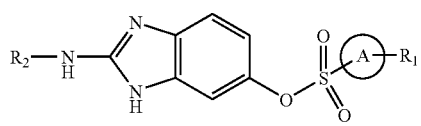

(I)

wherein

A is phenyl or napthyl;

$R_1$ is one or more groups selected from:

$NH_2$; NH-alkyl or NH-cycloalkyl optionally substituted by acyl, acyl derivative, hydroxy, amino, alkoxy, heterocyclyl chosen from substituted or unsubstituted tetrahydrofuranyl, tetrahydropyranyl, pyrrolidinyl, 2-oxo-pyrrolidinyl, piperidinyl, piperazinyl, morpholinyl or azepanyl, or aryl; or 1-imidazolyl;

$R_2$ is:

—CO-alkyl or —CO-cycloalkyl wherein said —CO-alkyl or —CO-cycloalkyl is optionally substituted by one or more amino, acyl, acyl derivative, alkoxy, aryl, OH, aminoalkyl, aminoalkylamino, hydroxyalkoxy, alkyl, arylalkyl, arylamino or aryloxy;

—CO-aralkyl optionally substituted by one or more similar or different groups selected from alkoxy, halogen, amino, acyl, acyl derivative, alkyl, hydroxyalkyl, mono or dialkylamino, arylamino, nitro, perfluoroalkyl, perfluroralkoxy, perfluoroalkylthio, or alkylthio optionally substituted by amino, acyl, acyl derivative, alkyl, arylalkyl or aryl;

—CO-aryl optionally substituted by one or more similar or different groups selected from halogen, alkoxy, alkyl, hydroxyalkyl, alkylthio, amino, mono or dialkylamino, heterocyclylamino, arylamino, nitro, perfluoroalkyl, perfluoroalkoxy, perfluoroalkylthio, or acyl;

—CO-alkoxy optionally substituted by aryl, amino, acyl, acyl derivative, alkyl, arylalkyl or aryl;

—CO-amino, —CO—$NHR_3$, —CO—$NR_3R_4$ wherein $R_3$ and $R_4$ are selected independently from hydrogen, alkyl, hydroxyalkyl, alkoxyalkyl, fluoroalkyl, alkynyl, heterocyclyl selected from pyrrolidinylalkyl, 2-oxo-pyrrolidinylalkyl, piperidinylalkyl, tetrahydropyranylalkyl or morpholinylalkyl, alkylheterocycloalkyl selected from 4-alkylpiperazinylalkyl or N-alkyl-pyrrolidinylalkyl, aryl, aralkyl, or together form an alkylene chain optionally containing one to 4 heteroatoms selected from azetidine, pyrrolidine or piperidine, and optionally substituted by one or more amino, aminoalkyl, aminoalkylamino, hydroxy, alkoxy, hydroxyalkoxy, hydroxyalkylamino, halogen, acyl, acyl derivative, alkyl, arylalkyl, arylamino, aryloxy or aryl; or aryl or aralkyl optionally substituted by one or more similar or different groups selected from heterocyclyl selected from morpholinyl or alkyl piperazinyl, alkyl, aryl, alkoxy, amino, fluoroalkyl, acyl derivative, halogen, hydroxyalkyl, mono or dialkylamino, arylamino, heteroaryl selected from oxadiazolyl, nitro, perfluoroalkyl, perfluroalkoxy, perfluoroalkylthio, or alkylthio optionally substituted by amino, acyl, acyl derivative, alkyl, arylalkyl or aryl;

wherein when A is phenyl and $R_1$ is $NH_2$, NH-alkyl, NH-cycloalkyl or 1-imidazolyl, said phenyl is substituted at the 4-position with said $R_1$; and when $R_2$ is —CO-alkoxy, $R_1$ is NH-cycloalkyl, or a pharmaceutically acceptable salt thereof.

2. The compound according to claim 1 wherein acyl is a carboxylic acid or a sulfonic acid and acyl derivative is an alkyl or carbamoyl ester.

3. A compound according to claim 2 wherein:

A is phenyl or napthyl;

$R_1$ is one or more groups selected from:

$NH_2$;

NH-alkyl or NH-cycloalkyl optionally substituted by acyl, acyl derivative, hydroxy, amino, alkoxy, heterocyclyl chosen from substituted or unsubstituted tetrahydrofuranyl, tetrahydropyranyl, pyrrolidinyl, 2-oxo-pyrrolidinyl, piperidinyl, piperazinyl, morpholinyl or azepanyl, or aryl; or b 1-imidazolyl;

$R_2$ is:

—CO-alkyl or —CO-cycloalkyl wherein said —CO-alkyl or —CO-cycloalkyl is optionally substituted by amino, acyl, acyl derivative, alkoxy, aryl or OH;

—CO-aralkyl optionally substituted by alkoxy, halogen, amino, acyl or acyl derivative;

—CO-aryl optionally substituted by halogen, alkoxy, alkyl, hydroxyalkyl, alkylthio, amino, mono or dialkylamino, nitro, perfluoroalkyl, perfluoroalkoxy, perfluoroalkylthio, or acyl;

—CO-alkoxy optionally substituted by aryl;

—CO-amino, —CO—$NHR_3$, —CO—$NR_3R_4$ wherein $R_3$ and $R_4$ are selected independently from hydrogen, alkyl, hydroxyalkyl, alkoxyalkyl, fluoroalkyl, alkynyl, heterocyclyl selected from pyrrolidinylalkyl, 2-oxo-pyrrolidinylalkyl, piperidinylalkyl, tetrahydropyranylalkyl or morpholinylalkyl, alkylheterocycloalkyl selected from 4-alkylpiperazinylalkyl or N-alkyl-pyrrolidinylalkyl, aryl, aralkyl or together form an alkylene chain optionally containing one to 4 heteroatoms selected from azetidine, pyrrolidine or piperidine; or aryl or aralkyl optionally substituted by heterocyclyl selected from morpholinyl or alkyl piperazinyl, alkyl, aryl, alkoxy, amino, fluroroalkyl, acyl derivative, or halogen.

4. The compound according to claim 3 wherein A is phenyl.

5. The compound according to claim 4 wherein $R_1$ is NH-cycloalkyl and $R_2$ is —CO-alkoxy.

6. The compound according to claim 5 wherein the compound is methyl-5-(4-cyclopentylaminophenylsulfonyloxy)benzimidazole-2-carbamate.

7. The compound according to claim 4 wherein $R_1$ is 1-imidazolyl or cyclopentylamino and $R_2$ is —CO-alkyl optionally substituted by amino, acyl, acyl derivative, alkoxy, aryl or OH.

8. The compound according to claim 7 wherein the compound is selected from the group consisting of:
  N-[5-(4-imidazol-1-yl-benzenesulfonyloxy)-1H-benzoimidazol-2-yl]-succinamic acid methyl ester,
  N-[5-(4-cyclopentylamino-benzenesulfonyloxy)-1H-benzoimidazol-2-yl]-succinamic acid methyl ester,
  4-[5-(4-cyclopentylamino-benzenesulfonyloxy)-1H-benzoimidazol-2-ylcarbabomyl]-butyric acid methyl ester, and
  4-cyclopentylamino-benzenesulfonic acid 2-(2-methoxy-acetylamino)-1H-benzoimidazol-5-yl ester.

9. The compound according to claim 4 wherein $R_1$ is 1-imidazolyl, or NH-alkyl or NH-cycloalkyl optionally substituted by acyl, acyl derivative, hydroxy, amino, alkoxy, heterocyclyl chosen from substituted or unsubstituted tetrahydrofuranyl, tetrahydropyranyl, pyrrolidinyl, 2-oxo-pyrrolidinyl, piperidinyl, piperazinyl, morpholinyl or azepanyl or aryl and $R_2$ is —CO-amino, —CO—$NHR_3$, —CO—$NR_3R_4$ wherein $R_3$ and $R_4$ are selected independently from hydrogen, alkyl, hydroxyalkyl, alkoxyalkyl, fluoroalkyl, alkynyl, heterocyclyl selected from pyrrolidinylalkyl, 2-oxo-pyrrolidinylalkyl, piperidinylalkyl, tetrahydropyranylalkyl or morpholinylalkyl, alkylheterocycloalkyl selected from 4-alkylpiperazinylalkyl or N-alkyl-pyrrolidinylalkyl, aryl, aralkyl or together form an alkylene chain optionally containing one to 4 heteroatoms selected from azetidine, pyrrolidine or piperidine.

10. The compound according to claim 9 selected from the group consisting of:
  N-[5-(4-[imidazolyl]-phenylsulfonyloxy)-1H-benzimidazole-2-yl]-methylurea,
  N-[5-(4-cyclopentylaminophenylsulfonyloxy)-1H-benzimidazole-2-yl]-methylurea,
  N-[5-(4-cyclopentylaminophenylsulfonyloxy)-1H-benzimidazole-2-yl]-dimethylurea,
  4-cyclopentylamino-benzenesulfonic acid 2-(3-isopropyl-ureido)-1H-benzoimidazol-5-yl ester,
  4-cyclopentylamino-benzenesulfonic acid 2-(3-butyl-ureido)-1H-benzoimidazol-5-yl ester,
  4-imidazol-1-yl-benzenesulfonic acid 2-[3-(2-fluoro-phenyl)-ureido]-1H-benzoimidazol-5-yl ester,
  4-cyclopentylamino-benzenesulfonic acid 2-[3-(2-fluoro-phenyl)-ureido]-1H-benzoimidazol-5-yl ester,
  4-cyclopentylamino-benzenesulfonic acid 2-[3-(3-methoxy-phenyl)-ureido]-1H-benzoimidazol-5-yl ester,
  4-cyclopentylamino-benzenesulfonic acid 2-[3-(4-methoxy-phenyl)-ureido]-1H-benzoimidazol-5-yl ester,
  4-cyclopentylamino-benzenesulfonic acid 2-[3-(4-chloro-phenyl)-ureido]-1H-benzoimidazol-5-yl ester,
  4-cyclopentylamino-benzenesulfonic acid 2-[3-(3-fluoro-benzyl)-ureido]-1H-benzoimidazol-5-yl ester,
  4-cyclopentylamino-benzenesulfonic acid 2-[3-(3-chloro-phenyl)-ureido]-1H-benzoimidazol-5-yl ester,
  4-cyclopentylamino-benzenesulfonic acid 2-(3-isobutyl-ureido)-1H-benzoimidazol-5-yl ester,
  4-cyclopentylamino-benzenesulfonic acid 2-[3-(2-dimethylamino-ethyl)-ureido]-1H-benzoimidazol-5-yl ester,
  4-cyclopentylamino-benzenesulfonic acid 2-(3-ethyl-ureido)-1H-benzoimidazol-5-yl ester,
  4-cyclopentylamino-benzenesulfonic acid 2-[3-(2-methoxy-ethyl)-ureido]-1H-benzoimidazol-5-yl ester,
  4-cyclopentylamino-benzenesulfonic acid 2-[3-(4-dimethylamino-phenyl)-ureido]-1H-benzoimidazol-5-yl ester,
  4-cyclopentylamino-benzenesulfonic acid 2-(3-tert-butyl-ureido)-1H-benzoimidazol-5-yl ester,
  4-[(tetrahydro-furan-2-ylmethyl)-amino]-benzenesulfonic acid 2-(3-methyl-ureido)-1H-benzoimidazol-5-yl ester,
  4-imidazol-1-yl-benzenesulfonic acid 2-(3-phenyl-ureido)-1H-benzoimidazol-5-yl ester,
  4-imidazol-1-yl-benzenesulfonic acid 2-[3-(3-fluoro-phenyl)-ureido]-1H-benzoimidazol-5-yl ester,
  4-imidazol-1-yl-benzenesulfonic acid 2-[3-(2-hydroxy-ethyl)-ureido]-1H-benzoimidazol-5-yl ester,
  4-imidazol-1-yl-benzenesulfonic acid 2-[3-(4-fluoro-phenyl)-ureido]-1H-benzoimidazol-5-yl ester,
  4-imidazol-1-yl-benzenesulfonic acid 2-[3-(2-chloro-benzyl)-ureido]-1H-benzoimidazol-5-yl ester,
  4-imidazol-1-yl-benzenesulfonic acid 2-[3-(2-fluoro-benzyl)-ureido]-1H-benzoimidazol-5-yl ester,
  4-imidazol-1-yl-benzenesulfonic acid 2-[(azetidine-1-carbonyl)-amino]-1H-benzoimidazol-5-yl ester,
  4-imidazol-1-yl-benzenesulfonic acid 2-(3-benzyl-ureido)-1H-benzoimidazol-5-yl ester,
  4-cyclopentylamino-benzenesulfonic acid 2-(3-phenyl-ureido)-1H-benzoimidazol-5-yl ester,
  4-cyclopentylamino-benzenesulfonic acid 2-[3-(2-hydroxy-ethyl)-ureido]-1H-benzoimidazol-5-yl ester,
  4-cyclopentylamino-benzenesulfonic acid 2-[3-(4-fluoro-phenyl)-ureido]-1-benzoimidazol-5-yl ester,
  4-cyclopentylamino-benzenesulfonic acid 2-[3-(2-chloro-benzyl)-ureido]-1H-benzoimidazol-5-yl ester,
  4-cyclopentylamino-benzenesulfonic acid 2-[3-(2-fluoro-benzyl)-ureido]-1H-benzoimidazol-5-yl ester,
  4-cyclopentylamino-benzenesulfonic acid 2-[(azetidine-1-carbonyl)-amino]-1H-benzoimidazol-5-yl ester,
  4-cyclopentylamino-benzenesulfonic acid 2(3-benzyl-ureido)-1H-benzoimidazol-5-yl ester,
  4-cyclopentylamino-benzenesulfonic acid 2-[3-(3-hydroxy-propyl)-ureido]-1H-benzoimidazol-5-yl ester,
  4-cyclopentylamino-benzenesulfonic acid 2-[3-(1,1-dimethyl-propyl)-ureido]-1H-benzoimidazol-5-yl ester,
  4-cyclopentylamino-benzenesulfonic acid 2-[3-(4-hydroxy-butyl)-ureido]-1H-benzoimidazol-5-yl ester,
  4-cyclopentylamino-benzenesulfonic acid 2-[3-(2-hydroxy-1-methyl-ethyl)-ureido]-1H-benzoimidazol-5-yl ester,
  4-[(tetrahydro-furan-2-ylmethyl)-amino]-benzenesulfonic acid 2-[3-(2-hydroxy-ethyl)-ureido]-1H-benzoimidazol-5-yl ester,
  4-[(tetrahydro-furan-2-ylmethyl)-amino]-benzenesulfonic acid 2-[3-(3-hydroxy-propyl)-ureido]-1H-benzoimidazol-5-yl ester,
  4-[(tetrahydro-furan-2-ylmethyl)-amino]-benzenesulfonic acid 2-[3-(4-hydroxy-butyl)-ureido]-1H-benzoimidazol-5-yl ester,
  4-[(tetrahydro-furan-2-ylmethyl)-amino]-benzenesulfonic acid 2-[3-(2-methoxy-1-methyl-ethyl)-ureido]-1H-benzoimidazol-5-yl ester,
  4-[(tetrahydro-furan-2-ylmethyl)-amino]-benzenesulfonic acid 2-(3-ethyl-ureido)-1H-benzoimidazol-5-yl ester,
  4-(2-methoxy-ethylamino)-benzenesulfonic acid 2-[3-(2-ethyl)-ureido]-1H-benzoimidazol-5-yl ester, 4-(2-hydroxy-1-methyl-ethylamino)-benzenesulfonic acid 2-[3-(2-methoxy-ethyl)-ureido]-1H-benzoimidazol-5-yl ester, 4-(2-hydroxy-1-methyl-ethylamino)-benzenesulfonic acid 2-[3-(2-ethyl)-ureido]-1H-benzoimidazol-5-yl ester, 4-(2-morpholin-4-yl-ethylamino)-benzenesulfonic acid 2-[3-(2-methoxy-ethyl)-ureido]-1H-benzoimidazol-5-yl ester, 4-[(piperidin-4-ylmethyl)-amino]-benzenesulfonic acid 2-[3-(2-methoxy-ethyl)-ureido]-1H-benzoimidazol-5-yl ester, and 4-(2-hydroxy-3-methoxy-propylamino)-benzenesulfonic acid 2-[3-(2-hydroxy-3-methoxy-propyl)-ureido]-3H-benzoimidazol-5-yl ester.

11. The compound according to claim 4 wherein $R_2$ is —CO-cycloalkyl.

12. The compound according to claim 11 wherein $R_2$ is —CO-cyclopropyl.

13. The compound according to claim 12 selected from the group consisting of:

4-benzylamino-benzenesulfonic acid 2-(cyclopropanecarbonyl-amino)-1H-benzoimidazol-5-yl ester, 4-methylamino-benzenesulfonic acid 2-(cyclopropanecarbonyl-amino)-1H-benzoimidazol-5-yl ester, 4-(2-hydroxy-ethylamino)-benzenesulfonic acid 2-(cyclopropanecarbonyl-amino)-1H-benzoimidazol-5-yl ester, 4-(3-hydroxy-propylamino)-benzenesulfonic acid 2-(cyclopropanecarbonyl-amino)-1H-benzoimidazol-5-yl ester, 4-(4-hydroxy-butylamino)-benzenesulfonic acid 2-(cyclopropanecarbonyl-amino)-1H-benzoimidazol-5-yl ester, 4-(2-methoxy-1-methyl-ethylamino)-benzenesulfonic acid 2-(cyclopropanecarbonyl-amino)-1H-benzoimidazol-5-yl ester, 4-(2-pyrrolidin-1-yl-ethylamino)-benzenesulfonic acid 2-(cyclopropanecarbonyl-amino)-1H-benzoimidazol-5-yl ester, 4-(1-hydroxymethyl-propylamino)-benzenesulfonic acid 2-(cyclopropanecarbonyl-amino)-1H-benzoimidazol-5-yl ester, 4-(2-hydroxy-1-methyl-ethylamino)-benzenesulfonic acid 2-(cyclopropanecarbonyl-amino)-1H-benzoimidazol-5-yl ester, 4-(2-piperidin-1-yl-ethylamino)-benzenesulfonic acid 2-(cyclopropanecarbonyl-amino)-1H-benzoimidazol-5-yl ester, 4-(3-pyrrolidin-1-yl-propylamino)-benzenesulfonic acid 2-(cyclopropanecarbonyl-amino)-1H-benzoimidazol-5-yl ester, 4-(3-hydroxy-2,2-dimethyl-propylamino)-benzenesulfonic acid 2-(cyclopropanecarbonyl-amino-1H-benzoimidazol-5-yl ester, 4-[3-(4-methyl-piperazin-1-yl)-propylamino]-benzenesulfonic acid 2-(cyclopropanecarbonyl-amino)-1H-benzoimidazol-5-yl ester, 4-(2-methoxy-benzylamino)-benzenesulfonic acid 2-(cyclopropanecarbonyl-amino)-1H-benzoimidazol-5-yl ester, 4(2-diethylamino-ethylamino)-benzenesulfonic acid 2-(cyclopropanecarbonyl-amino)-1H-benzoimidazol-5-yl ester, 4-(1S-hydroxymethyl-propylamino)-benzenesulfonic acid 2-(cyclopropanecarbonyl-amino)-1H-benzoimidazol-5-yl ester, 4-(2-morpholin-4-yl-ethylamino)-benzenesulfonic acid 2-(cyclopropanecarbonyl-amino)-1H-benzoimidazol-5-yl ester, 4-(1-aza-bicyclo[2.2.2]oct-3-ylamino)-benzenesulfonic acid 2-(cyclopropane-carbonyl-amino)-1H-benzoimidazol-5-yl ester, 4-(2-piperazin-1-yl-ethylamino)-benzene-sulfonic acid 2-(cyclopropanecarbonyl-amino)-1H-benzoimidazol-5-yl ester, 4-(2-carbamoyl-cyclohexylamino)-benzenesulfonic acid 2-(cyclopropanecarbonyl-amino)-1H-benzoimidazol-5-yl ester, 4-(2-acetylamino-ethylamino)-benzenesulfonic acid 2-(cyclopropanecarbonyl-amino)-1H-benzoimidazol-5-yl ester, 4-[2-(2-amino-ethylamino)-ethylamino]-benzenesulfonic acid 2-(cyclopropanecarbonyl-amino)-1H-benzoimidazol-5-yl ester, 4-[2-(1H-imidazol-4-yl)-ethylamino]-benzenesulfonic acid 2-(cyclopropanecarbonyl-amino)-1H-benzoimidazol-5-yl ester, 4-[(pyridin-2-ylmethyl)-amino]-benzenesulfonic acid 2-(cyclopropane-carbonyl-amino)-1H-benzoimidazol-5-yl ester, 4-cyclobutylamino-benzenesulfonic acid 2-(cyclopropanecarbonyl-amino)-1H-benzoimidazol-5-yl ester, and 4-[2-(2-hydroxy-ethoxy)-ethylamino]-benzenesulfonic acid 2-(cyclopropanecarbonyl-amino)-1H-benzoimidazol-5-yl ester.

14. The compound according to claim 4 wherein $R_1$ is cyclopentylamino and $R_2$ is aryl a aralkyl optionally substituted by heterocyclyl selected from morpholinyl or methylpiperazinyl, alkyl, aryl, alkoxy, amino, fluoroalkyl, acyl derivative, or halogen.

15. The compound according to claim 14 selected from the group consisting of:

4-cyclopentylamino-benzenesulfonic acid 2-(3,4-dimethoxy-phenylamino)-1H-benzoimidazol-5-yl ester, 4-cyclopentylamino-benzenesulfonic acid 2-phenylamino-1H-benzoimidazol-5-yl ester, 4-cyclopentylamino-benzenesulfonic acid 2-(4-morpholin-4-yl-phenylamino)-1H-benzoimidazol-5-yl ester, 4-cyclopentylamino-benzenesulfonic acid 2-(3,5-dimethyl-phenylamino)-1H-benzoimidazol-5-yl ester, 4-cyclopentylamino-benzenesulfonic acid 2-(4-methoxy-phenylamino)-1H-benzoimidazol-5-yl ester, 4-cyclopentylamino-benzenesulfonic acid 2-(4-dimethylamino-phenylamino)-1H-benzoimidazol-5-yl ester, 4-cyclopentylamino-benzenesulfonic acid 2-(3-methoxy-5-trifluoromethyl-phenylamino)-1H-benzoimidazol-5-yl ester, 3-[5-(4-cyclopentylamino-benzenesulfonyloxy)-1H-benzoimidazol-2-ylamino]-benzoic acid ethyl ester, and 4-cyclopentylamino-benzenesulfonic acid 2-[(4-(4-methyl-piperazin-1-yl)-phenylamino)-1H-benzoimidazol-5-yl ester.

16. A pharmaceutical composition comprising a therapeutically effective amount of a compound of formula (I) according to claim 1 and one or more pharmaceutically acceptable adjuvants or diluents.

* * * * *

UNITED STATES PATENT AND TRADEMARK OFFICE
CERTIFICATE OF CORRECTION

PATENT NO.         : 7,041,668 B2
APPLICATION NO. : 10/808889
DATED                  : May 9, 2006
INVENTOR(S)        : Francois Clerc et al.

It is certified that error appears in the above-identified patent and that said Letters Patent is hereby corrected as shown below:

Column 1, Line 42 reads as:

"known substrate for cdk4 is the retinoblastonia gene product"

and should read as:

-- known substrate for CDK4 is the retinoblastoma gene product--

Column 1, Line 48 reads as:

"cycle progression, e.g. thymidine kinase, thymdylate syn-"

and should read as:

--cycle progression, e.g. thymidine kinase, thymidylate syn- --

Column 2, the structure beginning at Line 32 reads as:

" 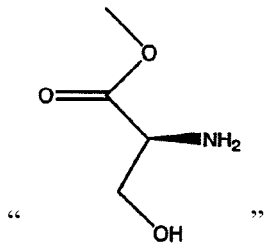 "

and should read as:

-- 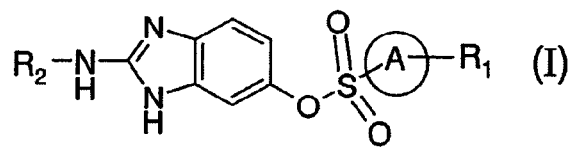 --

UNITED STATES PATENT AND TRADEMARK OFFICE
CERTIFICATE OF CORRECTION

| | |
|---|---|
| PATENT NO. | : 7,041,668 B2 |
| APPLICATION NO. | : 10/808889 |
| DATED | : May 9, 2006 |
| INVENTOR(S) | : Francois Clerc et al. |

It is certified that error appears in the above-identified patent and that said Letters Patent is hereby corrected as shown below:

Column 3, Line 28 reads as:

"lamino sutstituent. In the preferred compounds of formula"

and should read as:

-- lamino substituent. In the preferred compounds of formula--

Column 160, Line 37 reads as:

"b 1-imidazolyl" and should read as:

--1-imidazolyl--

Column 164, Line 33 reads as:

"cyclopentylamino and $R_2$ is aryl a aralkyl optionally substi-"

and should read as:

--cyclopentylamino and $R_2$ is aryl or aralkyl optionally substi- --

Signed and Sealed this

Seventeenth Day of October, 2006

JON W. DUDAS
*Director of the United States Patent and Trademark Office*